(12) United States Patent
Trawick et al.

(10) Patent No.: US 9,109,236 B2
(45) Date of Patent: Aug. 18, 2015

(54) MICROORGANISMS AND METHODS FOR CONVERSION OF SYNGAS AND OTHER CARBON SOURCES TO USEFUL PRODUCTS

(71) Applicant: Genomatica, Inc., San Diego, CA (US)

(72) Inventors: John D. Trawick, La Mesa, CA (US); Mark J. Burk, San Diego, CA (US); Anthony P. Burgard, Bellefonte, PA (US)

(73) Assignee: GENOMATICA, INC., San Diego, CA (US)

( * ) Notice: Subject to any disclaimer, the term of this patent is extended or adjusted under 35 U.S.C. 154(b) by 0 days.

(21) Appl. No.: 13/920,927

(22) Filed: Jun. 18, 2013

(65) Prior Publication Data

US 2014/0147900 A1    May 29, 2014

Related U.S. Application Data

(60) Division of application No. 13/371,278, filed on Feb. 10, 2012, now Pat. No. 8,470,566, which is a continuation of application No. 12/639,977, filed on Dec. 16, 2009, now Pat. No. 8,129,155, which is a continuation-in-part of application No. PCT/US2009/050757, filed on Jul. 15, 2009.

(60) Provisional application No. 61/138,108, filed on Dec. 16, 2008.

(51) Int. Cl.

| C12P 7/18 | (2006.01) |
|---|---|
| C12P 7/04 | (2006.01) |
| C12P 7/42 | (2006.01) |
| C12N 1/20 | (2006.01) |
| C12N 1/00 | (2006.01) |
| C07C 29/00 | (2006.01) |
| C07C 27/26 | (2006.01) |
| C12N 9/04 | (2006.01) |
| C12N 9/10 | (2006.01) |
| C12N 9/88 | (2006.01) |
| C12N 15/52 | (2006.01) |

(52) U.S. Cl.
CPC ............... *C12P 7/18* (2013.01); *C12N 9/0006* (2013.01); *C12N 9/10* (2013.01); *C12N 9/1029* (2013.01); *C12N 9/88* (2013.01); *C12N 15/52* (2013.01); *C12P 7/04* (2013.01); *C12P 7/42* (2013.01)

(58) Field of Classification Search
CPC ...... C12N 9/0006; C12N 9/10; C12N 9/1029; C12N 15/52; C12N 9/88; C12P 7/42; C12P 7/04; C12P 7/18
USPC ............. 435/158, 157, 146, 252.3, 254.11, 435/254.2; 568/840, 854
See application file for complete search history.

(56) References Cited

U.S. PATENT DOCUMENTS

| 5,958,745 A | 9/1999 | Gruys et al. |
|---|---|---|
| 6,432,686 B1 | 8/2002 | Bulthuis et al. |
| 7,127,379 B2 | 10/2006 | Palsson et al. |
| 7,799,545 B2 | 9/2010 | Burgard et al. |
| 7,803,589 B2 | 9/2010 | Burk et al. |
| 7,858,350 B2 | 12/2010 | Burk et al. |
| 7,947,483 B2 | 5/2011 | Burgard |
| 7,977,084 B2 | 7/2011 | Sun et al. |
| 8,026,386 B2 | 9/2011 | Burk et al. |
| 8,048,661 B2 | 11/2011 | Burgard et al. |
| 8,062,871 B2 | 11/2011 | Burgard et al. |
| 8,067,214 B2 | 11/2011 | Burk et al. |
| 8,088,607 B2 | 1/2012 | Burgard et al. |
| 8,129,154 B2 | 3/2012 | Burk et al. |
| 8,129,155 B2 | 3/2012 | Trawick et al. |
| 8,129,156 B2 | 3/2012 | Burk et al. |
| 8,129,169 B2 | 3/2012 | Van Dien et al. |
| 8,178,327 B2 | 5/2012 | Burk et al. |
| 8,241,877 B2 | 8/2012 | Burgard et al. |
| 8,268,607 B2 | 9/2012 | Burgard |
| 8,470,566 B2 * | 6/2013 | Trawick et al. ............... 435/146 |
| 2002/0012939 A1 | 1/2002 | Palsson |
| 2002/0168654 A1 | 11/2002 | Maranas et al. |
| 2003/0059792 A1 | 3/2003 | Palsson et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0029149 A1 | 2/2004 | Palsson et al. |
| 2004/0072723 A1 | 4/2004 | Palsson et al. |

(Continued)

FOREIGN PATENT DOCUMENTS

| WO | WO 99/58686 | 11/1999 |
|---|---|---|
| WO | WO 02/055995 | 7/2002 |

(Continued)

OTHER PUBLICATIONS

Ahmed and Lewis, "Fermentation of Biomass-Generated Synthesis Gas: Effects of Nitric Oxide," *Biotechol. Bioeng.* 97:1080-1086 (2007).
Alber et al., "Malonyl-Coenzyme A reductase in the modified 3-hydroxypropionate cycle for autotrophic carbon fixation in archaeal *Metallosphaera* and *Sulfolobus* spp.," *J. Bacteriol.* 188(24):8551-8559 (2006).
Andreesen and Ljungdahl, "Formate Dehydrogenase of *Clostridium thermoaceticum*: Incorporation of Selenium-75, and the Effects of Selenite, Molybate, and Tungstate on the Enzyme," *J. Bacteriol.* 116(2):867-873 (1973).
Angrand et al., "Simplified generation of targeting constructs using ET recombination," *Nucleic Acids Res.* 27(17):e16 (1999).
Aragon and Lowenstein, "A survey of Enzymes Which Generate or Use Acetoacetyl Thioesters in Rat Liver," *J. Biol. Chem.* 258(8):4725-4733 (1983).

(Continued)

*Primary Examiner* — Ganapathirama Raghu
(74) *Attorney, Agent, or Firm* — Kagan Binder, PLLC

(57) ABSTRACT

A non-naturally occurring microbial organism having an isopropanol, 4-hydroxybutyrate, or 1,4-butanediol pathway includes at least one exogenous nucleic acid encoding an isopropanol, 4-hydroxybutyrate, or 1,4-butanediol pathway enzyme expressed in a sufficient amount to produce isopropanol, 4-hydroxybutyrate, or 1,4-butanediol. The aforementioned organisms are cultured to produce isopropanol, 4-hydroxybutyrate, or 1,4-butanediol.

23 Claims, 17 Drawing Sheets

(56) References Cited

U.S. PATENT DOCUMENTS

| | | |
|---|---|---|
| 2007/0111294 A1 | 5/2007 | Burgard et al. |
| 2008/0199926 A1 | 8/2008 | Burgard et al. |
| 2008/0293125 A1 | 11/2008 | Subbian et al. |
| 2010/0021978 A1 | 1/2010 | Burk et al. |
| 2010/0184173 A1 | 7/2010 | Burk et al. |
| 2010/0317069 A1 | 12/2010 | Burk et al. |
| 2010/0323418 A1 | 12/2010 | Burgard |
| 2010/0330635 A1 | 12/2010 | Burgard et al. |
| 2011/0003344 A1 | 1/2011 | Burk et al. |
| 2011/0003355 A1 | 1/2011 | Clark et al. |
| 2011/0008858 A1 | 1/2011 | Osterhout et al. |
| 2011/0014668 A1 | 1/2011 | Osterhout et al. |
| 2011/0097767 A1 | 4/2011 | Pharkya |
| 2011/0129899 A1 | 6/2011 | Haselbeck et al. |
| 2011/0195461 A1 | 8/2011 | Burk et al. |
| 2011/0201068 A1 | 8/2011 | Pharkya et al. |
| 2011/0201071 A1 | 8/2011 | Burgard et al. |
| 2011/0207185 A1 | 8/2011 | Osterhout |
| 2011/0207189 A1 | 8/2011 | Osterhout |
| 2011/0212507 A1 | 9/2011 | Burgard et al. |
| 2011/0217742 A1 | 9/2011 | Sun et al. |
| 2011/0223637 A1 | 9/2011 | Burk et al. |
| 2011/0229946 A1 | 9/2011 | Haselbeck et al. |
| 2011/0269204 A1 | 11/2011 | Burk et al. |
| 2011/0300597 A1 | 12/2011 | Burk et al. |
| 2011/0312049 A1 | 12/2011 | Osterhout et al. |
| 2012/0021478 A1 | 1/2012 | Osterhout et al. |
| 2012/0040426 A1 | 2/2012 | Sun et al. |
| 2012/0094345 A1 | 4/2012 | Burk et al. |
| 2012/0115194 A1 | 5/2012 | Burgard et al. |
| 2012/0122171 A1 | 5/2012 | Burk et al. |
| 2012/0156740 A1 | 6/2012 | Pharkya et al. |
| 2012/0208249 A1 | 8/2012 | Trawick et al. |
| 2012/0225463 A1 | 9/2012 | Van Dien et al. |
| 2012/0225466 A1 | 9/2012 | Burk et al. |
| 2012/0237990 A1 | 9/2012 | Burk et al. |
| 2012/0264179 A1 | 10/2012 | Burgard et al. |

FOREIGN PATENT DOCUMENTS

| | | |
|---|---|---|
| WO | WO 03/106998 | 12/2003 |
| WO | WO 2008/115840 | 9/2008 |
| WO | WO 2008/152016 | 12/2008 |

OTHER PUBLICATIONS

Atsumi et al., "Metabolic engineering of *Escherichia coli* for 1-butanol production," *Metab. Eng.* 10(6):305-311 (2007).

Atsumi et al., "Non-fermentative pathways for synthesis of branched-chain higher alcohols as biofuels," *Nature* 451(7174):86-89 (2008).

Ausubel, et al., Current Protocols in Molecular Biology, John Wiley and Sons, Baltimore, MD (1999).

Barker et al., "Butyryl-CoA:Acetoacetate CoA-transferase from Lysine-fermenting *Clostridium*," *J. Biol. Chem.* 253(4):1219-1225 (1978).

Barker et al., "Pathway of Lysine Degradation in *Fusobacterium nucleatum*," *J. Bacteriol.* 152(1):201-207 (1982).

Barrick, et al., "Quantitative analysis of ribosome binding sites in *E. coli*," *Nucleic Acids Res.* 22(7):1287-1295 (1994).

Berg et al., "A 3-Hydroxypropionate/4-Hydroxybutyrate Autotrophic Carbon Dioxide Assimilation Pathway in Archaea," *Science* 318(5857) 1782-1786 (2007).

Bisswanger, "Substrate specificity of the Pyruvate Dehydrogenase Complex from *Escherichia coli*," *J. Biol. Chem.* 256(2):815-822 (1981).

Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).

Bonner and Bloch, "Purification and properties of fatty acyl thioesterase I from *Escherichia coli*," *J. Biol. Chem.* 247(10):3123-3133 (1972).

Bose et al., "Genetic analysis of the methanol- and methylamine-specific methyltransferase 2 genes of *Methanosarcina acetivorans* C2A," *J. Bacteriol.* 190(11):4017-4026 (2008).

Bower et al., "Cloning, sequencing, and characterization of the *Bacillus subtilis* biotin biosynthetic operon," *J. Bacteriol.* 178(14):4122-4130 (1996).

Boynton et al., "Cloning, sequencing, and expression of clustered genes encoding β-hydroxybutyryl-Coenzyme A (CoA) dehydrogenase, crotonase, and butyryl-CoA dehydrogenase from *Clostridium acetobutylicum* ATCC 824," *J. Bacteriol.* 178(11):3015-3024 (1996).

Bräsen and Schönheit, "Unusual ADP-forming acetyl-Coenzyme A synthetases from the mesophilic halophilic euryarchaeon *Haloarcula marismortui* and from the hyperthermophilic crenarchaeon *Pyrobaculum aerophilum*," *Arch. Microbiol.* 182(4):277-287 (2004).

Bravo et al., "Reliable, sensitive, rapid and quantitative enzyme-based assay for gamma-hydroxybutyric acid (GHB)," *J. Forensic Sci.* 49:379-387 (2004).

Bredwell et al., "Reactor Design Issues for Synthesis-Gas Fermentations," *Biotechnol. Prog.* 15(5):834-844 (1999).

Breitkruez et al., "A novel γ-hydroxybutyrate dehydrogenase: Identification and expression of an *Arabidopsis* cDNA and potential role under oxygen deficiency," *J. Biol. Chem.* 278:41552-41556 (2003).

Bremer, "Pyruvate Dehydrogenase, Substrate Specificity and Product Inhibition," *Eur. J. Biochem.* 8:535-540 (1969).

Brey et al., "Cloning of multiple genes involved with cobalamin (Vitamin B12) biosynthesis in *Bacillus megaterium*," *J. Bacteriol.* 167:623-630 (1986).

Burgard et al., "Minimal Reaction Sets for *Escherichia coli* Metabolism under Different Growth Requirements and Uptake Environments," *Biotechnol. Prog.* 17:791-797 (2001).

Burgard et al., "Optknock: a bilevel programming framework for identifying gene knockout strategies for microbial strain optimization," *Biotechnol. Bioeng.* 84(6):647-657 (2003).

Buu et al., "Functional characterization and localization of acetyl-CoA hydrolase, Ach1p, in *Saccharomyces cerevisiae*," *J. Biol. Chem.* 278:17203-17209 (2003).

Campbell et al., "A new *Escherichia coli* metabolic competency: growth on fatty acids by a novel anaerobic β-oxidation pathway," *Mol. Microbiol.* 47(3):793-805 (2003).

Clark and Ljungdahl, "Purification and Properties of 5,10-Methylenetetrahydrofolate Reductase, an Iron-sulfur Flavoprotein from *Clostridium formicoaceticum*," *J. Biol. Chem.* 259(17)10845-10849 (1984).

Clark and Ljungdahl, "Purification and properties of 5,10-methylenetetrahydrofolate reductase from *Clostridium formicoaceticum*," *Methods Enzymol.* 122:392-399 (1986).

Colby and Chen, "Purification and properties of 3-hydroxybutyryl-Coenzyme A dehydrogenase from *Clostridium beijerinckii* ("*Clostridium butylicum*") NRRL B593," *Appl. Environ. Microbiol.* 58:3297-3302 (1992).

Corthesy-Theulaz et al., "Cloning and Characterization of *Helicobacter pylori* Succinyl CoA:Acetoacetate CoA-transferase, a Novel Prokaryotic Member of the CoA-transferase Family," *J. Biol. Chem.* 272(41):25659-25667 (1997).

D'Ari and Rabinowitz, "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from *Escherichia coli*," *J. Biol. Chem.* 266(35):23953-23958 (1991).

Das et al., "Characterization of a corrinoid protein involved in the C1 metabolism of strict anaerobic bacterium *Moorella thermoacetica*," *Proteins* 67(1):167-176 (2007).

Datar et al., "Fermentation of biomass-generated producer gas to ethanol," *Biotechnol. Bioeng.* 86(5):587-594 (2004).

de Bok et al., "Two W-containing formate dehydrogenases (CO2-reductases) involving syntrophic propionate oxidation by *Syntrophobacter fumaroxidans*," *Eur. J. Biochem.* 270:2476-2485 (2003).

de Mata and Rabinowitz, "Formyl-methenyl-methylenetetrahydrofolate synthetase (combined) from yeast. Bio-

(56) References Cited

OTHER PUBLICATIONS chemical characterization of the protein from an ADE3 mutant lacking the formyltetrahydrofolate synthetase function," *J. Biol Chem.* 255:2569-2577 (1980).

Deana, "Substrate specificity of a dicarboxyl-CoA: dicarboxylic acid Coenzyme A transferase from rat liver mitochondria," *Biochem. Int.* 26(4):767-773 (1992).

Dobbek et al., "Crystal structure of a carbon monoxide dehydrogenase reveals a [Ni-4Fe-5S] cluster," *Science* 293(5533):1281-1285 (2001).

Drake and Daniel, "Physiology of the thermophilic acetogen *Moorella thermoacetica*," *Res. Microbiol.* 155(10):869-883 (2004).

Drake, "Demonstration of hydrogenase in extracts of the homoacetate-fermenting bacterium *Clostridium thermoaceticum*," *J. Bacteriol.* 150(2):702-709 (1982).

Fontaine et al., "Molecular charcterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol.* 184:821-830 (2002).

Fontaine et al., "A New Type of Glucose Fermentation by *Clostridium thermoaceticum* N.Sp.," *J. Bacteriol.* 43(6):701-715 (1942).

Ford et al., "Molecular properties of the lyst1+ gene and the regulation of α-aminoadipate reductase in *Schizosaccharomyces pombe*," *Curr. Genet.* 28:131-137 (1995).

Fox et al., "Characterization of the region encoding the CO-induced hydrogenase of *Rhodospirillum rubrum*," *J. Bacteriol.* 178(21):6200-6208 (1996).

Freidrich et al., "The complete stereochemistry of the enzymatic dehydration of 4-hydroxybutyryl Coenzyme A to crotonyl Coenzyme A," *Angew. Chem. Int. Ed.* 47:3254-3257 (2008).

Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics* 68:144-151 (2000).

Furdui and Ragsdale, "The role of pyruvate ferredoxin oxidoreductase in pyruvate synthesis during autotrophic growth by the Wood-Ljungdahl pathway," *J. Biol. Chem.* 275(37):28494-28499 (2000).

Galagan et al., "The genome of M. acetivorans reveals extensive metabolic and physiological diversity," *Genome Res.* 12(4):532-542 (2002).

Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).

González and Robb, "Genetic analysis of *Carboxydothermus hydrogenoformans* carbon monoxide dehydrogenase genes cooF and cooS," *FEMS Microbiol. Lett.* 191(2):243-247 (2000).

Guo and Bhattacharjee, "Posttranslational activation, site-directed mutation and phylogenetic analyses of the lysine biosynthesis enzymes a-aminoadipate reductase Lys1p (AAR) and the phosphopantetheinyl transferase Lys7p (PPTase) from *Schizosaccharomyces pombe*," *Yeast* 21:1279-1288 (2004).

Guo and Bhattacharjee, "Site-directed mutational analysis of the novel catalytic domains of a-aminoadipate reductase (Lys2p) from *Candida albicans*," *Mol. Gen. Gemonics* 269:271-279 (2003).

Hagemeier et al., "Insight into the mechanism of biological methanol activation based on the crystal structure of the methanol-cobalamin methyltransferase complex," *Proc. Natl. Acad. Sci. U.S.A.* 103(50):18917-18922 (2006).

Hanai et al., "Engineered synthetic pathway for isopropanol production in *Escherichia coli*," *Appl. Environ. Microbiol.* 73(24):7814-7818 (2007).

Harms and Thauer, "Methylcobalamin: Coenzyme M methyltransferase isoenzymes MtaA and MtbA from *Methanosarcina barkeri*. Cloning, sequencing and differential transcription of the encoding genes, and functional overexpression of the mtaA gene in *Escherichia coli*," *Eur. J. Biochem.* 235(3):653-659 (1996).

Hasegawa et al., "Transcriptional regulation of ketone body-utilizing enzyme, acetoacetyl-CoA synthetase, by C/EBPa during adipocyte differentiatiion," *Biochimica. Biophysica. Acta* 1779:414-419 (2008).

Herrmann et al., "Energy Conservation via Electron-Transferring Flavoprotein in Anaerobic Bacteria," *J. Bacteriol.* 190(3):784-791 (2008).

Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).

Hijarrubia et al., "Domain Structure Characterization of the Multifunctional α-Aminoadipate Reductase from *Penicillium chrysogenum* by Limited Proteolysis," *J. Biol. Chem.* 278(10):8250-8256 (2003).

Hiser et al., "ERG10 from *Saccharomyces cerevisiae* encodes acetoacetyl-CoA thiolase," *J. Biol. Chem.* 269:31383-31389 (1994).

Hoffmeister et al., "Mitochondrial trans-2-enoyl-CoA reductase of wax ester fermentation from *Euglena gracilis* defines a new family of enzymes involved in lipid synthesis," *J. Biol. Chem.* 280(6):4329-4338 (2005).

Huang et al., "Identification and characterization of a second butyrate kinase from *Clostridium acetobutylicum* ATCC 824," *J. Mol. Microbiol. Biotechnol.* 2(1):33-38 (2000).

Hugler et al., "Malonyl-Coenzyme A Reductase from *Chloroflexus aurantiacus*, a Key Enzyme of the 3-Hydroxypropionate Cycle for Autotrophic CO2 Fixation," *J. Bacteriol.* 184(9):2404-2410 (2002).

Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).

Ismail et al., "Functional genomics by NMR spectroscopy. Phenylacetate catabolism in *Escherichia coli*," *Eur. J. Biochem.* 270(14):3047-3054 (2003).

Jacobi et al., "The hyp operon gene products are required for the maturation of catalytically active hydrogenase isoenzymes in *Escherichia coli*," *Arch. Microbiol.* 158(6):444-451 (1992).

Jojima et al., "Production of isopropanol by metabolically engineered *Escherichia coli*," *Appl. Microbiol. Biotechnol.* 77:1219-1224 (2008).

Kapatral et al., "Genome Sequence and Analysis of the Oral Bacterium *Fusobacterium nucleatum* Strain ATCC 25586," *J. Bacteriol.* 1840:2005-2018 (2002).

Kazahaya et al, "Aerobic Dissimilation of Glucose by Heterolactic Bacteria III. Aldehyde dehydrogenase and alcohol dehydrogenase of luconostoc mesenteroids" *J. Gen. Appl. Microbiol.* 18(1):43-55 (1972).

Kellum and Drake, "Effects of cultivation gas phase on hydrogenase of the acetogen *Clostridium thermoaceticum*," *J. Bacteriol.* 160(1):466-469 (1984).

Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).

Kim et al., "Construction of an *Escherichia coli* K-12 Mutant for Homoethanologenic Fermentation of Glucose or Xylose without Foreign Genes," *Appl. Environ. Microbiol.* 73(6):1766-1771 (2007).

Kim et al., "Dihydrolipoamide dehydrogenase mutation alters the NADH sensitivity of pyruvate dehydrogenase complex of *Escherichia coli* K-12," *J. Bacteriol.* 190:3851-3858 (2008).

Kinoshita, "Purification of two alcohol dehydrogenases from *Zymomonas mobilis* and their properties," *Appl. Microbiol. Biotechnol.* 22:249-254 (1985).

Klasson, et al., "Biological conversion of coal and coal-derived synthesis gas," *Fuel* 72(12):1673-1678 (1993).

Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).

(56) References Cited

OTHER PUBLICATIONS

Knappe and Sawers, "A radical-chemical route to acetyl-CoA: the anaerobically induced pyruvate formate-lyase system of *Escherichia coli*," *FEMS. Microbiol. Rev.* 75:383-398 (1990).

Koland and Bennis, "Proximity of Reactive Cysteine Residue and Flavin in *Escherichia coli* Pyruvate Oxidase as Estimated by Flourescence Energy Transfer," *Biochemistry* 21:4438-4442 (1982).

Koo et al., "Cloning and characterization of the bifunctional alcohol/acetaldehyde dehydrogenase gene (adhE) in *Leuconostoc mesenteroides* isolated from kimchi," *Biotechnol. Lett.* 27(7):505-510 (2005).

Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).

Kreimeyer et al., "Identification of the Last Unknown Genes in the Fermentation Pathway of Lysine," *J. Biol. Chem.* 282(10):7191-7197 (2007).

Kumari et al., "Cloning, Characterization, and Functional Expression of acs, the Gene Which Encodes Acetyl Coenzyme A Synthetase in *Escherichia coli*," *J. Bacteriol.* 177(10): 2878-2886 (1995).

Kuznetsova et al., "Enzyme genomics: Application of general enzymatic screens to discover new enzymes," *FEMS Microbiol. Rev.* 29(2):263-279 (2005).

Lamas-Maceiras et al., "Amplification and disruption of the phenylacetyl-CoA ligase gene of *Penicillium chrysogenum* encoding an aryl-capping enzyme that supplies phenylacetic acid to the isopenicillin N-acyltransferase," *Biochem. J.* 395(1):147-155 (2006).

Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).

Lee et al., "Biosynthesis of enantiopure (S)-3-hydroxybutyric acid in metabolically engineered *Escherichia coli*," *App. Microbiol. Biotechnol.* 79:633-641 (2008).

Lessner et al., "An unconventional pathway for reduction of $CO_2$ to methane in CO-grown *Methanosarcina acetivorans* revealed by proteomics," *Proc. Natl. Acad. Sci. U.S.A.* 103(47):17921-17926 (2006).

Li et al., "Properties of Nicotinamide Adenine Dinucleotide Phosphate-Dependent Formate Dehydrogenase from *Clostridium thermoaceticum*," *J. Bacteriol.* 92(2):405-412 (1966).

Lin et al., "Fed-batch culture of a metabolically engineered *Escherichia coli* strain designed for high-level succinate production and yield under aerobic conditions," *Biotechnol. Bioeng.* 90:775-779 (2005).

Link et al., "Methods for generating precise deletions and insertions in the genome of wild-type *Eshcerichia coli*: application to open reading frame characterization," *J. Bacteriol.* 179:6228-6237 (1997).

Ljungdahl and Andreesen, "Formate dehydrogenase, a selenium-tungsten enzyme from *Clostridium thermoaceticum*," *Methods Enzymol.* 53:360-372 (1978).

Ljungdahl and Andreesen, "Tungsten, a component of active formate dehydrogenase from *Clostridium thermoacetium*," *FEBS Lett.* 54:279-282 (1975).

Louis et al., "Restricted distribution of the butyrate kinase pathway among butyrate-producing bacteria from the human colon," *J. Bacteriol.* 186:2099-2106 (2004).

Lovell et al., "Cloning and expression in *Escherichia coli* of the *Clostridium thermoaceticum* gene encoding thermostable formyltetrahydrofolate synthetase," *Arch. Microbiol.* 149(4):280-285 (1988).

Lovell, et al., "Primary structure of the thermostable formyltetrahydrofolate synthetase from *Clostridium thermoaceticum*," *Biochemistry* 20(29):5687-5694 (1990).

Lu et al., "Sequence and expression of the gene encoding the corrinoid/iron-sulfur protein from *Clostridium thermoaceticum* and reconstitution of the recombinant protein to full activity," *J. Biol. Chem.* 268(8):5605-5614 (1993).

Lutz and Bujard, "Independent and tight regulation of transcriptional units in *Escherichia coli* via the LacR/O, the TetR/O and AraC/I1-I2 regulatory elements," *Nucleic Acids Res.* 25(6):1203-1210 (1997).

Mack and Bucket, "Conversion of glutaconate CoA-transferase from *Acidaminococcus fermentans* into an acyl-CoA hydrolase by site-directed mutagenesis," *FEBS Lett.* 405(2):209-212 (1997).

Maeder et al., "The *Methanosarcina barkeri* genome: comparative analysis with *Methanosarcina acetivorans* and *Methanosarcina mazei* reveals extensive rearrangement within methanosarcinal genomes," *J. Bacteriol.* 188(22):7922-7931 (2006).

Martin et al., "Engineering a mevalonate pathway in *Escherichia coli* for production of terpenoids," *Nat. Biotechnol.* 21:796-802 (2003).

Martínez-Blanco, et al, "Purification and biochemical characterization of phenylacetyl-CoA ligase from *Pseudomonas putida*. A specific enzyme for the catabolism of phenylacetic acid," *J. Biol. Chem.* 265(12):7084-7090 (1990).

Mattevi et al., "Atomic structure of the cubic core of the pyruvate dehydrogenase multienzyme complex," *Science* 255(5051):1544-1550 (1992).

Melchiorsen et al., "The level of pyruvate-formate lyase controls the shift from homolactic to mixed-acid product formation in *Lactococcus lactis*," *Appl. Microbiol. Biotechnol.* 58:338-344 (2002).

Menon and Ragsdale, "Mechanism of the *Clostridium thermoaceticum* pyruvate:ferredoxin oxidoreductase: evidence for the common catalytic intermediacy of the hydroxyethylthiamine pyrophosphate radical," *Biochemistry* 36(28):8484-8494 (1997).

Menzel et al., "Enzymatic evidence for an involvement of pyruvate dehydrogenase in the anaerobic glycerol metabolism of *Klebsiella pneumoniae*," *J. Biotech.* 56:135-142 (1997).

Morris and Jinks-Robertson, "Nucleotide sequence of the LYS2 gene of *Saccharomyces cerevisiae*: homology to *Bacillus brevis* tyrocidine synthetase 1," *Gene* 98:141-145 (1991).

Morton et al., "Cloning, sequencing, and expressions of genes encoding enzymes of the autotrophic acetyl-CoA pathway in the acetogen *Clostridium thermoaceticum*," in M. Sebald (ed.), *Genetics and molecular biology of anaerobic bacteria*, Springer Verlag, New York, 389-406 (1992).

Morton et al., "The primary structure of the subunits of carbon monoxide dehydrogenase/acetyl-CoA synthase from *Clostridium thermoaceticum*," *J. Biol. Chem.* 266(35):23824-23828 (1991).

Müh et al., "4-Hydroxybutyryl-CoA dehydratase from *Clostridium aminobutyricum*: characterization of FAD and iron-sulfur clusters involved in an overall non-redox reaction," *Biochemistry* 35:11710-11718 (1996).

Müh et al., "Mössbauer study of 4-hydroxybutyryl-CoA dehydratase probing the role of an iron-sulfur cluster in an overall non-redox reaction," *Eur. J. Biochem.* 248:380-384 (1997).

Musfeldt and Schönheit, "Novel type of ADP-forming acetyl Coenzyme A synthetase in *Hyperthermophilic archaea*: heterologous expression and characterization of isoenzymes from the sulfate reducer *Archaeoglobus fulgidus* and the methanogen *Methanococcus jannaschii*," J. Bacteriol. 184(3):636-644 (2002).

Muyrers et al., "Rapid modification of bacterial artificial chromosomes by ET-recombination," *Nucleic Acids Res.* 27:1555-1557 (1999).

Naggert et al., "Cloning, sequencing, and characterization of *Escherichia coli* thioesterase II," *J. Biol. Chem.* 266(17):11044-11050 (1991).

Nahvi et al., "Genetic Control by a Metabolite Binding mRNA," *Chem. Biol.* 9:1043-1049 (2002).

Naidu and Ragsdale, "Characterization of a three-component vanillate O-demethylase from *Moorella thermoacetica*," *J. Bacteriol.* 183(11):3276-3281 (2001).

Najafpour and Younesi, "Ethanol and acetate synthesis from waste gas using batch culture of *Clostridium ljungdahlii*," *Enzyme Microb. Technol.* 38:223-228 (2006).

Nakano et al., "Characterization of Anaerobic Fermentative Growth of *Bacillus subtilis*: Identification of Fermentation End Products and Genes Required for Growth," *J. Bacteriol.* 179(21):6749-6755 (1997).

O'Brien and Gennis, "Studies of the Thiamin Pyrophosphate Binding Site of *Escherichia coli* Pyruvate Oxidase," *J. Biol. Chem.* 255(8):3302-3307 (1980).

(56) References Cited

OTHER PUBLICATIONS

O'Brien et al, "Regulation by Lipids of Cofactor Binding to a Peripheral Membrane Enzyme: Binding of Thiamin Pyrophosphate to Pyruvate Oxidase," *Biochemistry* 16(14):3105-3109 (1977).

O'Brien et al., "Chemical, physical and enzymatic comparisons of formyltetrahydrofolate synthetases from thermo- and mesophilic clostridia," *Experientia. Suppl.* 26:249-262 (1976).

Ohgami et al., "Expression of acetoacetyl-CoA synthetase, a novel cytosolic ketone body-utilizing enzyme, in human brain," *Biochem. Pharmacol.* 65:989-994 (2003).

Olivera et al., "Molecular characterization of the phenylacetic acid catabolic pathway in *Pseudomonas putida* U: the phenylacetyl-CoA catabolon," Proc. Natl. Acad. Sci. U.S.A. 95(11):6419-6424 (1998).

Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).

Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).

Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).

Parkin et al., "Rapid and efficient electrocatalytic CO2/CO interconversions by *Carboxydothermus hydrogenoformans* CO dehydrogenase I on an electrode," *J. Am. Chem. Soc.* 129(34):10328-10329 (2007).

Peretz et al., "Molecular cloning, nucleotide sequencing, and expression of genes encoding alcohol dehydrogenases from the thermophile *Thermoanaerobacter brockii* and the mesophile *Clostridium beijerinckii*," *Anaerobe.* 3:259-270 (1997).

Petersen and Bennett, "Purification of acetoacetate decarboxylase from *Clostridium acetobutylicum* ATCC 824 and cloning of the acetoacetate decarboxylase gene in *Escherichia coli*," *Appl. Environ. Microbiol.* 56:3491-3498 (1990).

Pierce et al., "The Complete Genome Sequence of *Moorella thermoacetia* (f. *Clostridum thermoaceticum*)," *Environ. Microbiol.* 10(10):2550-2573 (2008).

Pieulle et al., "Isolation and analysis of the gene encoding the pyruvate-ferredoxin oxidoreductase of *Desulfovibrio africanus*, production of the recombinant enzyme in *Escherichia coli*, and effect of carboxy-terminal deletions on its stability," *J. Bacteriol.* 179(18):5684-5692 (1997).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).

Pritchett and Metcalf, "Genetic, physiological and biochemical characterization of multiple methanol methyltransferase isozymes in *Methanosarcina acetivorans* C2A," *Mol. Microbiol.* 56(5):1183-1194 (2005).

Ragsdale, "Life with carbon monoxide," *Crit. Rev. Biochem. Mol. Biol.* 39(3):165-195 (2004).

Ragsdale, "Pyruvate ferredoxin oxidoreductase and its radical intermediate," *Chem. Rev.* 103(6):2333-2346 (2003).

Ragsdale et al., "Acetogenisis and te Wood-Ljungdahl pathewy of CO2 fixation," Biochimica et Biophysica Acta, 1784(12):1873-1898 (2008).

Rangarajan et al., "Structure of [NiFe] hydrogenase maturation protein HypE from *Escherichia coli* and its interaction with HypF," *J. Bacteriol.* 190(4):1447-1458 (2008).

Raux et al., "The role of *Saccharomyces cerevisiae* Met1p and Met8p in sirohaem and cobalamin biosynthesis," *Biochem. J.* 338 (pt. 3):701-708 (1999).

Raux et al., "*Salmonella typhimurium* cobalamin (vitamin B12) biosynthetic genes: functional studies in *S. typhimurium* and *Escherichia coli*," *J. Bacteriol.* 178(3):753-767 (1996).

Raybuck et al., "Kinetic characterization of the carbon monoxide-acetyl-CoA (carbonyl group) exchange activity of the acetyl-CoA synthesizing CO dehydrogenase from *Clostridium thermoaceticum*," *Biochemistry* 27(20):7698-7702 (1988).

Reda et al., "Reversible interconversion of carbon dioxide and formate by an electroactive enzyme," *Proc. Natl. Acad. Sci. U.S.A.* 105:10654-10658 (2008).

Reiser and Somerville, "Isolation of mutants of *Acinetobacter calcoaceticus* deficient in wax ester synthesis and complementation of one mutation with a gene encoding a fatty acyl Coenzyme A reductase," *J. Bacteriol.* 179(9):2969-2975 (1997).

Ringquist et al., "Translation initiation in *Escherichia coli*: sequences within the ribosome-binding site," *Mol. Microbiol.* 6(9):1219-1229 (1992).

Rioux et al., "Two outer membrane transport systems for vitamin B12 in *Salmonella typhimurium*," *J. Bacteriol.* 171:2986-2993 (1989).

Rioux et al., "Vitamin B12 transport in *Escherichia coli* K12 does not require the btuE gene of the btuCED operon," *Mol. Gen. Genet.* 217:301-308 (1989).

Riviere et al., "Acetyl:succinate CoA-transferase in procyclic *Trypanosoma brucei*. Gene identification and role in carbohydrate metabolism." *J. Biol. Chem.* 279:45337-45346 (2004).

Roberts et al., "Cloning and expression of the gene cluster encoding key proteins involved in acetyl-CoA synthesis in *Clostridium thermoaceticum*: CO dehydrogenase, the corrinoid/Fe-S protein, and methyltransferase," *Proc. Natl. Acad. Sci. U.S.A.* 86(1):32-36 (1989).

Robinson et al., "Studies on Rat Brain Acyl-Coenzyme A Hydrolase (Short Chain)," *Biochem. Biophys. Res. Commun.* 71(4):959-965 (1976).

Roth et al., "Characterization of the cobalamin (vitamin B12) biosynthetic genes of *Salmonella typhimurium*," *J. Bacteriol.* 175:3303-3316 (1993).

Rother and Metcalf, "Anaerobic growth of *Methanosarcina acetivorans* C2A on carbon monoxide: an unusual way of life for a methanogenic archaeon," *Proc. Natl. Acad. Sci. U.S.A.* 101(48):16929-16934 (2004).

Rother et al., "Genetic and proteomic analyses of CO utilization by *Methanosarcina acetivorans*," *Arch. Microbiol.* 188(5):463-472 (2007).

Sakai et al, "Acetate and Ethanol Production from H2 and CO2 by *Morrella* sp. Using a Repeated Batch Culture," *J. Biosci. Bioeng.* 99:252-258 (2005).

Sauer et al., "Methanol:Coenzyme M methyltransferase from *Methanosarcina barkeri*. Purification, properties and encoding genes of the corrinoid protein MT1," *Eur. J. Biochem.* 243(3):670-677.

Sawers and Boxer, "Purification and properties of membrane-bound hydrogenase isoenzyme 1 from anaerobically grown *Escherichia coli* K12," *Eur. J. Biochem.* 156(2):265-275 (1986).

Sawers et al., "Characterization and physiological roles of membrane-bound hydrogenase isoenzymes from *Salmonella typhimurium*," *J. Bacteriol.* 168(1):398-404 (1986).

Sawers et al., "Differential expression of hydrogenase isoenzymes in *Escherichia coli* K-12: evidence for a third isoenzyme," *J. Bacteriol.* 164(3):1324-1331 (1985).

Sawers, "The hydrogenases and formate dehydrogenases of *Escherichia coli*," *Antonie Van Leeuwenhoek* 66(1-3):57-88 (1994).

Scherf and Buckel, "Purification and properties of an iron-sulfur and FAD-containing 4-hydroxybutyryl-CoA dehadratase/vinylacetyl-CoA $\Delta 3$-$\Delta 2$-isomerase from *Clostridium aminobutricum*," *Eur. J. Biochem.* 215:421-429 (1993).

Scherf et al, "Succinate-ethanol fermentation in *Clostridium kluyveri*: purification and characterisation of 4-hydroxybutyryl-CoA dehydratase/vinylacetyl-CoA $\Delta 3$-$\Delta A2$-isomerase," *Arch. Microbiol.* 161(3):239-245 (1994).

Scott, A.I., "Discovering nature's diverse pathways to vitamin B12: a 35-year odyssey," *J. Org. Chem.* 68:2529-2539 (2003).

Seedorf et al., "The genome of *Clostridium kluyveri*, a strict anaerobe with unique metabolic features," *Proc. Natl. Acad. Sci. U.S.A.* 105(6):2128-2133 (2008).

Sennett et al., "Transmembrane transport of cobalamin in prokaryotic and eukaryotic cells," *Ann. Rev. Biochem.* 50:1053-1086 (1981).

(56) References Cited

OTHER PUBLICATIONS

Seravalli et al., "Evidence that NiNi acetyl-CoA synthase is active and that the CuNi enzyme is not," *Biochemistry* 43(13):3944-3955 (2004).
Sheppard et al., "Purification and Properties of NADH-Dependent 5,10-Methylenetetrahydrofolate Reductase (MetF) from *Escherichia coli*," *J. Bacteriol.* 181(3):718-725 (1999).
Shimomura et al., "3-hydroxyisobutyryl-CoA hydrolase," *Methods Enzymol.* 324:229-240 (2000).
Shimomura et al., "Purification and partial characterization of 3-hydroxyisobutyryl-Coenzyme A hydrolase of rat liver," *J. Biol. Chem.* 269(19):14248-14253 (1994).
Sipma et al., "Microbial CO conversions with applications in synthesis gas purification and bio-desulfurization," *Crit. Rev. Biotechnol.* 26:41-65 (2006).
Skarstedt and Silverstein, "*Escherichia coli* acetate kinase mechanism studied by net initial rate, equilibrium, and independent isotopic exchange kinetics," *J. Biol. Chem.* 251:6775-6783 (1976).
Smith et al., "Purification and characteristics of a γ-glutamyl kinase involved in *Escherichia coli* proline biosynthesis," *J. Bacteriol.* 157:545-551 (1984).
Söhling and Gottschalk, "Molecular analysis of the anaerobic succinate degradation pathway in *Clostridium kluyveri*," *J. Bacteriol.* 178:871-880 (1996).
Song et al., "Structure, function, and mechanism of the phenylacetate pathway hot dog-fold thioesterase PaaI," *J. Biol. Chem.* 281(16):11028-11038 (2006).
St. Maurice et al., "Flavodoxin:quinone reductase (FqrB): a redox partner of pyruvate:ferredoxin oxidoreductase that reversibly couples pyruvate oxidation to NADPH production in *Helicobacter pylori* and *Campylobacter jejuni*," *J. Bacteriol.* 189:4764-4773 (2007).
Starai et al., "Acetate excretion during growth of *Salmonella enerica* on ethanolamine requires phosphotransacetylase (EutD) activity, and acetate recapture requires acetyl-CoA synthetase (Acs) and phosphotransacetylase (Pta) activities," *Microbiology* 151:3793-3801 (2005).
Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).
Steinbuchel and Schlegel, "A multifunctional fermentative alcohol dehydrogenase from the strict aerobe *Alcaligenes eutrophus*: purification and properties," *Eur J. Biochem.* 141:555-564 (1984).
Stols et al., "New vectors for co-expression of proteins: Structure of *Bacillus subtilis* ScoAB obtained by High-throughput protocols," *Protein Expr. Purif.* 53:396-403 (2007).
Strauss and Fuchs, "Enzymes of a novel autotrophic CO2 fixation pathway in the phototrophic bacterium *Chloroflexus aurantiacus*, the 3-hydroxypropionate cycle," *Eur. J. Biochem.* 215:633-643 (1993).
Suematsu et al., "Molecular cloning and functional expression of rat liver cytosolic acetyl-CoA hydrolase," *Eur. J. Biochem.* 268(9):2700-2709 (2001).
Sulzenbacher et al., "Crystal structure of *E. coli* alcohol dehydrogenase YqhD: evidence of a covalently modified NADP Coenzyme," *J. Mol. Biol.* 342(2):489-502 (2004).
Suzuki et al., "GriC and GriD Constitute a carboxylic acid reductase involved in grixazone biosynthesis in *Streptomyces griseus*," *J. Antibiot.* 60(6):380-387 (2007).
Suzuki, "Phosphotransacetylase of *Escherichia coli* B., activation by pyruvate and inhibition by NADH and certain nucleotides," *Biochem. Biophys. Acta* 191:559-569 (1969).
Svetlitchnyi et al., "A functional Ni-Ni-[4Fe-4S] cluster in the monomeric acetyl-CoA synthase from *Carboxydothermus hydrogenoformans*," *Proc. Natl. Acad. Sci. U.S.A.* 101(2):446-451 (2004).
Svetlitchnyi et al., "Two membrane-associated NiFeS-carbon monoxide dehydrogenases from the anaerobic carbon-monoxide-utilizing eubacterium *Carboxydothermus hydrogenoformans*," *J. Bacteriol.* 183(17):5134-5144 (2001).

Takahashi and Yamada, "Metabolic pathways for cytoxic and end product formation from glutamate- and aspartate-containing peptides by *Porphyromonas gingivalis*," *J. Bacteriol.* 182:4704-4710 (2000).
Takahashi-Abbe et al., "Biochemical and functional properties of a pyruvate formate-lyase (PFL)-activating system in *Streptococcus mutans*," *Oral Microbiol. Immunol.* 18:293-297 (2003).
Tallant and Krzycki, "Coenzyme M methylase activity of the 480-kilodalton corrinoid protein from *Methanosarcina barkeri*," *J. Bacteriol.* 178(5):1295-1301 (1996).
Tallant and Krzycki, "Methylthiol:Coenzyme M Methyltransferase from *Methanosarcina barkeri*, an enzyme of methanogenesis from dimethylsulfide and methylmercaptopropionate," *J. Bacteriol.* 179(22):6902-6911 (1997).
Tallant et al., "The MtsA subunit of the methylthiol:Coenzyme M methyltransferase of *Methanosarcina barkeri* catalyses both half-reactions of corrinoid-dependent dimethylsulfide: Coenzyme M methyl transfer," *J. Biol. Chem.* 276(6):4485-4493 (2001).
Tanaka et al., "Cloning and characterization of a human orthologue of testis-specific succinyl CoA: 3oxoo acid CoA transferase (Scot-t) cDNA," *Mol. Hum. Reprod.* 8:16-23 (2001).
Tani et al., "Thermostable NADP+-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).
Thauer, "Microbiology. A Fifth Pathway of Carbon Fixation," *Science* 318:1732-1733 (2007).
Toth et al., "The ald Gene, Encoding a Coenzyme A-Acylating Aldehyde Dehydrogenase, Distinguishes *Clostridium beijerinckii* and Two Other Solvent-Producing Clostridia from *Clostridium acetobutylicum*," *App. Environ. Microbiol.* 65(11):4973-4980 (1999).
Tseng et al., "Metabolic Engineering of *Escherichia coli* for Enhanced Production of (R)- and (S)-3-Hydroxybutyrate," *App. Environ. Microbiol.* 75(10):3137-3145 (2009).
Uttaro and Opperdoes, "Purification and characterisation of a novel isopropanol dehydrogenase from *Phytomonas* sp.," *Mol. Biochem. Parasitol.* 85:213-219 (1997).
Vamecq et al., "The microsomal dicarboxylyl-CoA synthetase," *Biochem. J.* 230(3):683-693 (1985).
van Grinsven et al., "Acetate:succinate CoA-transferase in the hydrogenosomes of *Trichomonas vaginalis*: identification and characterization," *J. Biol. Chem.* 283:1411-1418 (2008).
Vazquez et al., "Phosphtransbutyrylase expression in *Bacillus megaterium*," *Curr. Microbiol.* 42:345-349 (2001).
Venkitasubramanian et al. in *Biocatalysis in the Pharmaceutical and Biotechnology Industires*, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).
Vey et al., "Structural basis for glycyl radical formation by pyruvate formate-lyase activating enzyme," *Proc. Natl. Acad. Sci. U.S.A.* 105:16137-16141 (2008).
Walter et al., "Molecular characterization of two *Clostridium acetobutylicum* ATCC 824 butanol dehydrogenase isozyme genes," *J. Bacteriol.* 174(22):7149-7158 (1992).
Walter et al., "Sequence and arrangement of two genes of the butyrate-synthesis pathway of *Clostridium acetobutylicum* ATCC 824," *Gene* 134(1):107-111 (1993).
Wang et al, "Molecular cloning and functional identification of a novel phenylacetyl-CoA ligase gene from *Penicillium chrysogenum*," *Biochem. Biopyhs. Res. Commun.* 360(2):453-458 (2007).
Weidner and Sawers, "Molecular characterization of the Genes Encoding Pyruvate Formate-Lyase and Its Activating enzyme of *Clostridium pasteruianum*," *J. Bacteriol.* 178(8):2440-2444 (1996).
Westin et al., "The identification of a succinyl-CoA thioesterase suggests a novel pathway for succinate production in peroxisomes," *J. Biol. Chem.* 280(46):38125-38132 (2005).

(56) References Cited

OTHER PUBLICATIONS

Whitehead and Rabinowitz, "Cloning and expression in *Escherichia coli* of the gene for 10-formyltetrahydrofolate synthetase from *Clostridium acidiurici* ("Clostridium acidi-urici")," *J. Bacteriol.* 167:205-209 (1986).

Whitehead and Rabinowitz, "Nucleotide Sequence of the *Clostridium acidiurici* ("Clostridium acidi-urici") Gene for 10-Formyltetrahydrofolate Synthetase Shows Extensive Amino Acid Homology with the Trifunctional Enzyme C1-Tetrahydrofolate Synthase from *Saccharomyces cerevisiae*," *J. Bacteriol.* 170(7):3255-3261 (1988).

Wiesenborn et al., "Coenzyme A Transferase from *Clostridium acetobutylicum* ATCC 824 and Its Role in the Uptake of Acids," *Appl. Environ. Microbiol.* 55(2):323-329 (1989).

Winzer et al., "Differential regulation of two thiolase genes from *Clostridium acetobutylicum* DSM 792," *J. Mol. Microbiol. Biotechnol.* 2(4):531-541 (2000).

Wolff and Kenealy, "Purification and characterization of the oxygen-sensitive 4-hydroxybutanoate dehydrogenase from *Clostridium kluyveri*," *Protein Expr. Purif.* 6:206-212 (1995).

Wu et al., "Life in hot carbon monoxide: the complete genome sequence of *Carboxydothermus hydrogenoformans* Z-2901," *PLoS Genet.* 1(5):e65 (2005).

Wu et al., "Life in hot carbon monoxide: the complete genome sequence of *Carboxydothermus hydrogenoformans* Z-2901," *PLoS Genet.* 1(5):e65 (2005).

Yamamoto et al., "Purification and Properties of NADP-dependent Formate Dehydrogenase from *Clostridium thermoaceticum*, a tungsten-Selenium-Iron Protein," *J. Biol. Chem.* 258(3):1826-1832 (1983).

Zeiher and Randall, "Identification and characterization of Mitochondrial Acetyl-Coenzyme A Hydrolase from *Pisum sativum* L. Seedlings," *Plant. Physiol.* 94:20-27 (1990).

Zhang et al., "A new logic for DNA engineering using recombination in *Escherichia coli*," *Nat. Genet.* 20:123-128 (1998).

Zhou et al., "Engineering a native homoethanol pathway in *Escherichia coli* B for ethanol production," *Biotechnol. Lett.* 30:335-342 (2008).

Zhou et al., "The remarkable structural and functional organization of the eukaryotic pyruvate dehydrogenase complexes," *Proc. Natl. Acad. Sci. U.S.A.* 98:14802-14807 (2001).

Zhou et al., "Isolation, crystallization and preliminary X-ray analysis of a methanol-induced corrinoid protein from *Moorella thermoacetica*," *Acta. Crystallogr. Sect. F. Struct. Biol. Cryst. Commun.* 61(Pt.5):537-540 (2005).

Zhuang, et al., "The YbgC protein encoded by the ybgC gene of the tol-pal gene cluster of *Haemophilus influenzae* catalyzes acyl-Coenzyme A thioester hydrolysis," *FEBS Lett.* 516(1-3):161-163 (2002).

Genbank Accession No. AAA23199.2; GI No. 60592974 (Mar. 9, 2005).
Genbank Accession No. AAA27031.1; GI No. 153891 (Apr. 26, 1993).
Genbank Accession No. AAA27268.1; GI No. 154436 (Jul. 23, 1993).
Genbank Accession No. AAA27270.1; GI No. 154438 (Jul. 23, 1993).
Genbank Accession No. AAA34747.1; GI No. 171867 (Feb. 12, 2001).
Genbank Accession No. AAA80209; GI No. 687645 (Oct. 27, 1995).
Genbank Accession No. AACO2241.1; GI No. 2853226 (Jan. 30, 2001).
Genbank Accession No. AAC24333.2; GI No. 22711873 (Feb. 2, 2005).
Genbank Accession No. AAC45116; GI No. 1515466 (Apr. 5, 2002).
Genbank Accession No. AAC45117; GI No. 1515467 (Apr. 5, 2002).
Genbank Accession No. AAC45118; GI No. 1515468 (Apr. 5, 2002).
Genbank Accession No. AAC45119; GI No. 1515469 (Apr. 5, 2002).
Genbank Accession No. AAC45120; GI No. 1515470 (Apr. 5, 2002).
Genbank Accession No. AAC45121; GI No. 1498746 (Apr. 5, 2002).
Genbank Accession No. AAC45122; GI No. 1498747 (Apr. 5, 2002).
Genbank Accession No. AAC45123; GI No. 1498748 (Apr. 5, 2002).
Genbank Accession No. AAC45124; GI No. 1498749 (Apr. 5, 2002).
Genbank Accession No. AAC45125; GI No. 1498750 (Apr. 5, 2002).
Genbank Accession No. AAC45126; GI No. 1498751 (Apr. 5, 2002).
Genbank Accession No. AAC45217; GI No. 1684886 (Dec. 20, 2007).
Genbank Accession No. AAC73823.1; GI No. 1786949 (Oct. 25, 2010).
Genbank Accession No. AAK09379.1; GI No. 12958626 (Jan. 17, 2002).
Genbank Accession No. AAL20266.1; GI No. 16419860 (Feb. 23, 2009).
Genbank Accession No. AAM14586.1; GI No. 20162442 (Apr. 17, 2002).
Genbank Accession No. AAO26020.1; GI No. 28136195 (Jul. 30, 2003).
Genbank Accession No. AAP39869.1; GI No. 31322946 (Apr. 29, 2004).
Genbank Accession No. AAP42564.1; GI No. 31075384 (Jan. 24, 2007).
Genbank Accession No. AAP42565.1; GI No. 31075385 (Jan. 24, 2007).
Genbank Accession No. AAP42566.1; GI No. 31075386 (Jan. 24, 2007).
Genbank Accession No. AAR19757.1; GI No. 38425288 (Mar. 18, 2004).
Genbank Accession No. AAR91681.1; GI No. 40796035 (Mar. 9, 2004).
Genbank Accession No. AAS20429.1; GI No. 42561982 (Feb. 22, 2004).
Genbank Accession No. AAT66436; GI No. 49473535 (Apr. 26, 2006).
Genbank Accession No. AAV66076.1; GI No. 55818563 (Jun. 8, 2005).
Genbank Accession No. ABF82233.1; GI No. 106636093 (Aug. 2, 2007).
Genbank Accession No. ABF82234.1; GI No. 106636094 (Aug. 2, 2007).
Genbank Accession No. ABI83656.1; GI No. 114848891 (Jan. 3, 2007).
Genbank Accession No. ABS19624.1; GI No. 152002983 (Jul. 21, 2007).
Genbank Accession No. AP09256; GI No. 29895975 (Mar. 11, 2010).
Genbank Accession No. BAA03892.1; GI No. 425213 (Feb. 16, 2008).
Genbank Accession No. BAB12273.1; GI No. 9967138 (Mar. 18, 2005).
Genbank Accession No. BAB85476.1; GI No. 18857901 (Mar. 18, 2005).
Genbank Accession No. CAA15502; GI No. 3191970 (Jan. 13, 2009).
Genbank Accession No. CAA57199; GI No. 559392 (Mar. 22, 1995).
Genbank Accession No. CAA57200; GI No. 559393 (Mar. 22, 1995).
Genbank Accession No. CAA70873.1; GI No. 1770208 (Sep. 26, 1997).
Genbank Accession No. CAA74300.1; GI No. 3282044 (Nov. 14, 2006).
Genbank Accession No. CAB60035; GI No. 70910046 (May 13, 2008).
Genbank Accession No. CAC07932.1; GI No. 10046659 (Jun. 9, 2001).
Genbank Accession No. CAJ15517.1; GI No. 77019264 (Nov. 14, 2006).
Genbank Accession No. EDK33306.1; GI No. 146346770 (Feb. 21, 2008).
Genbank Accession No. EDK33307.1; GI No. 146346771 (Feb. 21, 2008).
Genbank Accession No. EDK33308.1; GI No. 146346772 (Feb. 21, 2008).
Genbank Accession No. EDK33309.1; GI No. 146346773 (Feb. 21, 2008).

(56) References Cited

OTHER PUBLICATIONS

Genbank Accession No. EDK33310.1; GI No. 146346774 (Feb. 21, 2008).
Genbank Accession No. EDK33311.1; GI No. 146346775 (Feb. 21, 2008).
Genbank Accession No. EDK35586.1; GI No. 146349050 (Feb. 21, 2008).
Genbank Accession No. L21902.1; GI No. 146348486 (Feb. 21, 2008).
Genbank Accession No. NP_000427; GI No. 4557817 (Nov. 3, 2010).
Genbank Accession No. NP_009538; GI No. 6319456 (Jun. 3, 2010).
Genbank Accession No. NP_009772.1; GI No. 6319690 (Aug. 17, 2010).
Genbank Accession No. NP_011760; GI No. 6321683 (Aug. 17, 2010).
Genbank Accession No. NP_012995.1; GI No. 6322922 (Jun. 3, 2010).
Genbank Accession No. NP_014032.1; GI No. 6323961 (Jun. 3, 2010).
Genbank Accession No. NP_014785; GI No. 6324716 (Aug. 17, 2010).
Genbank Accession No. NP_015297; GI No. 6325229 (Aug. 17, 2010).
Genbank Accession No. NP_070039.1; GI No. 11498810 (May 5, 2010).
Genbank Accession No. NP_071403; GI No. 11545841 (Nov. 4, 2010).
Genbank Accession No. NP_076417.2; GI No. 31982927 (Jun. 27, 2010).
Genbank Accession No. NP_084486.1; GI No. 21313520 (Jan. 31, 2010).
Genbank Accession No. NP_149242.1; GI No. 15004782 (Apr. 26, 2009).
Genbank Accession No. NP_149326.1; GI No. 15004866 (Apr. 26, 2009).
Genbank Accession No. NP_149327.1; GI No. 15004867 (Apr. 26, 2009).
Genbank Accession No. NP_149328.1; GI No. 15004868 (Apr. 26, 2009).
Genbank Accession No. NP_207955.1; GI No. 15645778 (Mar. 29, 2010).
Genbank Accession No. NP_343563.1; GI No. 15898958 (Jun. 9, 2010).
Genbank Accession No. NP_349314.1; GI No. 15895965 (Apr. 14, 2010).
Genbank Accession No. NP_349318.1; GI No. 15895969 (Apr. 14, 2010).
Genbank Accession No. NP_349476.1; GI No. 15896127 (Apr. 14, 2010).
Genbank Accession No. NP_349675; GI No. 15896326 (Apr. 14, 2010).
Genbank Accession No. NP_349676; GI No. 15896327 (Apr. 14, 2010).
Genbank Accession No. NP_349891.1; GI No. 15896542 (Apr. 14, 2010).
Genbank Accession No. NP_349892.1; GI No. 15896543 (Apr. 14, 2010).
Genbank Accession No. NP_378167.1; GI No. 15922498 (Jun. 9, 2010).
Genbank Accession No. NP_390902.2; GI No. 50812281 (Apr. 25, 2009).
Genbank Accession No. NP_391777; GI No. 16080949 (Mar. 31, 2010).
Genbank Accession No. NP_391778; GI No. 16080950 (Mar. 31, 2010).
Genbank Accession No. NP_414700.1; GI No. 16128151 (Oct. 25, 2010).
Genbank Accession No. NP_414777.1; GI No. 16128228 (Oct. 25, 2010).
Genbank Accession No. NP_414986; GI No. 16128437 (Oct. 25, 2010).
Genbank Accession No. NP_415027; GI No. 16128478 (Oct. 25, 2010).
Genbank Accession No. NP_415062.1; GI No. 16128513 (Oct. 25, 2010).
Genbank Accession No. NP_415129; GI No. 16128580 (Oct. 25, 2010).
Genbank Accession No. NP_415256.1; GI No. 16128703 (Oct. 25, 2010).
Genbank Accession No. NP_415264; GI No. 16128711 (Oct. 25, 2010).
Genbank Accession No. NP_415757.1; GI No. 16129202 (Oct. 25, 2010).
Genbank Accession No. NP_415768.1; GI No. 16129213 (Oct. 25, 2010).
Genbank Accession No. NP_415896.1; GI No. 16129339 (Oct. 25, 2010).
Genbank Accession No. NP_415905.1; GI No. 16129348 (Oct. 25, 2010).
Genbank Accession No. NP_415911.1; GI No. 16129354 (Oct. 25, 2010).
Genbank Accession No. NP_415912.1; GI No. 16129355 (Oct. 25, 2010).
Genbank Accession No. NP_415914; GI No. 16129357 (Oct. 25, 2010).
Genbank Accession No. NP_416224.1; GI No. 16129665 (Oct. 25, 2010).
Genbank Accession No. NP_416226.1; GI No. 16129667 (Oct. 25, 2010).
Genbank Accession No. NP_416495.1; GI No. 16129932 (Oct. 25, 2010).
Genbank Accession No. NP_416496.1; GI No. 16129933 (Oct. 25, 2010).
Genbank Accession No. NP_416497.1; GI No. 16129934 (Oct. 25, 2010).
Genbank Accession No. NP_416728; GI No. 16130161 (Oct. 25, 2010).
Genbank Accession No. NP_416799.1; GI No. 16130231 (Oct. 25, 2010).
Genbank Accession No. NP_416800.1; GI No. 16130232 (Oct. 25, 2010).
Genbank Accession No. NP_416976; GI No. 90111444 (Oct. 25, 2010).
Genbank Accession No. NP_416977; GI No. 16130407 (Oct. 25, 2010).
Genbank Accession No. NP_416978; GI No. 90111445 (Oct. 25, 2010).
Genbank Accession No. NP_416979; GI No. 16130409 (Oct. 25, 2010).
Genbank Accession No. NP_416980 ; GI No. 16130410 (Oct. 25, 2010).
Genbank Accession No. NP_416981; GI No. 16130411 (Oct. 25, 2010).
Genbank Accession No. NP_416982; GI No. 16130412 (Oct. 25, 2010).
Genbank Accession No. NP_416983; GI No. 16130413 (Oct. 25, 2010).
Genbank Accession No. NP_416984; GI No. 16130414 (Oct. 25, 2010).
Genbank Accession No. NP_416985; GI No. 90111446 (Oct. 25, 2010).
Genbank Accession No. NP_416986; GI No. 90111447 (Oct. 25, 2010).
Genbank Accession No. NP_417192; GI No. 16130619 (Oct. 25, 2010).
Genbank Accession No. NP_417197; GI No. 16130624 (Oct. 25, 2010).
Genbank Accession No. NP_417198; GI No. 16130625 (Oct. 25, 2010).

(56) References Cited

OTHER PUBLICATIONS

Genbank Accession No. NP_417199; GI No. 16130626 (Oct. 25, 2010).
Genbank Accession No. NP_417200; GI No. 16130627 (Oct. 25, 2010).
Genbank Accession No. NP_417201; GI No. 16130628 (Oct. 25, 2010).
Genbank Accession No. NP_417202; GI No. 16130629 (Oct. 25, 2010).
Genbank Accession No. NP_417203; GI No. 16130630 (Oct. 25, 2010).
Genbank Accession No. NP_417204; GI No. 16130631 (Oct. 25, 2010).
Genbank Accession No. NP_417205; GI No. 16130632 (Oct. 25, 2010).
Genbank Accession No. NP_417206; GI No. 16130633 (Oct. 25, 2010).
Genbank Accession No. NP_417207; GI No. 16130634 (Oct. 25, 2010).
Genbank Accession No. NP_417208; GI No. 16130635 (Oct. 25, 2010).
Genbank Accession No. NP_417209; GI No. 16130636 (Oct. 25, 2010).
Genbank Accession No. NP_417210; GI No. 226524740 (Oct. 25, 2010).
Genbank Accession No. NP_417478.1; GI No. 16130903 (Oct. 25, 2010).
Genbank Accession No. NP_417479.1; GI No. 16130904 (Oct. 25, 2010).
Genbank Accession No. NP_417484.1 GI No. 16130909 (Oct. 25, 2010).
Genbank Accession No. NP_417827.1; GI No. 16131246 (Oct. 25, 2010).
Genbank Accession No. NP_418376.1; GI No. 16131779 (Oct. 25, 2010).
Genbank Accession No. NP_418401.1; GI No. 16131804 (Oct. 25, 2010).
Genbank Accession No. NP_459635.1; GI No. 16764020 (Oct. 1, 2010).
Genbank Accession No. NP_459679.1; GI No. 16764064 (Oct. 1, 2010).
Genbank Accession No. NP_460306.1; GI No. 16764691 (Oct. 1, 2010).
Genbank Accession No. NP_460308.1; GI No. 16764693 (Oct. 1, 2010).
Genbank Accession No. NP_460961.1; GI No. 16765346 (Oct. 1, 2010).
Genbank Accession No. NP_460963.1; GI No. 16765348 (Oct. 1, 2010).
Genbank Accession No. NP_460969.1; GI No. 16765354 (Oct. 1, 2010).
Genbank Accession No. NP_460970.1; GI No. 16765355 (Oct. 1, 2010).
Genbank Accession No. NP_460971.1; GI No. 16765356 (Oct. 1, 2010).
Genbank Accession No. NP_460972.1; GI No. 16765357 (Oct. 1, 2010).
Genbank Accession No. NP_460973.1; GI No. 16765358 (Oct. 1, 2010).
Genbank Accession No. NP_460974.1; GI No. 16765359 (Oct. 1, 2010).
Genbank Accession No. NP_460975.1; GI No. 16765360 (Oct. 1, 2010).
Genbank Accession No. NP_460976.1; GI No. 16765361 (Oct. 1, 2010).
Genbank Accession No. NP_460977.1; GI No. 16765362 (Oct. 1, 2010).
Genbank Accession No. NP_460978.1; GI No. 16765363 (Oct. 1, 2010).
Genbank Accession No. NP_460980.1; GI No. 16765365 (Oct. 1, 2010).
Genbank Accession No. NP_462380.1; GI No. 16766765 (Oct. 1, 2010).
Genbank Accession No. NP_560604.1; GI No. 18313937 (Jun. 15, 2010).
Genbank Accession No. NP_570103.1; GI No. 18543355 (Nov. 10, 2010).
Genbank Accession No. NP_570112; GI No. 51036669 (Nov. 10, 2010).
Genbank Accession No. NP_602656.1; GI No. 19705161 (Jul. 28, 2010).
Genbank Accession No. NP_602657.1; GI No. 19705162 (Jul. 28, 2010).
Genbank Accession No. NP_603179.1; GI No. 19703617 (Jul. 28, 2010).
Genbank Accession No. NP_603180.1; GI No. 19703618 (Jul. 28, 2010).
Genbank Accession No. NP_615421; GI No. 20089346 (Jun. 29, 2010).
Genbank Accession No. NP_615422; GI No. 20089347 (Jun. 29, 2010).
Genbank Accession No. NP_615961; GI No. 20089886 (Jun. 29, 2010).
Genbank Accession No. NP_615962; GI No. 20089887 (Jun. 29, 2010).
Genbank Accession No. NP_615963; GI No. 20089888 (Jun. 29, 2010).
Genbank Accession No. NP_615964; GI No. 20089889 (Jun. 29, 2010).
Genbank Accession No. NP_615965; GI No. 20089890 (Jun. 29, 2010).
Genbank Accession No. NP_615966; GI No. 20089891 (Jun. 29, 2010).
Genbank Accession No. NP_616548; GI No. 20090473 (Jun. 29, 2010).
Genbank Accession No. NP_616549; GI No. 20090474 (Jun. 29, 2010).
Genbank Accession No. NP_616550; GI No. 20090475 (Jun. 29, 2010).
Genbank Accession No. NP_618731; GI No. 20092656 (Jun. 29, 2010).
Genbank Accession No. NP_618732; GI No. 20092657 (Jun. 29, 2010).
Genbank Accession No. NP_618733; GI No. 20092658 (Jun. 29, 2010).
Genbank Accession No. NP_618734; GI No. 20092659 (Jun. 29, 2010).
Genbank Accession No. NP_618735; GI No. 20092660 (Jun. 29, 2010).
Genbank Accession No. NP_618736; GI No. 20092661 (Jun. 29, 2010).
Genbank Accession No. NP_619241; GI No. 20093166 (Jun. 29, 2010).
Genbank Accession No. NP_619253; GI No. 20093178 (Jun. 29, 2010).
Genbank Accession No. NP_619254; GI No. 20093179 (Jun. 29, 2010).
Genbank Accession No. NP_622378.1; GI No. 20807207 (May 14, 2010).
Genbank Accession No. NP_622379.1; GI No. 20807208 (May 14, 2010).
Genbank Accession No. NP_745426.1; GI No. 26990001 (Jun. 29, 2010).
Genbank Accession No. NP_745427.1; GI No. 26990002 (Jun. 29, 2010).
Genbank Accession No. NP_904963.1; GI No. 34540484 (Jun. 29, 2010).
Genbank Accession No. NP_905281.1; GI No. 34540802 (Jun. 29, 2010).
Genbank Accession No. NP_905290.1; GI No. 34540811 (Jun. 29, 2010).

(56) References Cited

OTHER PUBLICATIONS

Genbank Accession No. NP_959974.1; GI No. 41407138 (May 12, 2010).
Genbank Accession No. NP_961833.1; GI No. 41408997 (May 12, 2010).
Genbank Accession No. P13419.1; GI No. 120562 (Aug. 10, 2010).
Genbank Accession No. P14941.1; GI No. 113443 (Nov. 2, 2010).
Genbank Accession No. P28817.2; GI No. 2506374 (Nov. 2, 2010).
Genbank Accession No. P31570.1; GI No. 399274 (Aug. 10, 2010).
Genbank Accession No. P38942.2; GI No. 1705614 (Feb. 5, 2008).
Genbank Accession No. P38946.1; GI No. 729048 (Aug. 10, 2010).
Genbank Accession No. P38947.1; GI No. 172046062 (Nov. 2, 2010).
Genbank Accession No. P40976.3; GI No. 13124791 (Aug. 10, 2010).
Genbank Accession No. P50113.1; GI No. 1708896 (Nov. 2, 2010).
Genbank Accession No. P76458.1; GI No. 2492990 (Aug. 10, 2010).
Genbank Accession No. P76459.1; GI No. 2492994 (Aug. 10, 2010).
Genbank Accession No. P77445; GI No. 2498347 (Nov. 2, 2010).
Genbank Accession No. Q05600.1; GI No. 543942 (Aug. 10, 2010).
Genbank Accession No. Q10474.1; GI No. 1723561 (Aug. 10, 2010).
Genbank Accession No. Q5XIE6.2; GI No. 146324906 (Oct. 5, 2010).
Genbank Accession No. Q6NVY1.2; GI No. 146324905 (Oct. 5, 2010).
Genbank Accession No. Q94B07; GI No. 75249805 (Oct. 31, 2006).
Genbank Accession No. Q97II1; GI No. 20137415 (Oct. 5, 2010).
Genbank Accession No. XP_001330176; GI No. 123975034 (Nov. 1, 2008).
Genbank Accession No. XP_636931.1; GI No. 66806417 (Jan. 29, 2010).
Genbank Accession No. XP_828352; GI No. 71754875 (May 15, 2008).
Genbank Accession No. YP_001190490; GI No. 146303174 (Aug. 10, 2010).
Genbank Accession No. YP_001190500; GI No. 146303184 (Aug. 10, 2010).
Genbank Accession No. YP_001190808.1; GI No. 146303492 (Aug. 10, 2010).
Genbank Accession No. YP_001191305; GI No. 146303989 (Aug. 10, 2010).
Genbank Accession No. YP_001191403; GI No. 146304087 (Aug. 10, 2010).
Genbank Accession No. YP_001191504; GI No. 146304188 (Aug. 10, 2010).
Genbank Accession No. YP_001191505; GI No. 146304189 (Aug. 10, 2010).
Genbank Accession No. YP_001192057; GI No. 146304741 (Aug. 10, 2010).
Genbank Accession No. YP_001310906.1; GI No. 150018652 (Apr. 1, 2010).
Genbank Accession No. YP_001396399; GI No. 153955634 (May 6, 2010).
Genbank Accession No. YP_001433009.1; GI No. 156742880 (Nov. 2, 2010).
Genbank Accession No. YP_001482096.1; GI No. 157414840 (Apr. 27, 2010).
Genbank Accession No. YP_001822177.1; GI No. 182434458 (Apr. 14, 2010).
Genbank Accession No. YP_001825755.1; GI No. 182438036 (Apr. 14, 2010).
Genbank Accession No. YP_001825756.1; GI No. 182438037 (Apr. 14, 2010).
Genbank Accession No. YP_001828302.1; GI No. 182440583 (Apr. 14, 2010).
Genbank Accession No. YP_001850220.1; GI No. 183981929 (May 12, 2010).
Genbank Accession No. YP_001850422.1; GI No. 183982131 (May 12, 2010).
Genbank Accession No. YP_001851230.1; GI No. 183982939 (May 12, 2010).
Genbank Accession No. YP_047869.1; GI No. 50086359 (May 24, 2010).
Genbank Accession No. YP_118225.1; GI No. 54023983 (May 12, 2010).
Genbank Accession No. YP_120266.1; GI No. 54026024 (May 12, 2010).
Genbank Accession No. YP_135572.1; GI No. 55377722 (Jun. 8, 2010).
Genbank Accession No. YP_162971.1; GI No. 56552132 (Aug. 13, 2010).
Genbank Accession No. YP_256941.1; GI No. 70608071 (Aug. 9, 2010).
Genbank Accession No. YP_299391.1; GI No. 73539024 (Mar. 31, 2010).
Genbank Accession No. YP_304298; GI No. 73668283 (Jun. 18, 2010).
Genbank Accession No. YP_304299; GI No. 73668284 (Jun. 18, 2010).
Genbank Accession No. YP_304602; GI No. 73668587 (Jun. 18, 2010).
Genbank Accession No. YP_304611; GI No. 73668596 (Jun. 18, 2010).
Genbank Accession No. YP_304612; GI No. 73668597 (Jun. 18, 2010).
Genbank Accession No. YP_307081; GI No. 73671066 (Jun. 18, 2010).
Genbank Accession No. YP_307082; GI No. 73671067 (Jun. 18, 2010).
Genbank Accession No. YP_358957; GI No. 78044574 (Mar. 31, 2010).
Genbank Accession No. YP_358958; GI No. 78045112 (Mar. 31, 2010).
Genbank Accession No. YP_359585.1; GI No. 78044572 (Mar. 31, 2010).
Genbank Accession No. YP_359586.1; GI No. 78044500 (Mar. 31, 2010).
Genbank Accession No. YP_359587.1; GI No. 78044647 (Mar. 31, 2010).
Genbank Accession No. YP_360059; GI No. 78044249 (Mar. 31, 2010).
Genbank Accession No. YP_360060; GI No. 78042742 (Mar. 31, 2010).
Genbank Accession No. YP_360061; GI No. 78043584 (Mar. 31, 2010).
Genbank Accession No. YP_360062; GI No. 78044449 (Mar. 31, 2010).
Genbank Accession No. YP_360063; GI No. 78044060 (Mar. 31, 2010).
Genbank Accession No. YP_360064; GI No. 78042962 (Mar. 31, 2010).
Genbank Accession No. YP_360065; GI No. 78044202 (Mar. 31, 2010).
Genbank Accession No. YP_360071.1; GI No. 78044792 (Mar. 31, 2010).
Genbank Accession No. YP_360644; GI No. 78043418 (Mar. 31, 2010).
Genbank Accession No. YP_360645; GI No. 78044791 (Mar. 31, 2010).
Genbank Accession No. YP_360646; GI No. 78044340 (Mar. 31, 2010).
Genbank Accession No. YP_360647; GI No. 78043871 (Mar. 31, 2010).
Genbank Accession No. YP_360648; GI No. 78044023 (Mar. 31, 2010).
Genbank Accession No. YP_360649; GI No. 78043124 (Mar. 31, 2010).
Genbank Accession No. YP_360650; GI No. 78043938 (Mar. 31, 2010).
Genbank Accession No. YP_360651; GI No. 78044700 (Mar. 31, 2010).

(56) References Cited

OTHER PUBLICATIONS

Genbank Accession No. YP_360652; GI No. 78043942 (Mar. 31, 2010).
Genbank Accession No. YP_360698.1; GI No. 78044829 (Mar. 31, 2010).
Genbank Accession No. YP_361182.1; GI No. 78045024 (Mar. 31, 2010).
Genbank Accession No. YP_428946.1; GI No. 83588937 (Apr. 1, 2010).
Genbank Accession No. YP_428991.1; GI No. 83588982 (Apr. 1, 2010).
Genbank Accession No. YP_429313; GI No. 83589304 (Apr. 1, 2010).
Genbank Accession No. YP_429314; GI No. 83589305 (Apr. 1, 2010).
Genbank Accession No. YP_429315; GI No. 83589306 (Apr. 1, 2010).
Genbank Accession No. YP_429316; GI No. 83589307 (Apr. 1, 2010).
Genbank Accession No. YP_429670; GI No. 83589661 (Apr. 1, 2010).
Genbank Accession No. YP_429671; GI No. 83589662 (Apr. 1, 2010).
Genbank Accession No. YP_429672; GI No. 83589663 (Apr. 4, 2006).
Genbank Accession No. YP_429673; GI No. 83589664 (Jul. 22, 2008).
Genbank Accession No. YP_429674; GI No. 83589665 (Apr. 1, 2010).
Genbank Accession No. YP_429675; GI No. 83589666 (Apr. 1, 2010).
Genbank Accession No. YP_429676; GI No. 83589667 (Apr. 1, 2010).
Genbank Accession No. YP_430050; GI No. 83590041 (Apr. 1, 2010).
Genbank Accession No. YP_430051; GI No. 83590042 (Apr. 1, 2010).
Genbank Accession No. YP_430052; GI No. 83590043 (Apr. 1, 2010).
Genbank Accession No. YP_430053; GI No. 83590044 (Apr. 1, 2010).
Genbank Accession No. YP_430054; GI No. 83590045 (Apr. 1, 2010).
Genbank Accession No. YP_430055; GI No. 83590046 (Apr. 1, 2010).
Genbank Accession No. YP_430056; GI No. 83590047 (Apr. 1, 2010).
Genbank Accession No. YP_430057; GI No. 83590048 (Apr. 1, 2010).
Genbank Accession No. YP_430058; GI No. 83590049 (Apr. 1, 2010).
Genbank Accession No. YP_430059; GI No. 83590050 (Apr. 1, 2010).
Genbank Accession No. YP_430060; GI No. 83590051 (Apr. 1, 2010).
Genbank Accession No. YP_430061; GI No. 83590052 (Apr. 1, 2010).
Genbank Accession No. YP_430065; GI No. 83590056 (Apr. 1, 2010).
Genbank Accession No. YP_430066; GI No. 83590057 (Apr. 1, 2010).
Genbank Accession No. YP_430305; GI No. 83590296 (Apr. 1, 2010).
Genbank Accession No. YP_430306; GI No. 83590297 (Apr. 1, 2010).
Genbank Accession No. YP_430307; GI No. 83590298 (Apr. 1, 2010).
Genbank Accession No. YP_430368.1; GI No. 83590359 (Apr. 1, 2010).
Genbank Accession No. YP_430562; GI No. 83590553 (Apr. 1, 2010).
Genbank Accession No. YP_430563; GI No. 83590554 (Apr. 1, 2010).
Genbank Accession No. YP_430564; GI No. 83590555 (Apr. 1, 2010).
Genbank Accession No. YP_430726; GI No. 83590717 (Apr. 1, 2010).
Genbank Accession No. YP_430727; GI No. 83590718 (Apr. 1, 2010).
Genbank Accession No. YP_430728; GI No. 83590719 (Apr. 1, 2010).
Genbank Accession No. YP_430729; GI No. 83590720 (Apr. 1, 2010).
Genbank Accession No. YP_430730; GI No. 83590721 (Apr. 1, 2010).
Genbank Accession No. YP_430731; GI No. 83590722 (Apr. 1, 2010).
Genbank Accession No. YP_430813; GI No. 83590804 (Apr. 1, 2010).
Genbank Accession No. YP_430935; GI No. 83590926 (Apr. 1, 2010).
Genbank Accession No. YP_430937; GI No. 83590928 (Apr. 1, 2010).
Genbank Accession No. YP_431007; GI No. 83590998 (Apr. 1, 2010).
Genbank Accession No. YP_431008; GI No. 83590999 (Apr. 1, 2010).
Genbank Accession No. YP_431009; GI No. 83591000 (Apr. 1, 2010).
Genbank Accession No. YP_431010; GI No. 83591001 (Apr. 1, 2010).
Genbank Accession No. YP_431011; GI No. 83591002 (Apr. 1, 2010).
Genbank Accession No. YP_431012; GI No. 83591003 (Apr. 1, 2010).
Genbank Accession No. YP_431013; GI No. 83591004 (Apr. 1, 2010).
Genbank Accession No. YP_431014; GI No. 83591005 (Apr. 1, 2010).
Genbank Accession No. YP_431015; GI No. 83591006 (Apr. 1, 2010).
Genbank Accession No. YP_431016; GI No. 83591007 (Apr. 1, 2010).
Genbank Accession No. YP_431017; GI No. 83591008 (Apr. 1, 2010).
Genbank Accession No. YP_431018; GI No. 83591009 (Apr. 1, 2010).
Genbank Accession No. YP_431019; GI No. 83591010 (Apr. 1, 2010).
Genbank Accession No. YP_431020; GI No. 83591011 (Apr. 1, 2010).
Genbank Accession No. YP_431021; GI No. 83591012 (Apr. 1, 2010).
Genbank Accession No. YP_431022; GI No. 83591013 (Apr. 1, 2010).
Genbank Accession No. YP_431023; GI No. 83591014 (Apr. 1, 2010).
Genbank Accession No. YP_431024; GI No. 83591015 (Apr. 1, 2010).
Genbank Accession No. YP_431142; GI No. 148283121 (Apr. 1, 2010).
Genbank Accession No. YP_431144; GI No. 83591135 (Apr. 1, 2010).
Genbank Accession No. YP_431175; GI No. 83591166 (Apr. 1, 2010).
Genbank Accession No. YP_627417; GI No. 108563101 (Apr. 27, 2010).
Genbank Accession No. YP_627418; GI No. 108563102 (Apr. 27, 2010).
Genbank Accession No. YP_726053.1; GI No. 113867564 (May 28, 2010).

(56) References Cited

OTHER PUBLICATIONS

Genbank Accession No. YP_846816.1; GI No. 116750129 (Apr. 1, 2010).
Genbank Accession No. YP_846817.1; GI No. 116750130 (Apr. 1, 2010).
Genbank Accession No. YP_846818.1; GI No. 116750131 (Apr. 1, 2010).
Genbank Accession No. YP_846819.1; GI No. 116750132 (Apr. 1, 2010).
Genbank Accession No. YP_886985.1; GI No. 118471293 (Mar. 31, 2010).
Genbank Accession No. YP_887275.1; GI No. 118473501 (Dec. 3, 2007).
Genbank Accession No. YP_889972.1; GI No. 118469671 (Mar. 31, 2010).
Genbank Accession No. YP_978699.1; GI No. 121638475 (May 13, 2010).
Genbank Accession No. YP_978898.1; GI No. 121638674 (May 13, 2010).
Genbank Accession No. ZP_01039179.1; GI No. 85708113 (Nov. 9, 2010).
Genbank Accession No. ZP_01626393.1; GI No. 119504313 (Nov. 9, 2010).
Genbank Accession No. ZP_04026660.1; GI No. 227979396 (Apr. 28, 2009).
Genbank Accession No. ZP_04027864.1; GI No. 227980601 (Apr. 28, 2009).
Genbank Accession No. ZP_05045132.1; GI No. 254431429 (Jun. 8, 2010).
Genbank Accession No. ZP_05390164.1; GI No. 255523193 (Nov. 10, 2010).
Genbank Accession No. ZP_05390341.1; GI No. 255523371 (Nov. 10, 2010).
Genbank Accession No. ZP_05390901.1; GI No. 255523938 (Nov. 10, 2010).
Genbank Accession No. ZP_05390930.1; GI No. 255523967 (Nov. 10, 2010).
Genbank Accession No. ZP_05391756.1; GI No. 255524806 (Nov. 10, 2010).
Genbank Accession No. ZP_05391913.1; GI No. 255524966 (Nov. 10, 2010).
Genbank Accession No. ZP_05392031.1; GI No. 255525086 (Nov. 10, 2010).
Genbank Accession No. ZP_05392150.1; GI No. 255525208 (Nov. 10, 2010).
Genbank Accession No. ZP_05392428.1; GI No. 255525491 (Nov. 10, 2010).
Genbank Accession No. ZP_05392429.1; GI No. 255525492 (Nov. 10, 2010).
Genbank Accession No. ZP_05392434.1; GI No. 255525497 (Nov. 10, 2010).
Genbank Accession No. ZP_05392944.1; GI No. 255526020 (Nov. 10, 2010).
Genbank Accession No. ZP_05392945.1; GI No. 255526021 (Nov. 10, 2010).
Genbank Accession No. ZP_05392946.1; GI No. 255526022 (Nov. 10, 2010).
Genbank Accession No. ZP_05392948.1; GI No. 255526024 (Nov. 10, 2010).
Genbank Accession No. ZP_05392952.1; GI No. 255526028 (Nov. 10, 2010).
Genbank Accession No. ZP_05392953.1; GI No. 255526029 (Nov. 10, 2010).
Genbank Accession No. ZP_05392954.1; GI No. 255526030 (Nov. 10, 2010).
Genbank Accession No. ZP_05392955.1; GI No. 255526031 (Nov. 10, 2010).
Genbank Accession No. ZP_05392956.1; GI No. 255526032 (Nov. 10, 2010).
Genbank Accession No. ZP_05392958.1; GI No. 255526034 (Nov. 10, 2010).
Genbank Accession No. ZP_05394380.1; GI No. 255527512 (Nov. 10, 2010).
Genbank Accession No. ZP_05394384.1; GI No. 255527516 (Nov. 10, 2010).
Genbank Accession No. ZP_05394386.1; GI No. 255527518 (Nov. 10, 2010).
Genbank Accession No. ZP_05394396.1; GI No. 255527529 (Nov. 10, 2010).
Genbank Accession No. ZP_05394397.1; GI No. 255527530 (Nov. 10, 2010).

* cited by examiner

MICROORGANISMS AND METHODS FOR CONVERSION OF SYNGAS AND OTHER CARBON SOURCES TO USEFUL PRODUCTS

This application is a division of U.S. Ser. No. 13/371,278 filed Feb. 10, 2012, now U.S. Pat. No. 8,470,566, which is a continuation of U.S. Ser. No. 12/639,977 filed Dec. 16, 2009, now U.S. Pat. No. 8,129,155, which is a continuation-in-part of PCT Application Number PCT/US09/50757, filed Jul. 15, 2009 and further claims the benefit of priority of U.S. Provisional Application Ser. No. 61/138,108, filed Dec. 16, 2008, each of which the entire contents are incorporated herein by this reference.

BACKGROUND OF THE INVENTION

The present invention relates generally to biosynthetic processes and organisms capable of converting carbohydrates, methanol, synthesis gas and other gaseous carbon sources into higher-value chemicals.

Increasing the flexibility of cheap and readily available feedstocks and minimizing the environmental impact of chemical production are beneficial for a sustainable chemical industry. Feedstock flexibility relies on the introduction of methods that can access and use a wide range of materials as primary feedstocks for chemical manufacturing.

Isopropanol (IPA) is a colorless, flammable liquid that mixes completely with most solvents, including water. The largest use for IPA is as a solvent, including its well known yet small use as "rubbing alcohol," which is a mixture of IPA and water. As a solvent, IPA is found in many everyday products such as paints, lacquers, thinners, inks, adhesives, general-purpose cleaners, disinfectants, cosmetics, toiletries, de-icers, and pharmaceuticals. Low-grade IPA is also used in motor oils. The second largest use is as a chemical intermediate for the production of isopropylamines (e.g. in agricultural products), isopropylethers, and isopropyl esters.

Isopropanol is manufactured by two petrochemical routes. The predominant process entails the hydration of propylene either with or without sulfuric acid catalysis. Secondarily, IPA is produced via hydrogenation of acetone, which is a by-product formed in the production of phenol and propylene oxide. High-priced propylene is currently driving costs up and margins down throughout the chemical industry motivating the need for an expanded range of low cost feedstocks.

4-hydroxybutanoic acid (4-hydroxybutanoate, 4-hydroxybutyrate, 4-HB) is a 4-carbon carboxylic acid that has industrial potential as a building block for various commodity and specialty chemicals. In particular, 4-HB has the potential to serve as a new entry point into the 1,4-butanediol family of chemicals, which includes solvents, resins, polymer precursors, and specialty chemicals.

BDO is a valuable chemical for the production of high performance polymers, solvents, and fine chemicals. It is the basis for producing other high value chemicals such as tetrahydrofuran (THF) and gamma-butyrolactone (GBL). Uses of BDO include (1) polymers, (2) THF derivatives, and (3) GBL derivatives. In the case of polymers, BDO is a co-monomer for polybutylene terephthalate (PBT) production. PBT is a medium performance engineering thermoplastic made by companies such as DuPont and General Electric finding use in automotive, electrical, water systems, and small appliance applications. When converted to THF, and subsequently to polytetramethylene ether glycol (PTMEG), the Spandex and Lycra fiber and apparel industries are added to the markets served. PTMEG is also combined with BDO in the production of specialty polyester ethers (COPE). COPEs are high modulus elastomers with excellent mechanical properties and oil/environmental resistance, allowing them to operate at high and low temperature extremes. PTMEG and BDO also make thermoplastic polyurethanes processed on standard thermoplastic extrusion, calendaring, and molding equipment, and are characterized by their outstanding toughness and abrasion resistance. The GBL produced from BDO provides the feedstock for making pyrrolidones, as well as serving agrochemical market applications itself. The pyrrolidones are used as high performance solvents for extraction processes of increasing use in the electronics industry as well as use in pharmaceutical production.

BDO is produced by two main petrochemical routes with a few additional routes also in commercial operation. One route involves reacting acetylene with formaldehyde, followed by hydrogenation. More recently BDO processes involving butane or butadiene oxidation to maleic anhydride, followed by hydrogenation have been introduced. BDO is used almost exclusively as an intermediate to synthesize other chemicals and polymers.

Synthesis gas (syngas) is a mixture of primarily $H_2$ and CO that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as, for example, 0.5:1-3:1 $H_2$/CO mixture. Steam is sometimes added to increase the hydrogen content, typically with increased CO, production through the water gas shift reaction. Methanol is most commonly produced industrially from the syngas components, CO and $H_2$, via catalysis Today, coal is the main substrate used for industrial production of syngas, which is usually used for heating and power and as a feedstock for Fischer-Tropsch synthesis of methanol and liquid hydrocarbons. Many large chemical and energy companies employ coal gasification processes on large scale and there is experience in the industry using this technology.

Overall, technology now exists for cost-effective production of syngas from a plethora of materials, including coal, biomass, wastes, polymers, and the like, at virtually any location in the world. Biomass gasification technologies are being practiced commercially, particularly for heat and energy generation.

Despite the availability of organisms that utilize syngas, such organisms are generally poorly characterized and are not well-suited for commercial development. For example, *Clostridium* and related bacteria are strict anaerobes that are intolerant to high concentrations of certain products such as butanol, thus limiting titers and commercialization potential. The *Clostridia* also produce multiple products, which presents separations issues in isolating a desired product. Finally, development of facile genetic tools to manipulate clostridial genes is in its infancy, therefore, they are not currently amenable to rapid genetic engineering to improve yield or production characteristics of a desired product.

Thus, there exists a need to develop microorganisms and methods of their use to utilize carbohydrates, methanol, syngas and/or other gaseous carbon sources for the production of desired chemicals and fuels. More specifically, there exists a need to develop microorganisms for carbohydrate, methanol, and syngas utilization that also have existing and efficient genetic tools to enable their rapid engineering to produce valuable products at useful rates and quantities. The present invention satisfies this need and provides related advantages as well.

SUMMARY OF THE INVENTION

In some aspects, the present invention provides a non-naturally occurring microbial organism having an isopropanol pathway that includes at least one exogenous nucleic acid encoding an isopropanol pathway enzyme expressed in a sufficient amount to produce isopropanol. The isopropanol pathway enzyme includes a succinyl-CoA:3-ketoacid-CoA transferase.

In other aspects, the present invention provides a non-naturally occurring microbial organism having a 4-hydroxybutyrate pathway that includes at least one exogenous nucleic acid encoding an 4-hydroxybutyrate pathway enzyme expressed in a sufficient amount to produce 4-hydroxybutryate. The 4-hydroxybutyrate pathway enzyme includes an acetoacetyl-CoA thiolase, a 3-hydroxybutyryl-CoA dehydrogenase, a crotonase, a crotonyl-CoA hydratase, a 4-hydroxybutyryl-CoA transferase, a 4-hydroxybutyryl-CoA hydrolase, a 4-hydroxybutyryl-CoA synthetase, a phosphotrans-4-hydroxybutyrylase, and a 4-hydroxybutyrate kinase.

In still other aspects, the present invention provides a non-naturally occurring microbial organism having a 1,4-butanediol pathway that includes at least one exogenous nucleic acid encoding a 1,4-butanediol pathway enzyme expressed in a sufficient amount to produce 1,4-butanediol. The 1,4-butanediol pathway enzyme includes an acetoacetyl-CoA thiolase, a 3-Hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), a 1,4-butanediol dehydrogenase, a 4-hydroxybutyryl-CoA transferase, a 4-hydroxybutyryl-CoA hydrolase, a 4-hydroxybutyryl-CoA synthetase, a phosphotrans-4-hydroxybutyrylase, a 4-hydroxybutyrate kinase, and a 4-hydroxybutyrate reductase. Such an organism also includes an acetyl-CoA pathway having at least one exogenous nucleic acid encoding an acetyl-CoA pathway enzyme expressed in a sufficient amount to produce acetyl-CoA. The acetyl-CoA pathway enzyme includes a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In yet other aspects, the present invention provides a non-naturally occurring microbial organism having a 1,4-butanediol pathway that includes at least one exogenous nucleic acid encoding a 1,4-butanediol pathway enzyme expressed in a sufficient amount to produce 1,4-butanediol. The 1,4-butanediol pathway enzyme includes an acetoacetyl-CoA thiolase, a 3-Hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), a 1,4-butanediol dehydrogenase, a 4-hydroxybutyryl-CoA transferase, a 4-hydroxybutyryl-CoA hydrolase, a 4-hydroxybutyryl-CoA synthetase, a phosphotrans-4-hydroxybutyrylase, a 4-hydroxybutyrate kinase, and a 4-hydroxybutyrate reductase. Such an organism also includes an acetyl-CoA pathway having at least one exogenous nucleic acid encoding an acetyl-CoA pathway enzyme expressed in a sufficient amount to produce acetyl-CoA. The acetyl-CoA pathway enzyme includes an acetyl-CoA synthase, a formate dehydrogenase, a formyltetrahydrofolate synthetase, a methenyltetrahydrofolate cyclohydrolase, a methylenetetrahydrofolate dehydrogenase, and a methylenetetrahydrofolate reductase.

In still further aspects, the present invention provides a non-naturally occurring microbial organism having an isopropanol pathway that includes at least one exogenous nucleic acid encoding an isopropanol pathway enzyme expressed in a sufficient amount to produce isopropanol. The isopropanol pathway enzyme includes an acetoacetyl-CoA thiolase, an acetoacetyl-CoA transferase, an acetoacetyl-CoA hydrolase, an acetoacetyl-CoA synthetase, a phosphotransacetoacetylase, an acetoacetate kinase, an acetoacetate decarboxylase, and an isopropanol dehydrogenase. Such an organism also includes at least one exogenous nucleic acid encoding an acetyl-CoA enzyme expressed in a sufficient amount to produce acetyl-CoA. The acetyl-CoA pathway enzyme includes a methanol methyl transferase, a corrinoid protein, a methyltetrahydro-folate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In still further aspects, the present invention provides a method for producing isopropanol that includes culturing a non-naturally occurring microbial organism having an isopropanol pathway. The pathway includes at least one exogenous nucleic acid encoding an isopropanol pathway enzyme expressed in a sufficient amount to produce isopropanol under conditions and for a sufficient period of time to produce isopropanol. The isopropanol pathway includes a succinyl-CoA:3-ketoacid-CoA transferase.

In yet still further aspects, the present invention provides a method for producing 4-hydroxybutyrate that includes culturing a non-naturally occurring microbial organism having an 4-hydroxybutyrate pathway. The pathway includes at least one exogenous nucleic acid encoding an 4-hydroxybutyrate pathway enzyme expressed in a sufficient amount to produce 4-hydroxybutyrate under conditions and for a sufficient period of time to produce 4-hydroxybutyrate. The 4-hydroxybutyrate pathway includes an acetoacetyl-CoA thiolase, a 3-hydroxybutyryl-CoA dehydrogenase, a crotonase, a crotonyl-CoA hydratase, a 4-hydroxybutyryl-CoA transferase, a 4-hydroxybutyryl-CoA hydrolase, a 4-hydroxybutyryl-CoA synthetase, a phosphotrans-4-hydroxybutyrylase, and a 4-hydroxybutyrate kinase.

In still other aspects, the present invention provides a method for producing 1,4-butanediol that includes culturing a non-naturally occurring microbial organism having an 1,4-butanediol pathway. The pathway includes at least one exogenous nucleic acid encoding an 1,4-butanediol pathway enzyme expressed in a sufficient amount to produce 1,4-butanediol under conditions and for a sufficient period of time to produce 1,4-butanediol. The 1,4-butanediol pathway includes an acetoacetyl-CoA thiolase, a 3-hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), a 1,4-butanediol dehydrogenase, a 4-hydroxybutyryl-CoA transferase, a 4-hydroxybutyryl-CoA hydrolase, a 4-hydroxybutyryl-CoA synthetase, a phosphotrans-4-hydroxybutyrylase, a 4-hydroxybutyrate kinase, and a 4-hydroxybutyrate reductase. Such an organism also includes an acetyl-CoA pathway comprising at least one exogenous nucleic acid encoding an acetyl-CoA pathway enzyme expressed in a sufficient amount to produce acetyl-CoA. The acetyl-CoA pathway enzyme includes a corrinoid protein, a methyltetrahydro-folate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

Finally, in some aspects, the present invention provides a method for producing 1,4-butanediol that includes culturing a non-naturally occurring microbial organism having an 1,4-butanediol pathway. The pathway includes at least one exogenous nucleic acid encoding an 1,4-butanediol pathway enzyme expressed in a sufficient amount to produce 1,4-butanediol under conditions and for a sufficient period of time to produce 1,4-butanediol. The 1,4-butanediol pathway includes an acetoacetyl-CoA thiolase, a 3-hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), a 1,4-butanediol dehydrogenase, a 4-hydroxybutyryl-CoA transferase, a 4-hydroxybutyryl-CoA hydrolase, a 4-hydroxybutyryl-CoA synthetase, a phosphotrans-4-hydroxybutyrylase, a 4-hydroxybutyrate kinase, and a 4-hydroxybutyrate reductase. Such an organism also includes an acetyl-CoA pathway having at least one exogenous nucleic acid encoding an acetyl-CoA pathway enzyme expressed in a sufficient amount to produce acetyl-CoA. The acetyl-CoA pathway enzyme includes an acetyl-CoA synthase, a formate dehydrogenase, a formyltetrahydrofolate synthetase, a methenyltetrahydrofolate cyclohydrolase, a methylenetetrahydrofolate dehydrogenase, and a methylenetetrahydrofolate reductase.

BRIEF DESCRIPTION OF THE DRAWINGS

In FIGS. 2A-D, the specific enzymatic transformations that can be engineered into a production host are numbered. Abbreviations: 10FTHF: 10-formyltetrahydrofolate, 5MTHF: 5-methyltetrahydrofolate, ACTP: acetyl phosphate, CFeSp: corrinoid iron sulfur protein, FOR: formate, MeOH: methanol, METHF: methyltetrahydrofolate, MLTHF: metheneyltetrahydrofolate, THF: tetrahydrofolate.

In FIGS. 3A-C the specific enzymatic transformations that can be engineered into a production host are numbered. Abbreviations: 10FTHF: 10-formyltetrahydrofolate, 5MTHF: 5-methyltetrahydrofolate, ACTP: acetyl phosphate, CFeSp: corrinoid iron sulfur protein, FOR: formate, MeOH: methanol, METHF: methyltetrahydrofolate, MLTHF: metheneyltetrahydrofolate, THF: tetrahydrofolate.

In FIGS. 8A-C, several enzymatic transformations that can be engineered into a production host are numbered.

DETAILED DESCRIPTION OF THE INVENTION

Figure 1:
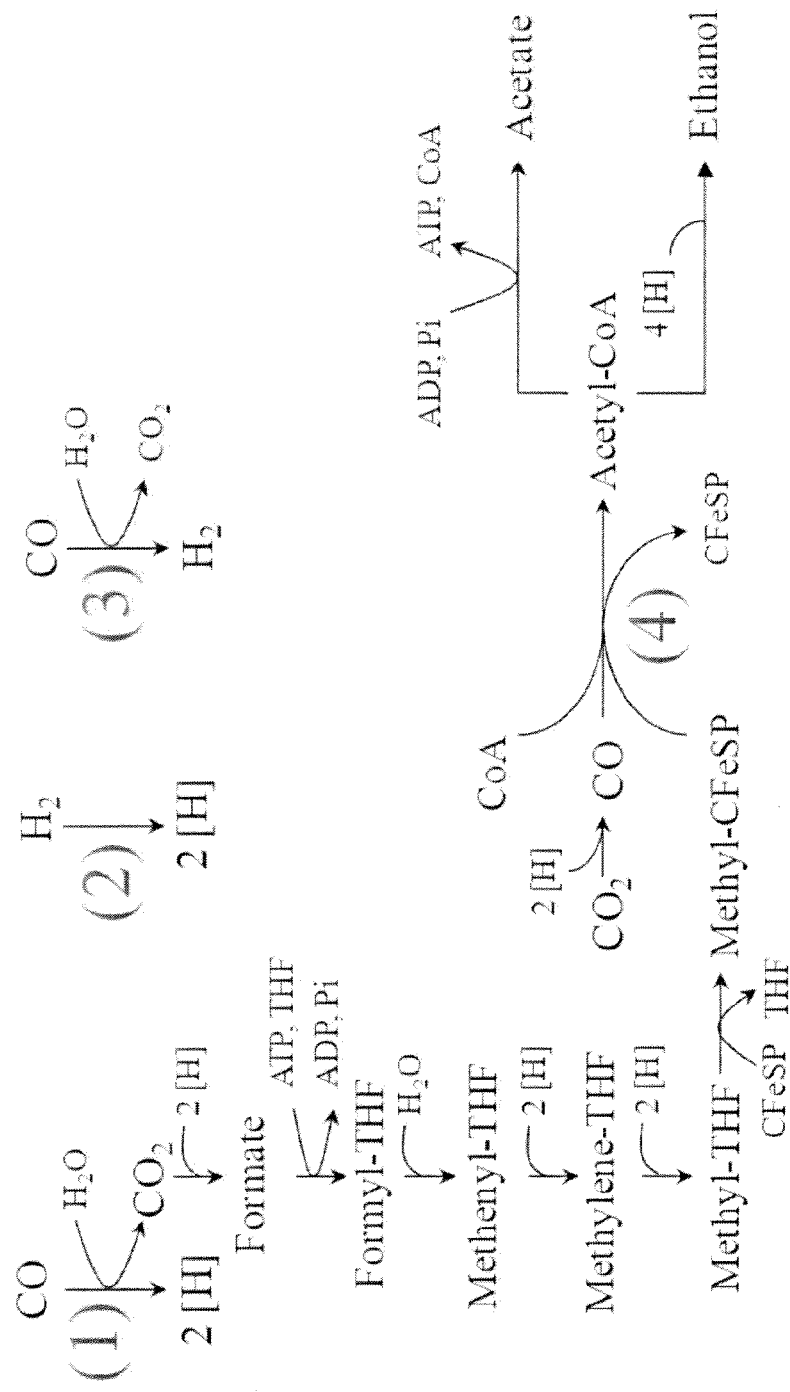
FIG. 1 shows a diagram depicting the Wood-Ljungdahl pathway and formation routes for acetate and ethanol. The transformations that are typically unique to organisms capable of growth on synthesis gas are 1) CO dehydrogenase, 2) hydrogenase, 3) energy-conserving hydrogenase (ECH), and 4) bi-functional CO dehydrogenase/acetyl-CoA synthase. Oxidation of hydrogen to 2 [H] or of CO with $H_2O$ to $CO_2$ and 2 [H] provides reducing equivalents for the reduction of $CO_2$ to formate, of methenyl-tetrahydrofolate (methenyl-THF) to methylene-tetrahydrofolate (methylene-THF), of methylene-THF to methyltetrahydrofolate (methyl-THF), and of $CO_2$ to CO.

This invention is directed, in part, to non-naturally occurring microorganisms that express genes encoding enzymes that catalyze the carbonyl-branch of the Wood-Ljungdahl pathway in conjunction with a MtaABC-type methyltransferase system. Such organisms are capable converting carbohydrates, methanol, a relatively inexpensive organic feedstock that can be derived from synthesis gas, and gasses including CO, $CO_2$, and/or $H_2$ into acetyl-CoA, cell mass, and products such as isopropanol (IPA), 4-hydroxybutyrate (4-HB), and 1,4-butanediol (BDO). Additional product molecules that can be produced by the teachings of this invention include but are not limited to ethanol, butanol, isobutanol, isopropanol, 1,4-butanediol, succinic acid, fumaric acid, malic acid, 4-hydroxybutyric acid, 3-hydroxypropionic acid, lactic acid, adipic acid, 6-aminocaproic acid, hexamethylenediamine, 3-hydroxyisobutyric acid, 2-hydroxyisobutyric acid, methacrylic acid, acrylic acid, and long chain hydrocarbons, alcohols, acids, and esters. The invention is also directed, in part, to non-naturally occurring microorganisms that express genes encoding enzymes that catalyze the carbonyl and methyl-branches of the Wood-Ljungdahl pathway. Such organisms are capable converting gasses including CO, $CO_2$, and/or $H_2$ into acetyl-CoA, cell mass, and products such as IPA, 4-HB, and BDO. Additional product molecules include but are not limited to ethanol, butanol, isobutanol, isopropanol, 1,4-butanediol, succinic acid, fumaric acid, malic acid, 4-hydroxybutyric acid, 3-hydroxypropionic acid, lactic acid, adipic acid, 6-aminocaproic acid, hexamethylenediamine, 3-hydroxyisobutyric acid, 2-hydroxyisobutyric acid, methacrylic acid, acrylic acid, and long chain hydrocarbons, alcohols, acids, and esters.

In one embodiment, the invention provides non-naturally occurring microbial organisms capable of producing isopropanol, 4-hydroxybutyrate, or 1,4-butanediol from methanol and gaseous feedstocks such as mixtures of syngas. In other embodiments, the invention provides non-naturally occurring microbial organisms capable of producing isopropanol, 4-hydroxybutyrate, or 1,4-butanediol from mixtures of syngas, without the need for methanol. In further embodiments, the invention provides pathways for increased yield of isopropanol, 4-hydroxybutyrate or 1,4-butanediol on carbohydrate feedstocks over what would be naturally expected (e.g., one mol isopropanol, 4-hydroxybutyrate or 1,4-butanediol per one mole glucose consumed) by providing an efficient mechanism for fixing the carbon present in methanol or carbon dioxide, fed exogeneously or produced endogenously, into acetyl-CoA.

In another embodiment, the invention provides methods for producing isopropanol, 4-hydroxybutyrate, or 1,4-butanediol through culturing of these non-naturally occurring microbial organisms. Biotechnological processes utilizing these organisms will provide operational flexibility for isopropanol, 4-hydroxybutyrate, and 1,4-butanediol manufacturers to assure the lowest operating costs based on diversified feedstocks and optionally to offset volatility in market-driven commodity pricing of current feedstocks such as oil and natural gas. Furthermore, these processes will deliver sustainable manufacturing practices that utilize renewable feedstocks, reduce energy intensity and lower greenhouse gas emissions.

Acetogens, such as *Moorella thermoacetica, C. ljungdahlii* and *C. carboxidivorans*, can grow on a number of carbon sources ranging from hexose sugars to carbon monoxide. Hexoses, such as glucose, are metabolized first via Embden-Meyerhof-Parnas (EMP) glycolysis to pyruvate, which is then converted to acetyl-CoA via pyruvate:ferredoxin oxidoreductase (PFOR). Acetyl-CoA can be used to build biomass precursors or can be converted to acetate which produces energy via acetate kinase and phosphotransacetylase. The overall conversion of glucose to acetate, energy, and reducing equivalents is given by equation 1:

$$C_6H_{12}O_6 + 4ADP + 4Pi \rightarrow 2CH_3COOH + 2CO_2 + 4ATP + 8[H] \quad \text{equation 1}$$

Acetogens extract even more energy out of the glucose to acetate conversion while also maintaining redox balance by further converting the released $CO_2$ to acetate via the Wood-Ljungdahl pathway.

$$2CO_2 + 8[H] + n\ ADP + n\ Pi \rightarrow CH_3COOH + n\ ATP \quad \text{equation 2}$$

The coefficient n in the above equation signify that this conversion is an energy generating endeavor, as many acetogens can grow in the presence of $CO_2$ via the Wood-Ljungdahl pathway even in the absence of glucose as long as hydrogen is present to supply the necessary reducing equivalents.

$$2CO_2 + 4H_2 + n\ ADP + n\ Pi \rightarrow CH_3COOH + 2H_2O + n\ ATP \quad \text{equation 3}$$

The Wood-Ljungdahl pathway, illustrated in FIG. 1, is coupled to the creation of $Na^+$ or $H^+$ ion gradients that can generate ATP via an $Na^+$- or $H^+$-dependant ATP synthase, respectively (Muller, V. *Appl Environ Microbiol* 69:6345-6353 (2003)). Based on these known transformations, acetogens also have the capacity to utilize CO as the sole carbon and energy source. Specifically, CO can be oxidized to produce reducing equivalents and $CO_2$, or directly assimilated into acetyl-CoA which is subsequently converted to either biomass or acetate.

$$4\ CO + 2H_2O \rightarrow CH_3COOH + 2\ CO_2 \quad \text{equation 4}$$

Even higher acetate yields, however, can be attained when enough hydrogen is present to satisfy the requirement for reducing equivalents.

$$2\ CO + 2H_2 \rightarrow CH_3COOH \quad \text{equation 5}$$

Following from FIG. 1, the production of acetate via acetyl-CoA generates one ATP molecule, whereas the production of ethanol from acetyl-CoA does not and requires two reducing equivalents. Thus one might speculate that ethanol production from syngas will not generate sufficient energy for cell growth in the absence of acetate production. However, under certain conditions, *Clostridium ljungdahlii* produces mostly ethanol from synthesis gas (Klasson et al., *Fuel* 72:1673-1678 (1993)). indicating that some combination of the pathways $$2CO_2 + 6H_2 \rightarrow CH_3CH_2OH + 3H_2O \quad \text{equation 6}$$

$$6CO + 3H_2O \rightarrow CH_3CH_2OH + 4CO_2 \quad \text{equation 7}$$

$$2CO + 4H_2 \rightarrow CH_3CH_2OH + H_2O \quad \text{equation 8}$$

does indeed generate enough energy to support cell growth. Hydrogenic bacteria such as *R. rubrum* can also generate energy from the conversion of CO and water to hydrogen (see FIG. 1) (Simpma et al., *Critical Reviews in Biotechnology* 26:41-65 (2006)). One important mechanism is the coordinated action of an energy converting hydrogenase (ECH) and CO dehydrogenase. The CO dehydrogenase supplies electrons from CO which are then used to reduce protons to $H_2$ by ECH, whose activity is coupled to energy-generating proton translocation. The net result is the generation of energy via the water-gas shift reaction.

Embodiments of the present invention describe the combination of (1) pathways for the conversion of synthesis gases including $CO_2$, CO, and $H_2$ with and without methanol to acetyl-CoA and (2) pathways for the conversion of acetyl-CoA to isopropanol, 4-hydroxybutyrate, or 1,4-butanediol. As such, this invention provides production organisms and conversion routes with inherent yield advantages over organisms engineered to produce isopropanol, 4-hydroxybutyrate, or 1,4-butanediol from carbohydrate feedstocks using only the product pathways proceeding from acetyl-CoA (i.e., (2) of the combination described above). For example, the maximum theoretical yields of isopropanol, 4-hydroxybutyrate, and 1,4-butanediol from glucose are 1 mole per mole using only the metabolic pathways proceeding from acetyl-CoA as described herein. Specifically, 2 moles of acetyl-CoA are derived per mole of glucose via glycolysis and 2 moles of acetyl-CoA are required per mole of isopropanol, 4-hydroxybutyrate, or 1,4-butanediol. The net conversions are described by the following stoichiometric equations:

Isopropanol: $C_6H_{12}O_6 + 1.5O_2 \rightarrow C_3H_8O + 3CO_2 + 2H_2O$

4-Hydroxybutyate: $C_6H_{12}O_6 + 1.5O_2 \rightarrow C_4H_8O_3 + 2CO_2 + 2H_2O$ 1,4-Butanediol: $C_6H_{12}O_6 \rightarrow C_4H_{10}O_2 + CH_2O_2 + CO_2$ On the other hand, gasification of glucose to its simpler components, CO and $H_2$, followed by their conversion to isopropanol, 4-hydroxybutyrate, and 1,4-butanediol using the pathways described herein results in the following maximum theoretical yields:

Isopropanol: $6CO+6H_2 \rightarrow 1.333C_3H_8O+2CO_2+0.667H_2O$

4-Hydroxybutyate: $6CO+6H_2 \rightarrow 1.333C_4H_8O_3+0.667CO_2+0.667H_2O$ 1,4-Butanediol: $6CO+6H_2 \rightarrow 1.091C_4H_{10}O_2+1.636CO_2+0.545H_2O$ Note that the gasification of glucose can at best provide 6 moles of CO and 6 moles of $H_2$. Similarly, the combination of certain syngas-utilization pathway components with the acetyl-CoA to isopropanol, 4-hydroxybutyrate, or 1,4-butanediol pathways results in high yields of these products from carbohydrates by providing an efficient mechanism for fixing the carbon present in carbon dioxide, fed exogeneously or produced endogenously, into acetyl-CoA (see below and also Example II).

Isopropanol: $C_6H_{12}O_6 \rightarrow 1.333C_3H_8O+2CO_2+0.667H_2O$

4-Hydroxybutyate: $C_6H_{12}O_6 \rightarrow 1.333C_4H_8O_3+0.667CO_2+0.667H_2O$ 1,4-Butanediol: $C_6H_{12}O_6 \rightarrow 1.091C_4H_{10}O_2+1.636CO_2+0.545H_2O$ The maximum theoretical yields of isopropanol, 4-hydroxybutyrate, and 1,4-butanediol from synthesis gases or carbohydrates can be further enhanced by the addition of methanol as described below:

Isopropanol: $CH_4O+6CO+6H_2 \rightarrow 1.667C_3H_8O+2CO_2+1.333H_2O$

4-Hydroxybutyate: $CH_4O+6CO+6H_2 \rightarrow 1.667C_4H_8O_3+0.333CO_2+1.333H_2O$ 1,4-Butanediol: $CH_4O+6CO+6H_2 \rightarrow 1.364C_4H_{10}O_2+1.545CO_2+1.182H_2O$ Isopropanol: $2CH_4O+6CO+6H_2 \rightarrow 2C_3H_8O+2CO_2+2H_2O$ 4-Hydroxybutyate: $2CH_4O+6CO+6H_2 \rightarrow 2C_4H_8O_3+2H_2O$ 1,4-Butanediol: $2CH_4O+6CO+6H_2 \rightarrow 1.636C_4H_{10}O_2+1.455CO_2+1.818H_2O$ Isopropanol: $CH_4O+C_6H_{12}O_6 \rightarrow 1.667C_3H_8O+2CO_2+1.333H_2O$ 4-Hydroxybutyate: $CH_4O+C_6H_{12}O_6 \rightarrow 1.667C_4H_8O_3+0.333CO_2+1.333H_2O$ 1,4-Butanediol: $CH_4O+C_6H_{12}O_6 \rightarrow 1.364C_4H_{10}O_2+1.545CO_2+1.182H_2O$ Isopropanol: $2CH_4O+C_6H_{12}O_6 \rightarrow 2C_3H_8O+2CO_2+2H_2O$ 4-Hydroxybutyate: $2CH_4O+C_6H_{12}O_6 \rightarrow 2C_4H_8O_3+2H_2O$ 1,4-Butanediol: $2CH_4O+C_6H_{12}O_6 \rightarrow 1.636C_4H_{10}O_2+1.455CO_2+1.818H_2O$ Thus, the organisms and conversion routes described herein provide an efficient means of converting carbohydrates to products such as isopropanol, 4-hydroxybutyrate, or 1,4-butanediol. Additional product molecules that can be produced by the teachings of this invention include but are not limited to ethanol, butanol, isobutanol, isopropanol, 1,4-butanediol, succinic acid, fumaric acid, malic acid, 4-hydroxybutyric acid, 3-hydroxypropionic acid, lactic acid, adipic acid, 6-aminocaproic acid, hexamethylenediamine, 3-hydroxyisobutyric acid, 2-hydroxyisobutyric acid, methacrylic acid, acrylic acid, and long chain hydrocarbons, alcohols, acids, and esters.

In some embodiments, the non-naturally occurring organisms of the present invention incorporating the Wood-Ljungdahl pathway can function in the presence of an electron acceptor other than $CO_2$. Wood-Ljungdahl pathway enzymes are oxygen sensitive which can preclude the use of oxygen to improve the energetics of the organism. Under certain conditions, electron acceptor nitrate can block carbon assimilation by the Wood-Ljungdahl pathway, by transcriptional regulation of genes encoding Wood-Ljungdahl. Nonetheless, in some embodiments, a non-naturally occurring organism of the invention utilizing the Wood-Ljungdahl pathway can use nitrate as an electron acceptor to improve overall energetics, as described further below.

In addition to challenges in energy balance, a further challenge of incorporating the Wood-Ljungdahl pathway involves redox balance. Acetogens naturally make acetate as the sole product, not isopropanol. Some syngas utilizers such as *Clostridium carboxydivorans* have been shown to make multiple products (i.e., ethanol, butanol, acetate, and butyrate). Converting 2 acetyl-CoA molecules to one isopropanol provides 1 reducing equivalent. By contrast, the aforementioned products can produce 2 or more reducing equivalents.

Non-naturally occurring organisms of the present invention employing the combination of pathways disclosed herein can provide a yield of isopropanol, for example, on glucose up to 0.44 g/g glucose. This yield is improved over organism that do not incorporate the Wood-Ljungdahl pathway.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within an isopropanol, 4-hydroxybutyrate, or 1,4-butanediol biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having isopropanol, 4-hydroxybutyrate, or 1,4-butanediol biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw Sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan.-5-1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep.-16-1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Figure 2A:
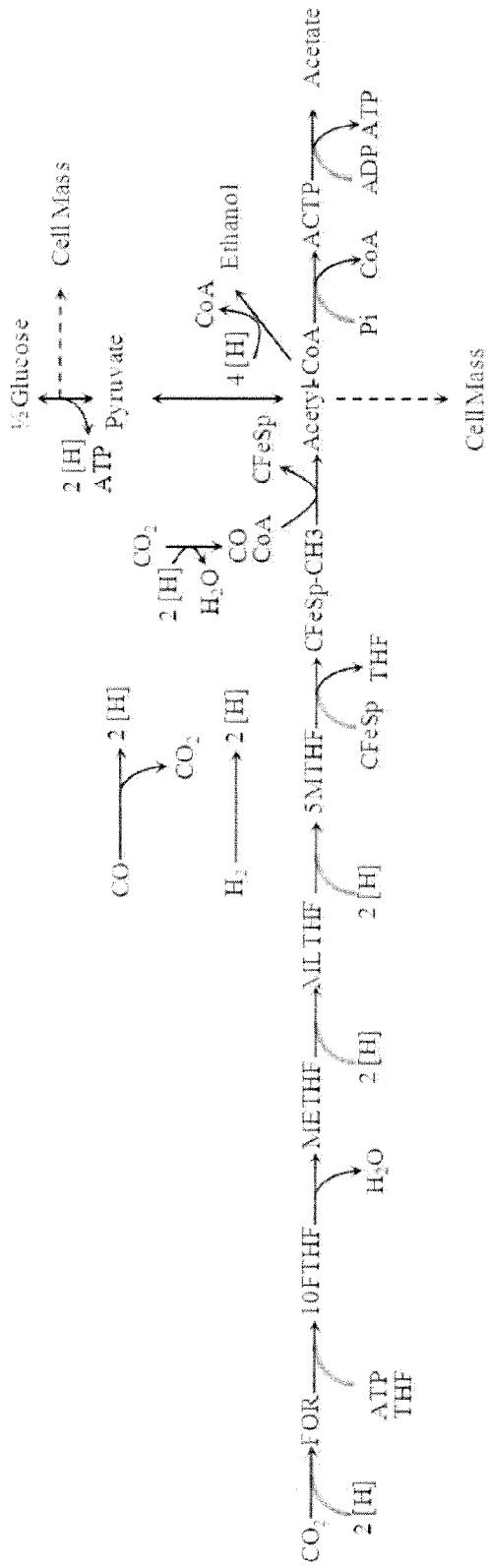
FIG. 2A shows the complete Wood-Ljungdahl pathway for the conversion of carbohydrates and/or gases including CO, $CO_2$, and/or $H_2$ to acetyl-CoA which is subsequently converted to cell mass and products such as ethanol or acetate.

*Escherichia coli* is a common organism with a well-studied set of available genetic tools. Engineering the capability to convert $CO_2$, CO and/or $H_2$ into acetyl-CoA, the central metabolite from which cell mass components and many valuable products can be derived, into a foreign host such as *E. coli* can be accomplished following the expression of exogenous genes that encode various proteins of the Wood-Ljungdahl pathway. This pathway is active in acetogenic organisms such as *Morella thermoacetica* (formerly, *Clostridium thermoaceticum*), which has been the model organism for elucidating the Wood-Ljungdahl pathway since its isolation in 1942 (Fontaine et al., *J. Bacteriol.* 43:701-715 (1942)). The Wood-Ljungdahl pathway includes two branches: the Eastern (or methyl) branch that enables the conversion of $CO_2$ to methyltetrahydrofolate (Me-THF) and the Western (or carbonyl) branch that enables the conversion of methyl-THF, CO, and Coenzyme-A into acetyl-CoA as shown in FIG. 2A. Such an organism is capable of converting gases comprising CO, $CO_2$, and/or $H_2$ into acetyl-CoA, cell mass, and products such as isopropanol, 4-hydroxybutyrate and 1,4-butanediol. Such an organism is also capable of producing isopropanol, 4-hydroxybutyrate or 1,4-butanediol from carbohydrates at the stoichiometric optimum yield. For example, in combination with the acetyl-CoA to isopropanol pathway, the Wood-Ljungdahl enzymes provide the means to produce 4 moles of isopropanol for every 3 moles of glucose as opposed to 1 mol isopropanol/1 mol glucose which would be attainable in the absence of the Wood-Ljungdahl pathway enzymes. In some embodiments, the present invention provides a non-naturally occurring microorganism expressing genes encoding enzymes that catalyze the carbonyl-branch of the Wood-Ljungdahl pathway in conjunction with a MtaABC-type methyltransferase system. Such an organism is capable converting methanol, a relatively inexpensive organic feedstock that can be derived from synthesis gas, and gases including CO, $CO_2$, and/or $H_2$ into acetyl-CoA, cell mass, and products. In addition to gaseous substrates, the organism can utilize methanol exclusively or in combination with carbohydrate feedstocks such as glucose to produce products such as isopropanol, 4-hydroxybutyrate or 1,4-butanediol in a high yield. Additional product molecules that can be produced by the teachings of this invention include but are not limited to ethanol, butanol, isobutanol, isopropanol, 1,4-butanediol, succinic acid, fumaric acid, malic acid, 4-hydroxybutyric acid, 3-hydroxypropionic acid, lactic acid, adipic acid, 6-aminocaproic acid, hexamethylenediamine, 3-hydroxyisobutyric acid, 2-hydroxyisobutyric acid, methacrylic acid, acrylic acid, and long chain hydrocarbons, alcohols, acids, and esters.

Figure 2B:
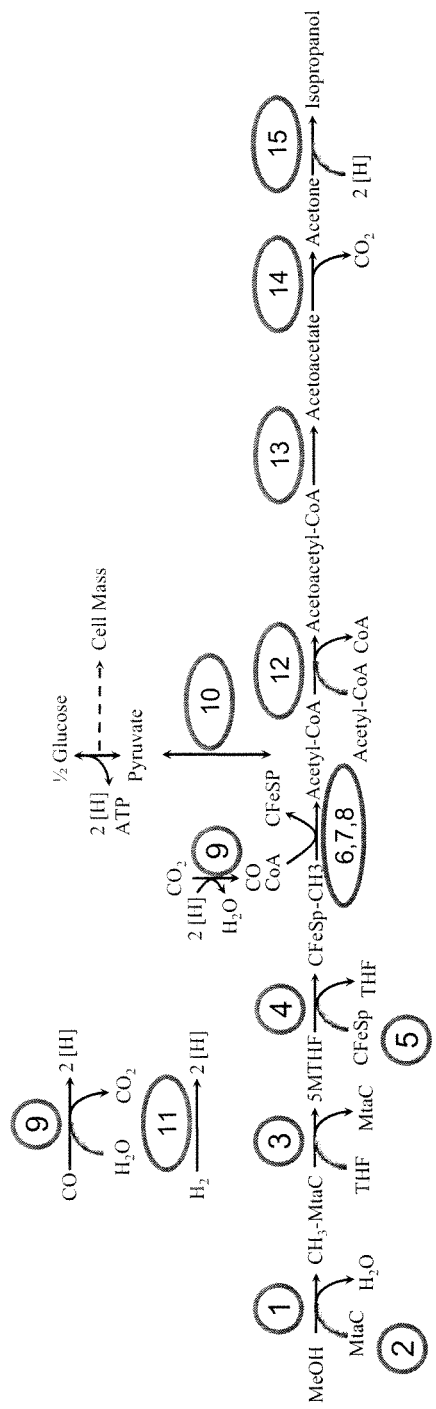
FIG. 2B shows a synthetic metabolic pathway for the conversion of carbohydrates and/or gases including CO, $CO_2$, and/or $H_2$, and methanol to acetyl-CoA and further to isopropanol.
Figure 2C:
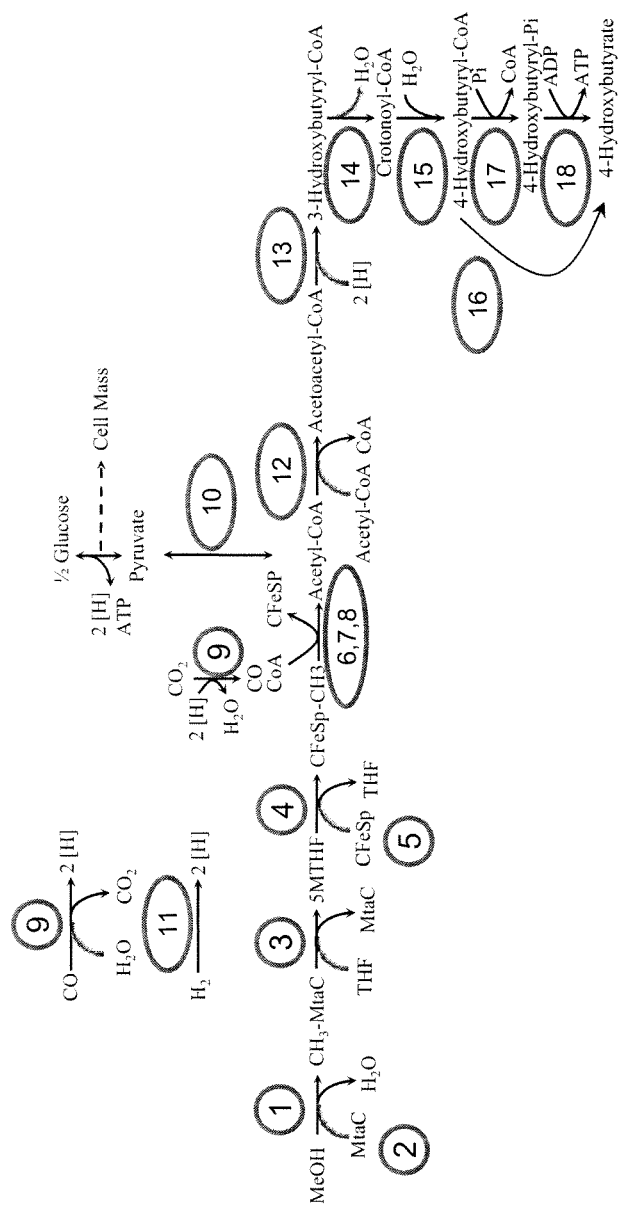
FIG. 2C shows a synthetic metabolic pathway for the conversion of carbohydrates and/or gases including CO, $CO_2$, and/or $H_2$, and methanol to acetyl-CoA and further to 4-hydroxybutyrate.
Figure 2D:
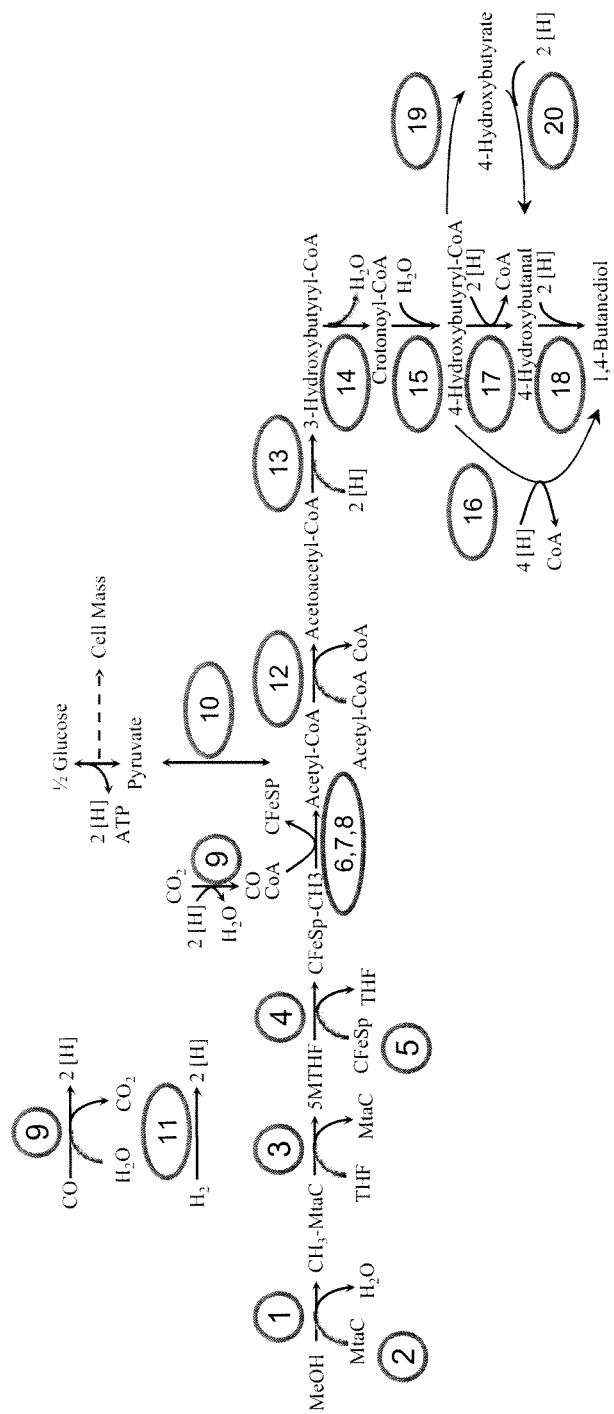
FIG. 2D shows a synthetic metabolic pathway for the conversion of carbohydrates and/or gases including CO, $CO_2$, and/or $H_2$, and methanol to acetyl-CoA and further to 1,4-butanediol.

In some embodiments organisms of the present invention have the following capabilities as depicted in FIG. 2B: 1) a functional methyltransferase system enabling the production of 5-methyl-tetrahydrofolate (Me-THF) from methanol and THF, 2) the ability to combine CO, Coenzyme A, and the methyl group of Me-THF to form acetyl-CoA, and 3) the ability to synthesize IPA from acetyl-CoA. In other embodiments, organisms of the present invention have a functional methyltransferase system, the ability to synthesize acetyl-CoA, and the ability to synthesize 4-HB from acetyl-CoA as depicted in FIG. 2C. Still other organisms described herein have a functional methyltransferase system, the ability to synthesize acetyl-CoA, and the ability to synthesize BDO from acetyl-CoA depicted in FIG. 2D.

In some embodiments, organisms of the present invention are able to 'fix' carbon from exogenous CO and/or $CO_2$ and methanol to synthesize acetyl-CoA, cell mass, and products. The direct conversion of synthesis gas to acetate is an energetically neutral process (see FIGS. 1 and 2A). Specifically, one ATP molecule is consumed during the formation of formyl-THF by formyl-THF synthase and one ATP molecule is produced during the production of acetate via acetate kinase. ATP consumption is circumvented by ensuring that the methyl group on the methyl branch product, methyl-THF, is obtained from methanol rather than $CO_2$. This thereby ensures that acetate formation has a positive ATP yield that can help support cell growth and maintenance. A host organism engineered with these capabilities that also naturally possesses the capability for anapleurosis, such as *E. coli*, can grow on the methanol and syngas-generated acetyl-CoA in the presence of a suitable external electron acceptor such as nitrate. This electron acceptor is used to accept electrons from the reduced quinone formed via succinate dehydrogenase. One advantage of adding an external electron acceptor is that additional energy for cell growth, maintenance, and product formation can be generated from respiration of acetyl-CoA. In other embodiments, a pyruvate ferredoxin oxidoreductase (PFOR) enzyme can be inserted into the strain to provide the synthesis of biomass precursors in the absence of an external electron acceptor. A further characteristic of organisms of the present invention is the capability of extracting reducing equivalents from molecular hydrogen. This enables a high yield of reduced products such as ethanol, butanol, isobutanol, isopropanol, 1,4-butanediol, succinic acid, fumaric acid, malic acid, 4-hydroxybutyric acid, 3-hydroxypropionic acid, lactic acid, adipic acid, 6-aminocaproic acid, hexamethylenediamine, 3-hydroxyisobutyric acid, 2-hydroxyisobutyric acid, methacrylic acid, and acrylic acid.

Organisms of the present invention can produce acetyl-CoA, cell mass, and targeted chemicals, more specifically IPA, 4-HB, or BDO, from: 1) methanol and CO, 2) methanol, $CO_2$, and $H_2$, 3) methanol, CO, $CO_2$, and $H_2$, 4) methanol and synthesis gas comprising CO and $H_2$, 5) methanol and synthesis gas comprising CO, $CO_2$, and $H_2$, 6) one or more carbohydrates, 7) methanol and one or more carbohydrates, and 8) methanol. Exemplary carbohydrates include but are not limited to glucose, sucrose, xylose, arabinose and glycerol.

Successfully engineering pathways into an organism involves identifying an appropriate set of enzymes, cloning their corresponding genes into a production host, optimizing the stability and expression of these genes, optimizing fermentation conditions, and assaying for product formation following fermentation. A number of enzymes catalyze each step of the pathways for the conversion of synthesis gas and methanol to acetyl-CoA, and further to isopropanol, 4-hydroxybutyrate, or 1,4-butanediol. To engineer a production host for the utilization of syngas and methanol, one or more exogenous DNA sequence(s) encoding the enzymes can be expressed in the microorganism.

In some embodiments, the present invention provides a non-naturally occurring microbial organism having an isopropanol pathway that includes at least one exogenous nucleic acid encoding an isopropanol pathway enzyme expressed in a sufficient amount to produce isopropanol. The isopropanol pathway enzyme includes an acetoacetyl-CoA thiolase, an acetoacetyl-CoA transferase, an acetoacetate decarboxylase, and an isopropanol dehydrogenase. In some embodiments, an isopropanol pathway of the present invention includes a succinyl-CoA:3-ketoacid-CoA transferase (SCOT), an acetoacetate decarboxylase, and an isopropanol dehydrogenase. SCOT is a type of acetoacetyl-CoA transferase.

The use of a succinyl-CoA:3-ketoacid-CoA transferase confers a multitude of benefits when converting acetoacetyl-CoA to acetoacetate as part of an isopropanol synthesis pathway: 1) Succinyl-CoA:3-ketoacid-CoA transferase can function as part of a pathway from acetyl-CoA to isopropanol that also generates an energetic equivalent (e.g., ATP, GTP); 2) Succinyl-CoA:3-ketoacid-CoA will not compete with the product pathway for acetyl-CoA substrate; 3) Succinyl-CoA:3-ketoacid-CoA relies on a CoA donor/acceptor molecule, succinate, that is naturally synthesized in most organisms for industrial production.

The non-naturally occurring organisms of the invention are more efficient from an energetic standpoint compared to organisms that utilize acetoacetyl-CoA hydrolase for isopropanol production. Acetoacetyl-CoA hydrolase removes the CoA group from acetoacetyl-CoA without the generation of any energetic equivalents. Succinyl-CoA:3-ketoacid-CoA transferase in combination with, for example, succinyl-CoA synthetase enables the net generation of one energetic equivalent (e.g., GTP, ATP). Succinyl-CoA synthetase is a nearly ubiquitously present enzyme and is an integral component of the well-known tricarboxylic acid cycle.

Acetyl-CoA:acetoacetyl-CoA transferase can be used in combination with acetate kinase and phosphotransacetylase or an ADP-forming acetyl-CoA synthetase to generate an energetic equivalent. Such combinations are more advantageous from an energetic standpoint than using acetoacetyl-CoA hydrolase. However, acetate kinase, phosphotransacetylase, and ADP-forming acetyl-CoA synthetase are reversible which can lead to the formation of substantial amounts of acetate byproduct. Succinyl-CoA synthetase has a lower activity or no activity at all on acetyl-CoA compared to phosphotransacetylase or an ADP-forming acetyl-CoA synthetase.

It is thus desirable in the case of isopropanol to use a CoA donor/acceptor molecule that is completely disconnected from the product pathway. Butyryl-CoA:acetoacetyl-CoA transferase is one such enzyme and is taught by Subbian et al., US 2008/0293125. However, butyrate is not naturally present at substantial levels in most organisms including the industrial workhouse organisms *Escherichia coli* and *Saccharomyces cerevisiae*. Thus the capability of synthesizing a catalytic amount of butyrate would have to engineered into such organisms to enable butyryl-CoA:acetoacetyl-CoA transferase to function as part of an isopropanol synthesis pathway. Butyrate is also a foul smelling compound and substantial leakage of butyrate out of the organism could require special process engineering steps to ensure that it is not released into the air. On the other hand, succinate is non-odorous and is synthesized in a plethora of organisms including *E. coli* and *S. cerevisiae*. Typical succinate forming enzymes include succinyl-CoA synthetase and alpha-ketoglutarate dehydrogenase, both components of the well-known tricarboxylic acid cycle.

Such organisms may also include at least one enzyme or polypeptide such as a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In some embodiments, organisms having an isopropanol pathway have a methanol methyltransferase. In such embodiments, the organisms utilize a feedstock such as 1) methanol and CO, 2) methanol, $CO_2$, and $H_2$, 3) methanol, CO, $CO_2$, and $H_2$, 4) methanol and synthesis gas comprising CO and $H_2$, 5) methanol and synthesis gas comprising CO, $CO_2$, and $H_2$, 6) one or more carbohydrates, 7) methanol and one or more carbohydrates, and 8) methanol. Exemplary carbohydrates include but are not limited to glucose, sucrose, xylose, arabinose and glycerol.

In other embodiments, organisms of the present invention have a formate dehydrogenase, a formyltetrahydrofolate synthetase, a methenyltetrahydrofolate cyclohydrolase, a methylenetetrahydrofolate dehydrogenase, and a methylenetetrahydrofolate reductase. Such organisms utilize a feedstock selected from the group consisting of 1) CO, 2) $CO_2$ and $H_2$, 3) CO and $CO_2$, 4) synthesis gas comprising CO and $H_2$, 5) synthesis gas comprising CO, $CO_2$, and $H_2$, and 6) one or more carbohydrates. Exemplary carbohydrates include but are not limited to glucose, sucrose, xylose, arabinose, and glycerol.

The invention also provides a non-naturally occurring microbial organism having a 4-hydroxybutryate pathway that includes at least one exogenous nucleic acid encoding an 4-hydroxybutyrate pathway enzyme expressed in a sufficient amount to produce 4-hydroxybutryate. The 4-hydroxybutryate pathway enzyme includes an acetoacetyl-CoA thiolase, a 3-hydroxybutyryl-CoA dehydrogenase, a crotonase, a crotonyl-CoA hydratase, a 4-hydroxybutyryl-CoA transferase, a 4-hydroxybutyryl-CoA hydrolase, a 4-hydroxybutyryl-CoA synthetase, a phosphotrans-4-hydroxybutyrylase, and a 4-hydroxybutyrate kinase.

Such organisms can also include at least one enzyme or polypeptide such as a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In some embodiments, organisms that have a 4-hydroxybutyrate pathway can include a methanol methyltransferase. Such organisms utilize a feedstock such as 1) methanol and CO, 2) methanol, $CO_2$, and $H_2$, 3) methanol, CO, $CO_2$, and $H_2$, 4) methanol and synthesis gas comprising CO and $H_2$, 5) methanol and synthesis gas comprising CO, $CO_2$, and $H_2$, 6) one or more carbohydrates, 7) methanol and one or more carbohydrates, and 8) methanol. Exemplary carbohydrates include but are not limited to glucose, sucrose, xylose, arabinose and glycerol.

Other organisms that have a 4-hydroxybutyrate pathway can have a formate dehydrogenase, a formyltetrahydrofolate synthetase, a methenyltetrahydrofolate cyclohydrolase, a methylenetetrahydrofolate dehydrogenase, and a methylenetetrahydrofolate reductase. Such organisms utilize a feedstock such as 1) CO, 2) $CO_2$ and $H_2$, 3) CO and $CO_2$, 4) synthesis gas comprising CO and $H_2$, 5) synthesis gas comprising CO, $CO_2$, and $H_2$, and 6) one or more carbohydrates. Exemplary carbohydrates include but are not limited to glucose, sucrose, xylose, arabinose, and glycerol.

The present invention also provides a non-naturally occurring microbial organism having a 1,4-butanediol pathway that includes at least one exogenous nucleic acid encoding a 1,4-butanediol pathway enzyme expressed in a sufficient amount to produce 1,4-butanediol. The 1,4-butanediol pathway enzyme include, for example, an acetoacetyl-CoA thiolase, a 3-Hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), a 4-hydroxybutyryl-CoA transferase, a 4-hydroxybutyryl-CoA hydrolase, a 4-hydroxybutyryl-CoA synthetase, a 4-hydroxybutyrate reductase, a phosphotrans-4-hydroxybutyrylase, a 4-hydroxybutyrate kinase, and a 1,4-butanediol dehydrogenase.

Such organisms can also include at least one enzyme or polypeptide such as a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In some embodiments, an organism having a 1,4-butanediol pathway can include a methanol methyltransferase. Such organisms utilize a feedstock such as 1) methanol and CO, 2) methanol, $CO_2$, and $H_2$, 3) methanol, CO, $CO_2$, and $H_2$, 4) methanol and synthesis gas comprising CO and $H_2$, 5) methanol and synthesis gas comprising CO, $CO_2$, and $H_2$, 6) one or more carbohydrates, 7) methanol and one or more carbohydrates, and 8) methanol. Exemplary carbohydrates include but are not limited to glucose, sucrose, xylose, arabinose and glycerol.

In other embodiments, an organism having a 1,4-butanediol pathway can include a formate dehydrogenase, a formyltetrahydrofolate synthetase, a methenyltetrahydrofolate cyclohydrolase, a methylenetetrahydrofolate dehydrogenase, and a methylenetetrahydrofolate reductase. Such organisms utilize a feedstock selected from the group consisting of: 1) CO, 2) CO, and $H_2$, 3) CO and $CO_2$, 4) synthesis gas comprising CO and $H_2$, 5) synthesis gas comprising CO, $CO_2$, and $H_2$, and 6) one or more carbohydrates. Exemplary carbohydrates include but are not limited to glucose, sucrose, xylose, arabinose, and glycerol.

Also disclosed herein is a non-naturally occurring microbial organism having an acetyl-CoA pathway that includes at least one exogenous nucleic acid encoding an acetyl-CoA pathway enzyme expressed in a sufficient amount to produce acetyl-CoA. The acetyl-CoA pathway enzyme includes a methanol methyltransferase and an acetyl-CoA synthase.

In still further embodiments, the present invention provides a non-naturally occurring microbial organism having an isopropanol pathway comprising at least one exogenous nucleic acid encoding an isopropanol pathway enzyme expressed in a sufficient amount to produce isopropanol, said isopropanol pathway enzyme comprising a methanol methyltransferase, a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In some embodiments, such an organism can include an exogenous polypeptide or enzyme such as an acetoacetyl-CoA thiolase, an acetoacetyl-CoA transferase, an acetoacetyl-CoA hydrolase, an acetoacetyl-CoA synthetase, a phosphotransacetoacetylase, an acetoacetate kinase, an acetoacetate decarboxylase, and an isopropanol dehydrogenase. In additional embodiments, such an organism can include an exogenous polypeptide or enzyme such as a succinyl-CoA:3-ketoacid-CoA transferase (SCOT), an acetoacetate decarboxylase, and an isopropanol dehydrogenase.

Expression of the modified Wood-Ljungdahl pathway in a foreign host (see FIG. 2B) requires a set of methyltransferases to utilize the carbon and hydrogen provided by methanol and the carbon provided by CO and/or $CO_2$. A complex of 3 methyltransferase proteins, denoted MtaA, MtaB, and MtaC, perform the desired methanol methyltransferase activity (Naidu and Ragsdale, *J. Bacteriol.* 183:3276-3281 (2001); Ragsdale, S. W., *Crit. Rev. Biochem. Mol. Biol.* 39:165-195 (2004); Sauer et al., *Eur. J. Biochem.* 243:670-677 (1997); Tallant and Krzycki, *J. Bacteriol.* 178:1295-1301 (1996); Tallant and Krzycki, *J. Bacteriol.* 179:6902-6911 (1997); Tallant et al., *J Biol. Chem.* 276:4485-4493 (2001)).

MtaB is a zinc protein that catalyzes the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006)) and *Methanosarcina acetivorans* (Galagan et al., *Genome Res* 12:532-542 (2002)), as well as the acetogen, *Moorella thermoacetica* (Das et al., *Proteins* 67:167-176 (2007)). In general, the MtaB and MtaC genes are adjacent to one another on the chromosome as their activities are tightly interdependent. The protein sequences of various MtaB and MtaC encoding genes in *M. barkeri*, *M. acetivorans*, and *M. thermoaceticum* can be identified by their following GenBank accession numbers.

| Protein | GenBank ID | GI Number | Organism |
| --- | --- | --- | --- |
| MtaB1 | YP_304299 | 73668284 | *Methanosarcina barkeri* |
| MtaC1 | YP_304298 | 73668283 | *Methanosarcina barkeri* |
| MtaB2 | YP_307082 | 73671067 | *Methanosarcina barkeri* |
| MtaC2 | YP_307081 | 73671066 | *Methanosarcina barkeri* |
| MtaB3 | YP_304612 | 73668597 | *Methanosarcina barkeri* |
| MtaC3 | YP_304611 | 73668596 | *Methanosarcina barkeri* |
| MtaB1 | NP_615421 | 20089346 | *Methanosarcina acetivorans* |
| MtaB1 | NP_615422 | 20089347 | *Methanosarcina acetivorans* |
| MtaB2 | NP_619254 | 20093179 | *Methanosarcina acetivorans* |
| MtaC2 | NP_619253 | 20093178 | *Methanosarcina acetivorans* |
| MtaB3 | NP_616549 | 20090474 | *Methanosarcina acetivorans* |
| MtaC3 | NP_616550 | 20090475 | *Methanosarcina acetivorans* |
| MtaB | YP_430066 | 83590057 | *Moorella thermoacetica* |
| MtaC | YP_430065 | 83590056 | *Moorella thermoacetica* |

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc Natl Acad Sci USA* 103:18917-18922 (2006)). The MtaB genes, YP_307082 and YP_304612, in *M. barkeri* were identified by sequence homology to YP_304299. In general, homology searches are an effective means of identifying methanol methyltransferases because MtaB encoding genes show little or no similarity to methyltransferases that act on alternative substrates such as trimethylamine, dimethylamine, monomethylamine, or dimethylsulfide. The MtaC genes, YP_307081 and YP_304611, were identified based on their proximity to the MtaB genes and also their homology to YP_304298. The three sets of MtaB and MtaC genes from *M. acetivorans* have been genetically, physiologically, and biochemically characterized (Pritchett and Metcalf, *Mol. Microbiol* 56:1183-1194 (2005)). Mutant strains lacking two of the sets were able to grow on methanol, whereas a strain lacking all three sets of MtaB and MtaC genes sets could not grow on methanol. This indicates that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F Struct. Biol Cryst. Commun.* 61:537-540 (2005)) and further characterized by Northern hybridization and Western Blotting (Das et al., *Proteins* 67:167-176 (2007)).

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006)) and *Methanosarcina acetivorans* (Galagan et al., *Genome Res* 12:532-542 (2002)), as well as the acetogen, *Moorella thermoacetica* (Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

TABLE 2

| Protein | GenBank ID | GI Number | Organism |
| --- | --- | --- | --- |
| MtaA | YP_304602 | 73668587 | *Methanosarcina barkeri* |
| MtaA1 | NP_619241 | 20093166 | *Methanosarcina acetivorans* |
| MtaA2 | NP_616548 | 20090473 | *Methanosarcina acetivorans* |

The MtaA gene, YP_304602, from *M. barkeri* was cloned, sequenced, and functionally overexpressed in *E. coli* (Halms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). There are multiple additional MtaA homologs in *M. barkeri* and *M. acetivorans* that are as yet uncharacterized, but can also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from $CH_3$-MtaC to Coenzyme M, an *M. thermoacetica* MtaA is likely to transfer the methyl group to methyltetrahydrofolate given the similar roles of methyltetrahydrofolate and Coenzyme M in methanogens and acetogens, respectively. The protein sequences of putative MtaA encoding genes from *M. thermoacetica* can be identified by the following GenBank accession numbers.

TABLE 3

| Protein | GenBank ID | GI Number | Organism |
| --- | --- | --- | --- |
| MtaA | YP_430937 | 83590928 | Moorella thermoacetica |
| MtaA | YP_431175 | 83591166 | Moorella thermoacetica |
| MtaA | YP_430935 | 83590926 | Moorella thermoacetica |

ACS/CODH is the central enzyme of the carbonyl branch of the Wood-Ljungdahl pathway. It catalyzes the reversible reduction of carbon dioxide to carbon monoxide and also the synthesis of acetyl-CoA from carbon monoxide, Coenzyme A, and the methyl group from a methylated corrinoid-iron-sulfur protein. The corrinoide-iron-sulfur-protein is methylated by methyltetrahydrofolate via a methyltransferase. Expression of ACS/CODH in a foreign host can be done by introducing one or more of the following proteins and their corresponding activities: Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA) or Nickel-protein assembly protein (CooC).

The genes used for carbon-monoxide dehydrogenase/acetyl-CoA synthase activity typically reside in a limited region of the native genome that may be an extended operon (Morton et al., *J Biol. Chem.* 266:23824-23828 (1991); Ragsdale, S. W., *Crit. Rev. Biochem. Mol. Biol.* 39:165-195 (2004); Roberts et al., *Proc Natl Acad Sci USA* 86:32-36 (1989)). Each of the genes in this operon from the acetogen, *M. thermoacetica*, has already been cloned and expressed actively in *E. coli* (Lu et al., *J Biol. Chem.* 268:5605-5614 (1993); Roberts et al., *Proc Natl Acad Sci USA* 86:32-36 (1989)). The protein sequences of these genes can be identified by the following GenBank accession numbers.

TABLE 4

| Protein | GenBank ID | GI Number | Organism |
| --- | --- | --- | --- |
| AcsE | YP_430054 | 83590045 | Moorella thermoacetica |
| AcsD | YP_430055 | 83590046 | Moorella thermoacetica |
| AcsF | YP_430056 | 83590047 | Moorella thermoacetica |
| Orf7 | YP_430057 | 83590048 | Moorella thermoacetica |
| AcsC | YP_430058 | 83590049 | Moorella thermoacetica |
| AcsB | YP_430059 | 83590050 | Moorella thermoacetica |
| AcsA | YP_430060 | 83590051 | Moorella thermoacetica |
| CooC | YP_430061 | 83590052 | Moorella thermoacetica |

The hydrogenogenic bacterium, *Carboxydothermus hydrogenoformans*, can utilize carbon monoxide as a growth substrate by means of acetyl-CoA synthase (Wu et al., *PLoS Genet.* 1:e65 (1995)). In strain Z-2901, the acetyl-CoA synthase enzyme complex lacks carbon monoxide dehydrogenase due to a frameshift mutation (Wu et al., *PLoS Genet.* 1:e65 (1995)), whereas in strain DSM 6008, a functional unframeshifted full-length version of this protein has been purified (Svetlitchnyi et al., *Proc Natl Acad Sci U.S.A* 101: 446-451 (2004)). The protein sequences of the *C. hydrogenoformans* genes from strain Z-2901 are identified by the following GenBank accession numbers. Sequences for *Carboxydothermus hydrogenoformans* DSM 6008 are not yet accessible in publicly available databases.

TABLE 5

| Protein | GenBank ID | GI Number | Organism |
| --- | --- | --- | --- |
| AcsE | YP_360065 | 78044202 | Carboxydothermus hydrogenoformans |
| AcsD | YP_360064 | 78042962 | Carboxydothermus hydrogenoformans |
| AcsF | YP_360063 | 78044060 | Carboxydothermus hydrogenoformans |
| Orf7 | YP_360062 | 78044449 | Carboxydothermus hydrogenoformans |
| AcsC | YP_360061 | 78043584 | Carboxydothermus hydrogenoformans |
| AcsB | YP_360060 | 78042742 | Carboxydothermus hydrogenoformans |
| CooC | YP_360059 | 78044249 | Carboxydothermus hydrogenoformans |

Homologous ACS/CODH genes can also be found in the draft genome assembly of *Clostridium carboxidivorans* P7.

TABLE 6

| Protein | GenBank ID | GI Number | Organism |
| --- | --- | --- | --- |
| AcsA | ZP_05392944.1 | 255526020 | Clostridium carboxidivorans P7 |
| CooC | ZP_05392945.1 | 255526021 | Clostridium carboxidivorans P7 |
| AcsF | ZP_05392952.1 | 255526028 | Clostridium carboxidivorans P7 |
| AcsD | ZP_05392953.1 | 255526029 | Clostridium carboxidivorans P7 |
| AcsC | ZP_05392954.1 | 255526030 | Clostridium carboxidivorans P7 |
| AcsE | ZP_05392955.1 | 255526031 | Clostridium carboxidivorans P7 |
| AcsB | ZP_05392956.1 | 255526032 | Clostridium carboxidivorans P7 |
| Orf7 | ZP_05392958.1 | 255526034 | Clostridium carboxidivorans P7 |

The methanogenic archaeon, *Methanosarcina acetivorans*, can also grow on carbon monoxide, exhibits acetyl-CoA synthase/carbon monoxide dehydrogenase activity, and produces both acetate and formate (Lessner et al., *Proc Natl Acad Sci USA* 103:17921-17926 (2006)). This organism contains two sets of genes that encode ACS/CODH activity (Rother and Metcalf *Proc Natl Acad Sci USA* 101:16929-16934 (2004)). The protein sequences of both sets of *M. acetivorans* genes can be identified by the following GenBank accession numbers.

TABLE 7

| Protein | GenBank ID | GI Number | Organism |
| --- | --- | --- | --- |
| AcsC | NP_618736 | 20092661 | Methanosarcina acetivorans |
| AcsD | NP_618735 | 20092660 | Methanosarcina acetivorans |
| AcsF, CooC | NP_618734 | 20092659 | Methanosarcina acetivorans |
| AcsB | NP_618733 | 20092658 | Methanosarcina acetivorans |
| AcsEps | NP_618732 | 20092657 | Methanosarcina acetivorans |
| AcsA | NP_618731 | 20092656 | Methanosarcina acetivorans |
| AcsC | NP_615961 | 20089886 | Methanosarcina acetivorans |
| AcsD | NP_615962 | 20089887 | Methanosarcina acetivorans |
| AcsF, CooC | NP_615963 | 20089888 | Methanosarcina acetivorans |
| AcsB | NP_615964 | 20089889 | Methanosarcina acetivorans |
| AcsEps | NP_615965 | 20089890 | Methanosarcina acetivorans |
| AcsA | NP_615966 | 20089891 | Methanosarcina acetivorans |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as *M. thermoacetica* or hydrogenogenic bacteria such as

*C. hydrogenoformans*. Hypotheses for the existence of two active CODH/ACS operons in *M. acetivorans* include catalytic properties (i.e., Km, Vmax, kcat) that favor carboxidotrophic or aceticlastic growth or differential gene regulation enabling various stimuli to induce CODH/ACS expression (Rother et al., Arch. Microbiol 188:463-472 (2007)). CODH-II were shown to catalyze the formation of NADPH suggesting an anabolic role (Svetlitchnyi et al., J. Bacteriol. 183:5134-5144 (2001)). The crystal structure of the CODH-II is also available (Dobbek et al., Science 293:1281-1285 (2001)). The protein sequences of exemplary CODH and hydrogenase genes can be identified by the following GenBank accession numbers.

TABLE 8

| Protein | GenBank ID | GI Number | Organism |
|---|---|---|---|
| CODH (putative) | YP_430813 | 83590804 | *Moorella thermoacetica* |
| CODH-I (CooS-I) | YP_360644 | 78043418 | *Carboxydothermus hydrogenoformans* |
| CooF | YP_360645 | 78044791 | *Carboxydothermus hydrogenoformans* |
| HypA | YP_360646 | 78044340 | *Carboxydothermus hydrogenoformans* |
| CooH | YP_360647 | 78043871 | *Carboxydothermus hydrogenoformans* |
| CooU | YP_360648 | 78044023 | *Carboxydothermus hydrogenoformans* |
| CooX | YP_360649 | 78043124 | *Carboxydothermus hydrogenoformans* |
| CooL | YP_360650 | 78043938 | *Carboxydothermus hydrogenoformans* |
| CooK | YP_360651 | 78044700 | *Carboxydothermus hydrogenoformans* |
| CooM | YP_360652 | 78043942 | *Carboxydothermus hydrogenoformans* |
| CooM | AAC45116 | 1515466 | *Rhodospirillum rubrum* |
| CooK | AAC45117 | 1515467 | *Rhodospirillum rubrum* |
| CooL | AAC45118 | 1515468 | *Rhodospirillum rubrum* |
| CooX | AAC45119 | 1515469 | *Rhodospirillum rubrum* |
| CooU | AAC45120 | 1515470 | *Rhodospirillum rubrum* |
| CooH | AAC45121 | 1498746 | *Rhodospirillum rubrum* |
| CooF | AAC45122 | 1498747 | *Rhodospirillum rubrum* |
| CODH (CooS) | AAC45123 | 1498748 | *Rhodospirillum rubrum* |
| CooC | AAC45124 | 1498749 | *Rhodospirillum rubrum* |
| CooT | AAC45125 | 1498750 | *Rhodospirillum rubrum* |
| CooJ | AAC45126 | 1498751 | *Rhodospirillum rubrum* |
| CODH-II (CooS-II) | YP_358957 | 78044574 | *Carboxydothermus hydrogenoformans* |
| CooF | YP_358958 | 78045112 | *Carboxydothermus hydrogenoformans* |
| CODH (putative) | ZP_05390164.1 | 255523193 | *Clostridium carboxidivorans* P7 |
| | ZP_05390341.1 | 255523371 | *Clostridium carboxidivorans* P7 |
| | ZP_05391756.1 | 255524806 | *Clostridium carboxidivorans* P7 |
| | ZP_05392944.1 | 255526020 | *Clostridium carboxidivorans* P7 |
| CooF | ZP_05394386.1 | 255527518 | *Clostridium carboxidivorans* P7 |
| CooF | ZP_05394384.1 | 255527516 | *Clostridium carboxidivorans* P7 |
| HypA | ZP_05392031.1 | 255525086 | *Clostridium carboxidivorans* P7 |
| CooH | ZP_05392429.1 | 255525492 | *Clostridium carboxidivorans* P7 |
| CooL | ZP_05392428.1 | 255525491 | *Clostridium carboxidivorans* P7 |
| CooM | ZP_05392434.1 | 255525497 | *Clostridium carboxidivorans* P7 |

In *M. thermoacetica*, *C. hydrogenoformans* and *C. carboxidivorans* P7, additional CODH encoding genes are located outside of the ACS/CODH operons. These enzymes provide a means for extracting electrons (or reducing equivalents) from the conversion of carbon monoxide to carbon dioxide. The reducing equivalents are then passed to accepters such as oxidized ferredoxin, NADP+, water, or hydrogen peroxide to form reduced ferredoxin, NADPH, H2, or water, respectively. In some cases, hydrogenase encoding genes are located adjacent to a CODH. In *Rhodospirillum rubrum*, the encoded CODH/hydrogenase proteins form a membrane-bound enzyme complex that is proposed to be a site where energy, in the form of a proton gradient, is generated from the conversion of CO to CO2 and H2 (Fox et al., J. Bacteriol. 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., PLoS Genet. 1:e65 (2005)). The *C. hydrogenoformans* CODH-I was also shown to exhibit intense CO oxidation and CO2 reduction activities when linked to an electrode (Parkin et al., J. Am. Chem. Soc. 129:10328-10329 (2007)). The genes encoding the *C. hydrogenoformans* CODH-II and CooF, a neighboring protein, were cloned and sequenced (Gonzalez and Robb, FEMS Microbiol Lett. 191:243-247 (2000)). The resulting complex was membrane-bound, although cytoplasmic fractions of Anaerobic growth on synthesis gas and methanol in the absence of an external electron acceptor is conferred upon the host organism with MTR and ACS/CODH activity by providing pyruvate synthesis via pyruvate ferredoxin oxidoreductase (PFOR). The PFOR from *Desulfovibrio africanus* has been cloned and expressed in *E. coli* resulting in an active recombinant enzyme that was stable for several days in the presence of oxygen (Pieulle et al., J. Bacteriol. 179:5684-5692 (1997)). Oxygen stability is relatively uncommon in PFORs and is reported to be conferred by a 60 residue extension in the polypeptide chain of the *D. africanus* enzyme. The *M. thermoacetica* PFOR is also well characterized (Menon and Ragsdale, Biochemistry 36:8484-8494 (1997)) and was shown to have high activity in the direction of pyruvate synthesis during autotrophic growth (Furdui and Ragsdale, J Biol. Chem. 275:28494-28499 (2000)). Further, *E. coli* possesses an uncharacterized open reading frame, ydbK, that encodes a protein that is 51% identical to the *M. thermoacetica* PFOR. Evidence for pyruvate oxidoreductase activity in *E. coli* has been described (Blaschkowski et al., Eur. J. Biochem. 123:563-569 (1982)). Homologs also exist in *C. carboxidivorans* P7. The protein sequences of these exemplary PFOR enzymes are identified by the following GenBank accession numbers shown in Table 9 below. Several additional PFOR enzymes are described in Ragsdale, S. W., Chem. Rev. 103:2333-2346 (2003). Finally, flavodoxin reductases (e.g., fqrB from *Helicobacter pylori* or *Campylobacter jejuni*) (St Maurice et al., *J. Bacteriol.* 189:4764-4773 (2007)) or Rnf-type proteins (Seedorf et al., *Proc. Natl. Acad. Sci. U.S.A.* 105:2128-2133 (2008); and Herrmann, *J. Bacteriol* 190:784-791 (2008)) provide a means to generate NADH or NADPH from the reduced ferredoxin generated by PFOR. These proteins are identified below in Table 9.

TABLE 9

| Protein | GenBank ID | GI Number | Organism |
| --- | --- | --- | --- |
| Por | CAA70873.1 | 1770208 | *Desulfovibrio africanus* |
| Por | YP_428946.1 | 83588937 | *Moorella thermoacetica* |
| YdbK | NP_415896.1 | 16129339 | *Escherichia coli* |
| Por | ZP_05392150.1 | 255525208 | *Clostridium carboxidivorans* P7 |
| Por | ZP_05390930.1 | 255523967 | *Clostridium carboxidivorans* P7 |
| Por | ZP_05394396.1 | 255527529 | *Clostridium carboxidivorans* P7 |
| Por | ZP_05394397.1 | 255527530 | *Clostridium carboxidivorans* P7 |
| FqrB | NP_207955.1 | 15645778 | *Helicobacter pylori* |
| FqrB | YP_001482096.1 | 157414840 | *Campylobacter jejuni* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: the pyruvate decarboxylase (E1), dihydrolipoamide acyltransferase (E2) and dihydrolipoamide dehydrogenase (E3). This enzyme is naturally present in several organisms, including *E. coli* and *S. cerevisiae*. In the *E. coli* enzyme, specific residues in the E1 component are responsible for substrate specificity (Bisswanger, H., *J. Biol. Chem.* 256:815-82 (1981); Bremer, J., *Eur. J. Biochem.* 8:535-540 (1969); Gong et al., *J. Biol. Chem.* 275:13645-13653 (2000)). Enzyme engineering efforts have improved the *E. coli* PDH enzyme activity under anaerobic conditions (Kim et al., *J. Bacteriol.* 190:3851-3858 (2008); Kim et al., *Appl. Environ. Microbiol.* 73:1766-1771 (2007); Zhou et al., *Biotechnol. Lett.* 30:335-342 (2008)). In contrast to the *E. coli* PDH, the *B. subtilis* complex is active and required for growth under anaerobic conditions (Nakano et al., *J. Bacteriol.* 179: 6749-6755 (1997)). The *Klebsiella pneumoniae* PDH, characterized during growth on glycerol, is also active under anaerobic conditions (Menzel et al., *J. Biotechnol.* 56:135-142 (1997)). Crystal structures of the enzyme complex from bovine kidney (Zhou et al., *Proc. Natl. Acad. Sci. U.S.A.* 98:14802-14807 (2001)) and the E2 catalytic domain from *Azotobacter vinelandii* are available (Mattevi et al., *Science* 255:1544-1550 (1992)). Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in *Escherichia coli* encoded by pflB (Knappe and Sawers, *FEMS. Microbiol Rev.* 6:383-398 (1990)), *Lactococcus lactis* (Melchiorsen et al., *Appl. Microbiol. Biotechnol.* 58:338-344 (2002)), and *Streptococcus mutans* (Takahashi-Abbe et al., *Oral. Microbiol Immunol.* 18:293-297 (2003)). *E. coli* possesses an additional pyruvate formate lyase, encoded by tdcE, that catalyzes the conversion of pyruvate or 2-oxobutanoate to acetyl-CoA or propionyl-CoA, respectively (Hesslinger et al., *Mol. Microbiol.* 27:477-492 (1998)). Both pflB and tdcE from *E. coli* require the presence of pyruvate formate lyase activating enzyme, encoded by pflA. Further, a short protein encoded by yfiD in *E. coli* can associate with and restore activity to oxygen-cleaved pyruvate formate lyase (Vey et al., *Proc. Natl. Acad. Sci. U.S.A.* 105:16137-16141 (2008). Note that pflA and pflB from *E. coli* were expressed in *S. cerevisiae* as a means to increase cytosolic acetyl-CoA for butanol production as described in WO/2008/080124]. Additional pyruvate formate lyase and activating enzyme candidates, encoded by pfl and act, respectively, are found in *Clostridium pasteurianum* (Weidner et al., *J. Bacteriol.* 178:2440-2444 (1996)).

Further, different enzymes can be used in combination to convert pyruvate into acetyl-CoA. For example, in *S. cerevisiae*, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase. Acetyl-CoA synthetase is a native enzyme in several other organisms including *E. coli* (Kumari et al., *J. Bacteriol.* 177: 2878-2886 (1995)), *Salmonella enterica* (Starai et al., *Microbiology* 151:3793-3801 (2005); Starai et al., *J. Biol. Chem.* 280:26200-26205 (2005)), and *Moorella thermoacetica* (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Both acetate kinase and phosphotransacetylase are well-studied enzymes in several *Clostridia* and *Methanosarcina thermophila*.

Yet another way of converting pyruvate to acetyl-CoA is via pyruvate oxidase. Pyruvate oxidase converts pyruvate into acetate, using ubiquione as the electron acceptor. In *E. coli*, this activity is encoded by poxB. PoxB has similarity to pyruvate decarboxylase of *S. cerevisiae* and *Zymomonas mobilis*. The enzyme has a thiamin pyrophosphate cofactor (Koland and Gennis, *Biochemistry* 21:4438-4442 (1982)); O'Brien et al., *Biochemistry* 16:3105-3109 (1977); O'Brien and Gennis, *J. Biol. Chem.* 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

Unlike the redox neutral conversion of CO and MeOH to acetyl-CoA or acetate, the production of more highly reduced products such as ethanol, butanol, isobutanol, isopropanol, 1,4-butanediol, succinic acid, fumaric acid, malic acid, 4-hydroxybutyric acid, 3-hydroxypropionic acid, lactic acid, adipic acid, 6-aminocaproic acid, hexamethylenediamine, 3-hydroxyisobutyric acid, 2-hydroxyisobutyric acid, methacrylic acid, and acrylic acid at the highest possible yield requires the extraction of additional reducing equivalents from both CO and $H_2$ (for example, see ethanol formation in FIG. 2A). Specifically, reducing equivalents (e.g., 2 [H] in FIG. 2) are obtained by the conversion of CO and water to $CO_2$ via carbon monoxide dehydrogenase or directly from the activity of a hydrogen-utilizing hydrogenase which transfers electrons from $H_2$ to an acceptor such as ferredoxin, flavodoxin, $FAD^+$, $NAD^+$, or $NADP^+$.

Native to *E. coli* and other enteric bacteria are multiple genes encoding up to four hydrogenases (Sawers, G., *Antonie Van Leeuwenhoek* 66:57-88 (1994); Sawers et al., *J. Bacteriol.* 164:1324-1331 (1985); Sawers and Boxer, *Eur. J. Biochem.* 156:265-275 (1986); Sawers et al., *J. Bacteriol.* 168: 398-404 (1986)). Given the multiplicity of enzyme activities *E. coli* or another host organism can provide sufficient hydrogenase activity to split incoming molecular hydrogen and reduce the corresponding acceptor. Among the endogenous hydrogen-lyase enzymes of *E. coli* are hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase activity in *E. coli* is also dependent upon the expression of the hyp genes whose corresponding proteins are involved in the assembly of the hydrogenase complexes (Jacobi et al., *Arch. Microbiol* 158: 444-451 (1992); Rangarajan et al., *J. Bacteriol.* 190:1447-1458 (2008)). The *M. thermoacetica* hydrogenases are suitable for a host that lacks sufficient endogenous hydrogenase activity. *M. thermoacetica* can grow with $CO_2$ as the exclusive carbon source indicating that reducing equivalents are extracted from $H_2$ to enable acetyl-CoA synthesis via the Wood-Ljungdahl pathway (Drake, H. L., *J. Bacteriol.* 150: 702-709 (1982); Drake and Daniel, *Res Microbiol* 155:869-883 (2004); Kellum and Drake, *J. Bacteriol.* 160:466-469 (1984)) (see FIG. 2A). *M. thermoacetica* has homologs to several hyp, hyc, and hyf genes from *E. coli*. These protein sequences encoded for by these genes are identified by the following GenBank accession numbers. In addition, several gene clusters encoding hydrogenase functionality are present in *M. thermoacetica* and their corresponding protein sequences are also provided below in Table 10.

TABLE 10

| Protein | GenBank ID | GI Number | Organism |
|---|---|---|---|
| HypA | NP_417206 | 16130633 | *Escherichia coli* |
| HypB | NP_417207 | 16130634 | *Escherichia coli* |
| HypC | NP_417208 | 16130635 | *Escherichia coli* |
| HypD | NP_417209 | 16130636 | *Escherichia coli* |
| HypE | NP_417210 | 226524740 | *Escherichia coli* |
| HypF | NP_417192 | 16130619 | *Escherichia coli* |

Proteins in *M. thermoacetica* whose genes are homologous to the *E. coli* hyp genes are shown below in Table 11. Hydrogenase 3 proteins are listed in Table 12. Hydrogenase 4 proteins are shown in Table 13.

TABLE 11

| Protein | GenBank ID | GI Number | Organism |
|---|---|---|---|
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |

TABLE 12

| Protein | GenBank ID | GI Number | Organism |
|---|---|---|---|
| HycA | NP_417205 | 16130632 | *Escherichia coli* |
| HycB | NP_417204 | 16130631 | *Escherichia coli* |
| HycC | NP_417203 | 16130630 | *Escherichia coli* |
| HycD | NP_417202 | 16130629 | *Escherichia coli* |
| HycE | NP_417201 | 16130628 | *Escherichia coli* |
| HycF | NP_417200 | 16130627 | *Escherichia coli* |
| HycG | NP_417199 | 16130626 | *Escherichia coli* |
| HycH | NP_417198 | 16130625 | *Escherichia coli* |
| HycI | NP_417197 | 16130624 | *Escherichia coli* |

TABLE 13

| Protein | GenBank ID | GI Number | Organism |
|---|---|---|---|
| HyfA | NP_416976 | 90111444 | *Escherichia coli* |
| HyfB | NP_416977 | 16130407 | *Escherichia coli* |
| HyfC | NP_416978 | 90111445 | *Escherichia coli* |
| HyfD | NP_416979 | 16130409 | *Escherichia coli* |
| HyfE | NP_416980 | 16130410 | *Escherichia coli* |
| HyfF | NP_416981 | 16130411 | *Escherichia coli* |
| HyfG | NP_416982 | 16130412 | *Escherichia coli* |
| HyfH | NP_416983 | 16130413 | *Escherichia coli* |
| HyfI | NP_416984 | 16130414 | *Escherichia coli* |
| HyfJ | NP_416985 | 90111446 | *Escherichia coli* |
| HyfR | NP_416986 | 90111447 | *Escherichia coli* |

Proteins in *M. thermoacetica* whose genes are homologous to the *E. coli* hyc and/or hyf genes are shown in Table 14 below. Additional hydrogenase-encoding gene clusters in *M. thermoacetica* are shown in Table 15.

TABLE 14

| Protein | GenBank ID | GI Number | Organism |
|---|---|---|---|
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |
| Moth_2192 | YP_431024 | 83591015 | *Moorella thermoacetica* |

TABLE 15

| Protein | GenBank ID | GI Number | Organism |
|---|---|---|---|
| Moth_0439 | YP_429313 | 83589304 | *Moorella thermoacetica* |
| Moth_0440 | YP_429314 | 83589305 | *Moorella thermoacetica* |
| Moth_0441 | YP_429315 | 83589306 | *Moorella thermoacetica* |
| Moth_0442 | YP_429316 | 83589307 | *Moorella thermoacetica* |
| Moth_0809 | YP_429670 | 83589661 | *Moorella thermoacetica* |
| Moth_0810 | YP_429671 | 83589662 | *Moorella thermoacetica* |
| Moth_0811 | YP_429672 | 83589663 | *Moorella thermoacetica* |
| Moth_0812 | YP_429673 | 83589664 | *Moorella thermoacetica* |
| Moth_0814 | YP_429674 | 83589665 | *Moorella thermoacetica* |
| Moth_0815 | YP_429675 | 83589666 | *Moorella thermoacetica* |
| Moth_0816 | YP_429676 | 83589667 | *Moorella thermoacetica* |
| Moth_1193 | YP_430050 | 83590041 | *Moorella thermoacetica* |
| Moth_1194 | YP_430051 | 83590042 | *Moorella thermoacetica* |
| Moth_1195 | YP_430052 | 83590043 | *Moorella thermoacetica* |
| Moth_1196 | YP_430053 | 83590044 | *Moorella thermoacetica* |
| Moth_1717 | YP_430562 | 83590553 | *Moorella thermoacetica* |
| Moth_1718 | YP_430563 | 83590554 | *Moorella thermoacetica* |
| Moth_1719 | YP_430564 | 83590555 | *Moorella thermoacetica* |
| Moth_1883 | YP_430726 | 83590717 | *Moorella thermoacetica* |
| Moth_1884 | YP_430727 | 83590718 | *Moorella thermoacetica* |
| Moth_1885 | YP_430728 | 83590719 | *Moorella thermoacetica* |
| Moth_1886 | YP_430729 | 83590720 | *Moorella thermoacetica* |
| Moth_1887 | YP_430730 | 83590721 | *Moorella thermoacetica* |

TABLE 15-continued

| Protein | GenBank ID | GI Number | Organism |
| --- | --- | --- | --- |
| Moth_1888 | YP_430731 | 83590722 | Moorella thermoacetica |
| Moth_1452 | YP_430305 | 83590296 | Moorella thermoacetica |
| Moth_1453 | YP_430306 | 83590297 | Moorella thermoacetica |
| Moth_1454 | YP_430307 | 83590298 | Moorella thermoacetica |

Isopropanol production is achieved in recombinant *E. coli* following expression of two heterologous genes from *C. acetobutylicum* (thl and adc encoding acetoacetyl-CoA thiolase and acetoacetate decarboxylase, respectively) and one from *C. beijerinckii* (adh encoding a secondary alcohol dehydrogenase), along with the increased expression of the native atoA and atoD genes which encode acetoacetyl-CoA:acetate: CoA transferase activity (Hanai et al., *Appl Environ Microbiol* 73:7814-7818 (2007)).

Acetoacetyl-CoA thiolase converts two molecules of acetyl-CoA into one molecule each of acetoacetyl-CoA and CoA. Such a conversion is the first step for isopropanol, 4-hydroxybutyrate, and 1,4-butanediol synthesis from acetyl-CoA, as shown in FIGS. 2 and 3. Exemplary acetoacetyl-CoA thiolase enzymes include the gene products of atoB from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007); Winzer et al., *J. Mol. Microbiol Biotechnol* 2:531-541 (2000), and ERG10 from *S. cerevisiae* Hiser et al., *J. Biol. Chem.* 269:31383-31389 (1994)).

TABLE 16

| Protein | GenBank ID | GI Number | Organism |
| --- | --- | --- | --- |
| AtoB | NP_416728 | 16130161 | Escherichia coli |
| ThlA | NP_349476.1 | 15896127 | Clostridium acetobutylicum |
| ThlB | NP_149242.1 | 15004782 | Clostridium acetobutylicum |
| ERG10 | NP_015297 | 6325229 | Saccharomyces cerevisiae |

The conversion of acetoacetyl-CoA to acetoacetate or of 4-hydroxybutyryl-CoA to 4-hydroxybutyrate can be carried out by an acetoacetyl-CoA transferase or 4-hydroxybutyryl-CoA transferase, respectively. These enzymes conserve the energy stored in the CoA-ester bonds of acetoacetyl-CoA and 4-hydroxybutyryl-CoA. Many transferases have broad specificity and thus can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. Acetoacetyl-CoA transferase catalyzes the conversion of acetoacetyl-CoA to acetoacetate while transferring the CoA moiety to a CoA acceptor molecule. Several exemplary transferase enzymes capable of catalyzing this transformation are provided below. These enzymes either naturally exhibit the desired acetoacetyl-CoA transferase activity or they can be engineered via directed evolution to accept acetoacetyl-CoA as a substrate with increased efficiency. Such enzymes, either naturally or following directed evolution, are also suitable for catalyzing the conversion of 4-hydroxybutyryl-CoA to 4-hydroxybutyrate via a transferase mechanism.

In one embodiment an exemplary acetoacetyl-CoA transferase is acetoacetyl-CoA:acetate-CoA transferase. This enzyme naturally converts acetate to acetyl-CoA while converting acetoacetyl-CoA to acetoacetate. In another embodiment, a succinyl-CoA:3-ketoacid CoA transferase (SCOT) catalyzes the conversion of the 3-ketoacyl-CoA, acetoacetyl-CoA, to the 3-ketoacid, acetoacetate.

Acetoacetyl-CoA:acetyl-CoA transferase naturally converts acetoacetyl-CoA and acetate to acetoacetate and acetyl-CoA. This enzyme can also accept 3-hydroxybutyryl-CoA as a substrate or could be engineered to do so. Exemplary enzymes include the gene products of atoAD from *E. coli* (Hanai et al., *Appl Environ Microbiol.* 73:7814-7818 (2007)), ctfAB from *C. acetobutylicum* (Jojima et al., *Appl Microbiol Biotechnol.* 77:1219-1224 (2008)), and ctfAB from *Clostridium saccharoperbutylacetonicum* (Kosaka et al., *Biosci. Biotechnol Biochem.* 71:58-68 (2007)). Information related to these proteins and genes is shown below:

TABLE 17

| Protein | GENBANK ID | GI NUMBER | ORGANISM |
| --- | --- | --- | --- |
| AtoA | P76459.1 | 2492994 | Escherichia coli |
| AtoD | P76458.1 | 2492990 | Escherichia coli |
| CtfA | NP_149326.1 | 15004866 | Clostridium acetobutylicum |
| CtfB | NP_149327.1 | 15004867 | Clostridium acetobutylicum |
| CtfA | AAP42564.1 | 31075384 | Clostridium saccharoperbutylacetonicum |
| CtfB | AAP42565.1 | 31075385 | Clostridium saccharoperbutylacetonicum |

Succinyl-CoA:3-ketoacid-CoA transferase naturally converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al. *J. Biol. Chem.* 272:25659-25667 (1997)), *Bacillus subtilis* (Stols et al., *Protein. Expr. Purif.* 53:396-403 (2007)), and *Homo sapiens* (Fukao et al. *Genomics* 68:144-151 (2000); Tanaka et al., *Mol. Hum. Reprod.* 8:16-23 (2002)). Information related to these proteins and genes is shown below:

TABLE 18

| Protein | GENBANK ID | GI NUMBER | ORGANISM |
| --- | --- | --- | --- |
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |
| OXCT1 | NP_000427 | 4557817 | Homo sapiens |
| OXCT2 | NP_071403 | 11545841 | Homo sapiens |

Additional suitable acetoacetyl-CoA and 4-hydroxybutyryl-CoA transferases are encoded by the gene products of cat1, cat2, and cat3 of *Clostridium kluyveri*. These enzymes have been shown to exhibit succinyl-CoA, 4-hydroxybutyryl-CoA, and butyryl-CoA transferase activity, respectively (Seedorf et al., *Proc. Natl. Acad. Sci. U.S.A.* 105:2128-2133 (2008); Sohling and Gottschalk, *J. Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA:acetoacetate CoA-transferase. Exemplary enzymes can be found in *Fusobacterium nucleatum* (Barker et al., *J. Bacteriol.* 152(1):201-7 (1982)), *Clostridium* SB4 (Barker et al., *J. Biol. Chem.* 253(4):1219-25 (1978)), and *Clostridium acetobutylicum* (Wiesenborn et al., *Appl. Environ. Microbiol.* 55(2):323-9 (1989)). Although specific gene sequences were not provided for butyryl-CoA:acetoacetate CoA-transferase in these references, the genes FN0272 and FN0273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity.

FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyrmonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below:

TABLE 19

| Protein | GENBANK ID | GI NUMBER | ORGANISM |
|---|---|---|---|
| Cat1 | P38946.1 | 729048 | *Clostridium kluyveri* |
| Cat2 | P38942.2 | 1705614 | *Clostridium kluyveri* |
| Cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Acetoacetyl-CoA can be hydrolyzed to acetoacetate by acetoacetyl-CoA hydrolase. Similarly, 4-hydroxybutyryl-CoA can be hydrolyzed to 4-hydroxybutyate by 4-hydroxybutyryl-CoA hydrolase. Many CoA hydrolases (EC 3.1.2.1) have broad substrate specificity and are suitable enzymes for these transformations either naturally or following enzyme engineering. Though the sequences were not reported, several acetoacetyl-CoA hydrolases were identified in the cytosol and mitochondrion of the rat liver (Aragon and Lowenstein, *J. Biol. Chem.* 258(8):4725-4733 (1983)). Additionally, an enzyme from *Rattus norvegicus* brain (Robinson et al., *Biochem. Biophys. Res. Commun.* 71:959-965 (1976)) can react with butyryl-CoA, hexanoyl-CoA and malonyl-CoA. The acot12 enzyme from the rat liver was shown to hydrolyze C2 to C6 acyl-CoA molecules (Suematsu et al., *Eur. J. Biochem.* 268:2700-2709 (2001)). Though its sequence has not been reported, the enzyme from the mitochondrion of the pea leaf showed activity on acetyl-CoA, propionyl-CoA, butyryl-CoA, palmitoyl-CoA, oleoyl-CoA, succinyl-CoA, and crotonyl-CoA (Zeiher and Randall, *Plant. Physiol.* 94:20-27 (1990)). Additionally, a glutaconate CoA-transferase from *Acidaminococcus fermentans* was transformed by site-directed mutagenesis into an acyl-CoA hydrolase with activity on glutaryl-CoA, acetyl-CoA and 3-butenoyl-CoA (Mack and Buckel, *FEBS Lett.* 405:209-212 (1997)). This indicates that the enzymes encoding acetoacetyl-CoA transferases and 4-hydroxybutyryl-CoA transferases can also be used as hydrolases with certain mutations to change their function. The acetyl-CoA hydrolase, ACH1, from *S. cerevisiae* represents another candidate hydrolase (Buu et al., *J. Biol. Chem.* 278:17203-17209 (2003)). Information related to these proteins and genes is shown below:

TABLE 20

| Protein | GENBANK ID | GI NUMBER | ORGANISM |
|---|---|---|---|
| Acot12 | NP_570103.1 | 18543355 | *Rattus norvegicus* |
| GctA | CAA57199 | 559392 | *Acidaminococcus fermentans* |
| GctB | CAA57200 | 559393 | *Acidaminococcus fermentans* |
| ACH1 | NP_009538 | 6319456 | *Saccharomyces cerevisiae* |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)) and the closest *E. coli* homolog, tesB, which can also hydrolyze a broad range of CoA thioesters (Naggert et al., *J. Biol. Chem.* 266:11044-11050 (1991)) including 3-hydroxybutyryl-CoA (Tseng et al., *Appl. Environ. Microbiol.* 75(10):3137-3145 (2009)). A similar enzyme has also been characterized in the rat liver (Deana, *Biochem. Int.* 26:767-773 (1992)). Other potential *E. coli* thioester hydrolases include the gene products of tesA (Bonner and Bloch, *J. Biol. Chem.* 247:3123-3133 (1972)), ybgC (Kuznetsova et al., *FEMS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 189:7112-7126 (2007)). Information related to these proteins and genes is shown below:

TABLE 21

| Protein | GENBANK ID | GI NUMBER | ORGANISM |
|---|---|---|---|
| Acot8 | CAA15502 | 3191970 | *Homo sapiens* |
| TesB | NP_414986 | 16128437 | *Escherichia coli* |
| Acot8 | NP_570112 | 51036669 | *Rattus norvegicus* |
| TesA | NP_415027 | 16128478 | *Escherichia coli* |
| YbgC | NP_415264 | 16128711 | *Escherichia coli* |
| PaaI | NP_415914 | 16129357 | *Escherichia coli* |
| YbdB | NP_415129 | 16128580 | *Escherichia coli* |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J. Biol. Chem.* 269:14248-14253 (1994)). Genes encoding this enzyme include hibch of *Rattus norvegicus* (Shimomura et al., supra (1994); Shimomura et al., *Methods Enzymol.* 324:229-240 (2000)) and *Homo sapiens* (Shimomura et al., supra (1994). Candidate genes by sequence homology include hibch of *Saccharomyces cerevisiae* and BC_2292 of *Bacillus cereus*. BC_2292 was shown to demonstrate 3-hydroxybutyryl-CoA hydrolase activity and function as part of a pathway for 3-hydroxybutyrate synthesis when engineered into *Escherichia coli* (Lee et al., *Appl. Microbiol. Biotechnol.* 79:633-641 (2008)). Information related to these proteins and genes is shown below:

TABLE 22

| Protein | GENBANK ID | GI NUMBER | ORGANISM |
|---|---|---|---|
| Hibch | Q5XIE6.2 | 146324906 | *Rattus norvegicus* |
| Hibch | Q6NVY1.2 | 146324905 | *Homo sapiens* |
| Hibch | P28817.2 | 2506374 | *Saccharomyces cerevisiae* |
| BC_2292 | AP09256 | 29895975 | *Bacillus cereus* ATCC 14579 |

The hydrolysis of acetoacetyl-CoA or 4-hydroxybutyryl-CoA can alternatively be carried out by a single enzyme or enzyme complex that exhibits acetoacetyl-CoA or 4-hydroxybutyryl-CoA synthetase activity. This activity enables the net hydrolysis of the CoA-ester of either molecule, and in some cases, results in the simultaneous generation of ATP. For example, the product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Gruys et al., U.S. Pat. No. 5,958,745, filed Sep. 28, 1999). Information related to these proteins and genes is shown below:

TABLE 23

| Protein | GENBANK ID | GI NUMBER | ORGANISM |
|---|---|---|---|
| SucC | NP_415256.1 | 16128703 | *Escherichia coli* |
| SucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |

Additional exemplary CoA-ligases include the rat dicarboxylate-CoA ligase for which the sequence is yet uncharacterized (Vamecq et al., *Biochemical J.* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacilis subtilis* (Bower et al., *J. Bacteriol.* 178(14):4122-4130 (1996)). Additional candidate enzymes are acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)), which naturally catalyze the ATP-dependant conversion of acetoacetate into acetoacetyl-CoA. 4-Hydroxybutyryl-CoA synthetase activity has been demonstrated in *Metallosphaera sedula* (Berg et al., *Science* 318: 1782-1786 (2007)). This function has been tentatively assigned to the Msed_1422 gene. Information related to these proteins and genes is shown below:

TABLE 24

| Protein | GENBANK ID | GI NUMBER | ORGANISM |
|---|---|---|---|
| Phl | CAJ15517.1 | 77019264 | *Penicillium chrysogenum* |
| PhlB | ABS19624.1 | 152002983 | *Penicillium chrysogenum* |
| PaaF | AAC24333.2 | 22711873 | *Pseudomonas putida* |
| BioW | NP_390902.2 | 50812281 | *Bacillus subtilis* |
| AACS | NP_084486.1 | 21313520 | *Mus musculus* |

TABLE 24-continued

| Protein | GENBANK ID | GI NUMBER | ORGANISM |
|---|---|---|---|
| AACS | NP_076417.2 | 31982927 | *Homo sapiens* |
| Msed_1422 | YP_001191504 | 146304188 | *Metallosphaera sedula* |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF 1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus, H. marismortui* and *P. aerophilum* have all been cloned, functionally expressed, and characterized in *E. coli* (Musfeldt et al., supra; Brasen et al., supra (2004)). Information related to these proteins and genes is shown below:

TABLE 25

| Protein | GENBANK ID | GI NUMBER | ORGANISM |
|---|---|---|---|
| AF1211 | NP_070039.1 | 11498810 | *Archaeoglobus fulgidus* DSM 4304 |
| Scs | YP_135572.1 | 55377722 | *Haloarcula marismortui* ATCC 43049 |
| PAE3250 | NP_560604.1 | 18313937 | *Pyrobaculum aerophilum* str. IM2 |

An alternative method for removing the CoA moiety from acetoacetyl-CoA or 4-hydroxybutyryl-CoA is to apply a pair of enzymes such as a phosphate-transferring acyltransferase and a kinase to impart acetoacetyl-CoA or 4-hydroxybutyryl-CoA synthetase activity. Exemplary names for these enzymes include phosphotrans-4-hydroxybutyrylase/4-hydroxybutyrate kinase, which can remove the CoA moiety from 4-hydroxybutyryl-CoA, and phosphotransacetoacetylase/acetoacetate kinase which can remove the CoA moiety from acetoacetyl-CoA. This general activity enables the net hydrolysis of the CoA-ester of either molecule with the simultaneous generation of ATP. For example, the butyrate kinase (buk)/phosphotransbutyrylase (ptb) system from *Clostridium acetobutylicum* has been successfully applied to remove the CoA group from 3-hydroxybutyryl-CoA when functioning as part of a pathway for 3-hydroxybutyrate synthesis (Tseng et al., *Appl. Environ. Microbiol.* 75(10):3137-3145 (2009)). Specifically, the ptb gene from *C. acetobutylicum* encodes an enzyme that can convert an acyl-CoA into an acyl-phosphate (Walter et al. *Gene* 134(1): p. 107-11 (1993)); Huang et al. *J Mol Microbiol Biotechnol* 2(1): p. 33-38 (2000). Additional ptb genes can be found in butyrate-producing bacterium L2-50 (Louis et al. *J. Bacteriol.* 186:2099-2106 (2004)) and *Bacillus megaterium* (Vazquez et al. *Curr.*

Microbiol 42:345-349 (2001)). Additional exemplary phosphate-transferring acyltransferases include phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Information related to these proteins and genes is shown below:

TABLE 26

| Protein | GENBANK ID | GI NUMBER | ORGANISM |
|---|---|---|---|
| Pta | NP_416800.1 | 16130232 | *Escherichia coli* |
| Ptb | NP_349676 | 15896327 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

Exemplary kinases include the *E. coli* acetate kinase, encoded by ackA (Skarstedt and Silverstein *J. Biol. Chem.* 251:6775-6783 (1976)), the *C. acetobutylicum* butyrate kinases, encoded by buk1 and buk2 ((Walter et al. *Gene* 134(1):107-111 (1993); Huang et al. *J. Mol. Microbiol. Biotechnol.* 2(1):33-38 (2000)), and the *E. coli* gamma-glutamyl kinase, encoded by proB (Smith et al. *J. Bacteriol.* 157:545-551 (1984)). These enzymes phosphorylate acetate, butyrate, and glutamate, respectively. The ackA gene product from *E. coli* also phosphorylates propionate (Hesslinger et al. *Mol. Microbiol.* 27:477-492 (1998)). Information related to these proteins and genes is shown below:

TABLE 27

| Protein | GENBANK ID | GI NUMBER | ORGANISM |
|---|---|---|---|
| AckA | NP_416799.1 | 16130231 | *Escherichia coli* |
| Buk1 | NP_349675 | 15896326 | *Clostridium acetobutylicum* |
| Buk2 | Q97II1 | 20137415 | *Clostridium acetobutylicum* |
| ProB | NP_414777.1 | 16128228 | *Escherichia coli* |

Acetoacetate decarboxylase converts acetoacetate into carbon dioxide and acetone. Exemplary acetoacetate decarboxylase enzymes are encoded by the gene products of adc from *C. acetobutylicum* (Petersen and Bennett, *Appl Environ. Microbiol* 56:3491-3498 (1990)) and adc from *Clostridium saccharoperbutylacetonicum* (Kosaka, et al., *Biosci. Biotechnol Biochem.* 71:58-68 (2007)). The enzyme from *C. beijerinkii* can be inferred from sequence similarity. These proteins are identified below in Table 28.

TABLE 28

| Protein | GenBank ID | GI Number | Organism |
|---|---|---|---|
| Adc | NP_149328.1 | 15004868 | *Clostridium acetobutylicum* |
| Adc | AAP42566.1 | 31075386 | *Clostridium saccharoperbutylacetonicum* |
| Adc | YP_001310906.1 | 150018652 | *Clostridium beijerinckii* |

The final step in the isopropanol synthesis pathway involves the reduction of acetone to isopropanol. Exemplary alcohol dehydrogenase enzymes capable of this transformation include adh from *C. beijerinckii* (Hanai et al., *Appl. Environ. Microbiol.* 73:7814-7818 (2007); Jojima et al.,*Appl. Microbiol. Biotechnol.* 77:1219-1224 (2008)) and adh from *Thermoanaerobacter brockii* (Hanai et al., *Appl. Environ. Microbiol.* 73:7814-7818 (2007); Peretz et al., *Anaerobe* 3:259-270 (1997)). Additional characterized enzymes include alcohol dehydrogenases from *Ralstonia eutropha* (formerly *Alcaligenes eutrophus*) (Steinbuchel and Schlegel et al., *Eur. J. Biochem.* 141:555-564 (1984)) and *Phytomonas* species (Uttaro and Opperdoes et al., *Mol. Biochem. Parasitol.* 85:213-219 (1997)).

TABLE 29

| Protein | GenBank ID | GI Number | Organism |
|---|---|---|---|
| Adh | P14941.1 | 113443 | *Thermoanaerobobacter brockii* |
| Adh | AAA23199.2 | 60592974 | *Clostridium beijerinckii* |
| Adh | YP_299391.1 | 73539024 | *Ralstonia eutropha* |
| iPDH | AAP39869.1 | 31322946 | *Phtomonas* sp. |

Exemplary 3-hydroxyacyl dehydrogenases which convert acetoacetyl-CoA to 3-hydroxybutyryl-CoA include hbd from *C. acetobutylicum* (Boynton et al., *J. Bacteriol.* 178:3015-3024 (1996)), hbd from *C. beijerinckii* (Colby and Chen et al., *Appl. Environ. Microbiol.* 58:3297-3302 (1992)), and a number of similar enzymes from *Metallosphaera sedula* (Berg et al., *Science* 318:1782-1786 (2007)).

TABLE 29

| Protein | GenBank ID | GI Number | Organism |
|---|---|---|---|
| hbd | NP_349314.1 | 15895965 | *Clostridium acetobutylicum* |
| hbd | AAM14586.1 | 20162442 | *Clostridium beijerinckii* |
| Msed_1423 | YP_001191505 | 146304189 | *Metallosphaera sedula* |
| Msed_0399 | YP_001190500 | 146303184 | *Metallosphaera sedula* |
| Msed_0389 | YP_001190490 | 146303174 | *Metallosphaera sedula* |
| Msed_1993 | YP_001192057 | 146304741 | *Metallosphaera sedula* |

The gene product of crt from *C. acetobutylicum* catalyzes the dehydration of 3-hydroxybutyryl-CoA to crotonyl-CoA (Atsumi et al., *Metab. Eng.* (2007); Boynton et al., *J. Bacteriol.* 178:3015-3024 (1996)). Further, enoyl-CoA hydratases are reversible enzymes and thus suitable candidates for catalyzing the dehydration of 3-hydroxybutyryl-CoA to crotonyl-CoA. The enoyl-CoA hydratases, phaA and phaB, of *P. putida* are believed to carry out the hydroxylation of double bonds during phenylacetate catabolism (Olivera et al., *Proc. Nat. Acad. Sci. U.S.A.* 95:6419-6424 (1998)). The paaA and paaB from *P. fluorescens* catalyze analogous transformations (Olivera et al., *Proc. Nat. Acad. Sci. U.S.A.* 95:6419-6424 (1998)). Lastly, a number of *Escherichia coli* genes have been shown to demonstrate enoyl-CoA hydratase functionality including maoC, paaF, and paaG (Ismail et al., *Eur. J. Biochem.* 270:3047-3054 (2003); Park and Lee, *J. Bacteriol.* 185:5391-5397 (2003); Park and Lee, *Appl. Biochem. Biotechnol* 113-116:335-346 (2004); Park and Yup, *Biotechnol. Bioeng.* 86:681-686 (2004)).

TABLE 30

| Protein | GenBank ID | GI Number | Organism |
|---|---|---|---|
| crt | NP_349318.1 | 15895969 | *Clostridium acetobutylicum* |
| paaA | NP_745427.1 | 26990002 | *Pseudomonas putida* |
| paaB | NP_745426.1 | 26990001 | *Pseudomonas putida* |
| phaA | ABF82233.1 | 106636093 | *Pseudomonas fluorescens* |
| phaB | ABF82234.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Several enzymes that naturally catalyze the reverse reaction (i.e., the dehydration of 4-hydroxybutyryl-CoA to crotonoyl-CoA) in vivo have been identified in numerous species.

This transformation is used for 4-aminobutyrate fermentation by *Clostridium aminobutyricum* (Scherf and Buckel, *Eur. J. Biochem.* 215:421-429 (1993)) and succinate-ethanol fermentation by *Clostridium kluyveri* (Scherf et al., *Arch. Microbiol.* 161:239-245 (1994)). The transformation is also a step in Archaea, for example, *Metallosphaera sedula*, as part of the 3-hydroxypropionate/4-hydroxybutyrate autotrophic carbon dioxide assimilation pathway (Berg et al., *Science* 318: 1782-1786 (2007)). This pathway uses the hydration of crotonoyl-CoA to form 4-hydroxybutyryl-CoA. The reversibility of 4-hydroxybutyryl-CoA dehydratase is well-documented (Friedrich et al., *Angew. Chem. Int. Ed. Engl.* 47:3254-3257 (2008); Muh et al., *Eur. J. Biochem.* 248:380-384 (1997); Muh et al., *Biochemistry* 35:11710-11718 (1996)) and the equilibrium constant has been reported to be about 4 on the side of crotonoyl-CoA (Scherf and Buckel, *Eur. J. Biochem.* 215:421-429 (1993)). This indicates that the downstream 4-hydroxybutyryl-CoA dehydrogenase keeps the 4-hydroxybutyryl-CoA concentration low so as to not create a thermodynamic bottleneck at crotonyl-CoA.

TABLE 31

| Protein | GenBank ID | GI Number | Organism |
|---|---|---|---|
| AbfD | CAB60035 | 70910046 | *Clostridium aminobutyricum* |
| AbfD | YP_001396399 | 153955634 | *Clostridium kluyveri* |
| Msed_1321 | YP_001191403 | 146304087 | *Metallosphaera sedula* |
| Msed_1220 | YP_001191305 | 146303989 | *Metallosphaera sedula* |

Alcohol-forming 4-hydroxybutyryl-CoA reductase enzymes catalyze the 2 reduction steps required to form 1,4-butanediol from 4-hydroxybutyryl-CoA. Exemplary 2-step oxidoreductases that convert an acyl-CoA to alcohol include those that transform substrates such as acetyl-CoA to ethanol (e.g., adhE from *E. coli* (Kessler et al., *FEBS. Lett.* 281:59-63 (1991)) and butyryl-CoA to butanol (e.g. adhE2 from *C. acetobutylicum* (Fontaine et al., *J. Bacteriol.* 184:821-830 (2002)). The adhE2 enzyme from *C. acetobutylicum* was specifically shown in ref. Burk et al., WO/2008/115840 (2008). to produce BDO from 4-hydroxybutyryl-CoA. In addition to reducing acetyl-CoA to ethanol, the enzyme encoded by adhE in *Leuconostoc mesenterokles* has been shown to oxide the branched chain compound isobutyraldehyde to isobutyryl-CoA (Kazahaya et al., *J. Gen. Appl. Microbiol.* 18:43-55 (1972); Koo et al., *Biotechnol. Lett.* 27:505-510 (2005)).

TABLE 32

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.* 184:2404-2410 (2000); Strauss and Fuchs, *Eur. J. Biochem.* 215:633-643 (1993)). This enzyme, with a mass of 300 kDa, is highly substrate-specific and shows little sequence similarity to other known oxidoreductases (Hugler et al., *J. Bacteriol.* 184:2404-2410 (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

TABLE 33

| Protein | GenBank ID | GI Number | Organism |
|---|---|---|---|
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

An alternative route to BDO from 4-hydroxybutyryl-CoA involves first reducing this compound to 4-hydroxybutanal. Several acyl-CoA dehydrogenases are capable of reducing an acyl-CoA to its corresponding aldehyde. Exemplary genes that encode such enzymes include the *Acinetobacter calcoaceticus* acr1 encoding a fatty acyl-CoA reductase (Reiser and Somerville, *J. Bacteriol.* 179:2969-2975 (1997)), the *Acinetobacter* sp. M-1 fatty acyl-CoA reductase (Ishige et al., *Appl. Environ. Microbiol.* 68:1192-1195 (2002)), and a CoA- and NADP-dependent succinate semialdehyde dehydrogenase encoded by the sucD gene in *Clostridium kluyveri* (Sohling and Gottschalk, *J. Bacteriol.* 178:871-880 (1996)). SucD of *P. gingivalis* is another succinate semialdehyde dehydrogenase (Takahashi et al., *J. Bacteriol.* 182:4704-4710 (2000)). These succinate semialdehyde dehydrogenases were specifically shown in ref. Burk et al., WO/2008/115840 (2008) to convert 4-hydroxybutyryl-CoA to 4-hydroxybutanal as part of a pathway to produce 1,4-butanediol. The enzyme acylating acetaldehyde dehydrogenase in *Pseudomonas* sp, encoded by bphG, is yet another capable enzyme as it has been demonstrated to oxidize and acylate acetaldehyde, propionaldehyde, butyraldehyde, isobutyraldehyde and formaldehyde (Powlowski et al., *J. Bacteriol.* 175:377-385 (1993)).

TABLE 34

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in theimoacidophilic archael bacteria (Berg et al., *Science* 318:1782-1786 (2007); Thauer, R. K. *Science* 318:1732-1733 (2007)). The enzyme utilizes NADPH as a cofactor and has been characterized in *Metallosphaera* and *Sulfolobus* spp (Alber et al., *J. Bacteriol.* 188:8551-8559 (2006); Hugler et al., *J. Bacteriol.* 184:2404-2410 (2002)). The enzyme is encoded by Msed_0709 in *Metallosphaera sedula* (Alber et al., *J. Bacteriol.* 188:8551-8559 (2006); Berg et al., *Science* 318:1782-1786 (2007)). A gene encoding a malonyl-CoA reductase from *Sulfolobus tokodaii* was cloned and heterologously expressed in *E. coli*

(Alber et al., *J. Bacteriol.* 188:8551-8559 (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. Yet another gene for CoA-acylating aldehyde dehydrogenase is the ald gene from *Clostridium beijerinckii* (Toth, *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, *Appl. Environ. Microbiol.* 65:4973-4980 (1999). These proteins are identified below in Table 35.

TABLE 35

| Protein | GenBank ID | GI Number | Organism |
| --- | --- | --- | --- |
| Msed_0709 | YP_001190808.1 | 146303492 | *Metallosphaera sedula* |
| Mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |
| eutE | P77445 | 2498347 | *Escherichia coli* |

4-Hydroxybutyryl-CoA can also be converted to 4-hydroxybutanal in several enzymatic steps, though the intermediate 4-hydroxybutyrate. First, 4-hydroxybutyryl-CoA can be converted to 4-hydroxybutyrate by a CoA transferase, hydrolase or synthetase. Alternately, 4-hydroxybutyryl-CoA can be converted to 4-hydroxybutyrate via a phosphonated intermediate by enzymes with phosphotrans-4-hydroxybutyrylase and 4-hydroxybutyrate kinase. Exemplary candidates for these enzymes are described above.

Subsequent conversion of 4-hydroxybutyrate to 4-hydroxybutanal is catalyzed by an aryl-aldehyde dehydrogenase, or equivalently a carboxylic acid reductase. Such an enzyme is found in *Nocardia iowensis*. Carboxylic acid reductase catalyzes the magnesium, ATP and NADPH-dependent reduction of carboxylic acids to their corresponding aldehydes (Venkitasubramanian et al., *J. Biol. Chem.* 282:478-485 (2007)) and is capable of catalyzing the conversion of 4-hydroxybutyrate to 4-hydroxybutanal. This enzyme, encoded by car, was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industires*, ed. R. N. Patel, Chapter 15, pp. 425-440, CRC Press LLC, Boca Raton, Fla. (2006)).

| Gene name | GI No. | GenBank Accession No. | Organism |
| --- | --- | --- | --- |
| Car | 40796035 | AAR91681.1 | *Nocardia iowensis* (sp. NRRL 5646) |
| Npt | 114848891 | ABI83656.1 | *Nocardia iowensis* (sp. NRRL 5646) |

Additional car and npt genes can be identified based on sequence homology.

| Gene name | GI No. | GenBank Accession No. | Organism |
| --- | --- | --- | --- |
| fadD9 | 121638475 | YP_978699.1 | *Mycobacterium bovis* BCG |
| BCG_2812c | 121638674 | YP_978898.1 | *Mycobacterium bovis* BCG |
| nfa20150 | 54023983 | YP_118225.1 | *Nocardia farcinica* IFM 10152 |
| nfa40540 | 54026024 | YP_120266.1 | *Nocardia farcinica* IFM 10152 |
| SGR_6790 | 182440583 | YP_001828302.1 | *Streptomyces griseus* subsp. *griseus* NBRC 13350 |
| SGR_665 | 182434458 | YP_001822177.1 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | ZP_04026660.1 | *Tsukamurella paurometabola* DSM 20162 |

-continued

| Gene name | GI No. | GenBank Accession No. | Organism |
|---|---|---|---|
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6): 380-387 (2007)). Co-expression of griC and griD with SGR_665, an enzyme similar in sequence to the *Nocardia iowensis* npt, can be beneficial.

| Gene name | GI No. | GENBANK Accession No. | Organism |
|---|---|---|---|
| griC | 182438036 | YP_001825755.1 | *Streptomyces griseus* subsp. *griseus* NBRC 13350 |
| Grid | 182438037 | YP_001825756.1 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

| Gene name | GI No. | GENBANK Accession No. | Organism |
|---|---|---|---|
| LYS2 | 171867 | AAA34747.1 | *Saccharomyces cerevisiae* |
| LYS5 | 1708896 | P50113.1 | *Saccharomyces cerevisiae* |
| LYS2 | 2853226 | AAC02241.1 | *Candida albicans* |
| LYS5 | 28136195 | AAO26020.1 | *Candida albicans* |
| Lys1p | 13124791 | P40976.3 | *Schizosaccharomyces pombe* |
| Lys7p | 1723561 | Q10474.1 | *Schizosaccharomyces pombe* |
| Lys2 | 3282044 | CAA74300.1 | *Penicillium chrysogenum* |

Enzymes exhibiting 1,4-butanediol dehydrogenase activity are capable of forming 1,4-butanediol from 4-hydroxybutanal. Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.* 66:5231-5235 (2000)), ADH2 from *Saccharomyces cerevisiae* Atsumi et al. *Nature* 451:86-89 (2008)), yahD from *E. coli* which has preference for molecules longer than C(3) (Sulzenbacher et al., *J. Mol. Biol.* 342:489-502 (2004)), and bdh I and bdh II from *C. acetobutylicum* which converts butyryaldehyde into butanol (Walter et al., *J. Bacteriol.* 174:7149-7158 (1992)). ADH1 from *Zymomonas mobilis* has been demonstrated to have activity on a number of aldehydes including formaldehyde, acetaldehyde, propionaldehyde, butyraldehyde, and acrolein (Kinoshita, *Appl. Microbiol. Biotechnol.* 22:249-254 (1985)).

TABLE 36

| Protein | GenBank ID | GI Number | Organism |
|---|---|---|---|
| alrA | BAB12273.1 | 9967138 | *Acinetobacter* sp. Strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Enzymes exhibiting 4-hydroxybutyrate dehydrogenase activity (EC 1.1.1.61) also fall into this category. Such enzymes have been characterized in *Ralstonia eutropha* (Bravo et al., *J. Forensic Sci.* 49:379-387 (2004)), *Clostridium kluyveri* (Wolff and Kenealy, *Protein Expr. Purif.* 6:206-212 (1995)) and *Arabidopsis thaliana* (Breitkreuz et al., *J. Biol. Chem.* 278:41552-41556 (2003)).

TABLE 37

| Protein | GenBank ID | GI Number | Organism |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |

The first step in the cloning and expression process is to express in *E. coli* the minimal set of genes (e.g., MtaA, MtaB, and MtaC) necessary to produce Me-THF from methanol. These methyltransferase activities use Coenzyme $B_{12}$ (cobalamin) as a cofactor. In *Morella thermoacetica*, a cascade of methyltransferase proteins mediate incorporation of methanol derived methyl groups into the acetyl-CoA synthase pathway. Recent work (Das et al., *Proteins* 67:167-176 (2007)) indicates that MtaABC are encoded by Moth_1208-09 and Moth_2346. These genes are cloned via proof-reading PCR and linked together for expression in a high-copy number vector such as pZE22-S under control of the repressible PA1-lacO1 promoter (Lutz and Bujard, *Nucleic Acids Res.* 25:1203-1210 (1997)). Cloned genes are verified by PCR and or restriction enzyme mapping to demonstrate construction and insertion of the 3-gene set into the expression vector. DNA sequencing of the presumptive clones is carried out to confirm the expected sequences of each gene. Once confirmed, the final construct is expressed in *E. coli* K-12 (MG1655) cells by addition of IPTG inducer between 0.05 and 1 mM final concentration. Expression of the cloned genes is monitored using SDS-PAGE of whole cell extracts. To optimize levels of soluble vs. pellet (potentially inclusion body origin) protein, the affect of titration of the promoter on these levels can be examined. If no acceptable expression is obtained, higher or lower copy number vectors or variants in promoter strength are tested.

To determine if expression of the MtaABC proteins from *M. thermoacetica* confers upon *E. coli* the ability to transfer methyl groups from methanol to tetrahydrofolate (THF) the recombinant strain is fed methanol at various concentrations. Activity of the methyltransferase system is assayed anaerobically as described for vanillate as a methyl source in *M. thermoacetica* (Naidu and Ragsdale, *J. Bacteriol.* 183:3276-3281 (2001)) or for *Methanosarcina barkeri* methanol methyltransferase (Sauer et al., *Eur. J. Biochem.* 243:670-677 (1997); Tallant and Krzycki, *J. Bacteriol.* 178:1295-1301 (1996); Tallant and Krzycki, *J. Bacteriol.* 179:6902-6911 (1997); Tallant et al., *J. Biol. Chem.* 276:4485-4493 (2001)). For a positive control, *M. thermoacetica* cells are cultured in parallel and assayed anaerobically to confirm endogenous methyltransferase activity. Demonstration of dependence on exogenously added coenzyme $B_{12}$ confirms methanol: corrinoid methyltransferase activity in *E. coli*.

Once methyltransferase expression is achieved, further work is performed towards optimizing the expression. Titrating the promoter in the expression vector enables the testing of a range of expression levels. This is then used as a guide towards the expression required in single-copy, or enables the determination of whether or not a single-copy of these genes allows sufficient expression. If so, the methyltransferase genes are integrated into the chromosome as a single, synthetic operon. This entails targeted integration using RecET-based 'recombineering' (Angrand et al., *Nucleic Acids Res.* 27:e16 (1999); Muyrers et al. *Nucleic Acids Res.* 27:1555-1557 (1999); Zhang et al., 1998 *Nat. Genet.* 20:123-128 (1998)). A potential issue with RecET-based integration of a cassette and removal of a FRT or loxP-bounded selectable marker by FLP or Cre is the production of a recombination scar at each integration site. While problems caused by this can be minimized by a number of methods, other means that do not leave genomic scars are available. The standard alternative, is to introduce the desired genes using integrative 'suicide' plasmids coupled to counter-selection such as that allowed by the *Bacillus* sacB gene (Link et al., *J. Bacteriol.* 179:6228-6237 (1997)); in this way, markerless and scar less insertions at any location in the *E. coli* chromosome can be generated. The final goal is a strain of *E. coli* K-12 expressing methanol:corrinoid methyltransferase activity under an inducible promoter and in single copy (chromosomally integrated).

Using standard PCR methods, entire ACS/CODH operons are assembled into low or medium copy number vectors such as pZA33-S(P15A-based) or pZS13-S (pSC101-based). As described for the methyltransferase genes, the structure and sequence of the cloned genes are confirmed. Expression is monitored via protein gel electrophoresis of whole-cell lysates grown under strictly anaerobic conditions with the requisite metals (Ni, Zn, Fe) and coenzyme $B_{12}$ provided. As necessary, the gene cluster is modified for *E. coli* expression by identification and removal of any apparent terminators and introduction of consensus ribosomal binding sites chosen from sites known to be effective in *E. coli* (Barrick et al., *Nucleic Acids Res.* 22:1287-1295 (1994); Ringquist et al., *Mol. Microbiol.* 6:1219-1229 (1992)). However, each gene cluster is cloned and expressed in a manner parallel to its native structure and expression. This helps ensure the desired stoichiometry between the various gene products—most of which interact with each other. Once satisfactory expression of the CODH/ACS gene cluster under anaerobic conditions is achieved, the ability of cells expressing these genes to fix CO and/or $CO_2$ into cellular carbon is assayed. Initial conditions employ strictly anaerobically grown cells provided with exogenous glucose as a carbon and energy source via substrate-level phosphorylation or anaerobic respiration with nitrate as an electron acceptor. Additionally, exogenously provided $CH_3$-THF is added to the medium.

The ACS/CODH genes are cloned and expressed in cells also expressing the methanol-methyltransferase system. This is achieved by introduction of compatible plasmids expressing ACS/CODH into MTR-expressing cells. For added long-term stability, the ACS/CODH and MTR genes can also be integrated into the chromosome. After strains of *E. coli* capable of utilizing methanol to produce Me-THF and of expressing active CODH/ACS gene are made, they are assayed for the ability to utilize both methanol and syngas for incorporation into acetyl-CoA, acetate, and cell mass. Initial conditions employ strictly anaerobically grown cells provided with exogenous glucose as a carbon and energy source. Alternatively, or in addition to glucose, nitrate will be added to the fermentation broth to serve as an electron acceptor and initiator of growth. Anaerobic growth of *E. coli* on fatty acids, which are ultimately metabolized to acetyl-CoA, has been demonstrated in the presence of nitrate (Campbell et al., *Mol. Microbiol.* 47:793-805 (2003)). Oxygen can also be provided as long as its intracellular levels are maintained below any inhibition threshold of the engineered enzymes. 'Synthetic syngas' of a composition suitable for these experiments is employed along with methanol. $^{13}$C-labeled methanol or $^{13}$C-labeled CO are provided to the cells and analytical mass spectrometry is employed to measure incorporation of the labeled carbon into acetate and cell mass (e.g., proteinogenic amino acids).

The pyruvate ferredoxin oxidoreductase genes from *M. thermoacetica*, *D. africanus*, and *E. coli* are cloned and expressed in strains exhibiting MTR and ACS/CODH activities. Conditions, promoters, etc., are described above. Given the large size of the PFOR genes and oxygen sensitivity of the corresponding enzymes, tests will be performed using low or single-copy plasmid vectors or single-copy chromosomal integrations. Activity assays described in ref. (Furdui and Ragsdale, *J. Biol. Chem.* 275:28494-28499 (2000)) will be applied to demonstrate activity. In addition, demonstration of growth on the gaseous carbon sources and methanol in the absence of an external electron acceptor will provide further evidence for PFOR activity in vivo.

The endogenous hydrogen-utilizing hydrogenase activity of the host organism is tested by growing the cells as described above in the presence and absence of hydrogen. If a dramatic shift towards the formation of more reduced products during fermentation is observed (e.g., increased ethanol as opposed to acetate), this indicates that endogenous hydrogenase activity is sufficiently active. In this case, no heterologous hydrogenases are cloned and expressed. If the native enzymes do not have sufficient activity or reduce the needed acceptor, the genes encoding an individual hydrogenase complex are cloned and expressed in strains exhibiting MTR, ACS/CODH, and PFOR activities. Conditions, promoters, etc., are described above.

The normative genes needed for isopropanol synthesis are cloned on expression plasmids as described previously. The host strain also expresses methanol methyltransferase activity, CODH/ACS activity, and possibly PFOR and hydrogenase activities. At this point, these (CODH/ACS, etc.) genes are integrated into the genome and expressed from promoters that can be used constitutively or with inducers (i.e., PA1-lacO1 is inducible in cells containing lacI or is otherwise constitutive). Once expression and yields of isopropanol are optimized, the base strain is further modified by integration of a single copy of these genes at a neutral locus. Given the relatively limited number of genes (at minimum, 3, and at most, 6), Applicants construct an artificial operon encoding the required genes. This operon is introduced using integrative plasmids and is coupled to counter-selection methods such as that allowed by the *Bacillus* sacB gene (Link et al., *J. Bacteriol.* 179:6228-6237 (1997)). In this way, markerless and scar less insertions at any location in the *E. coli* chromosome can be generated. Optimization involves altering gene order as well as ribosomal binding sites and promoters.

To over express any native genes, for example, the native atoB (b2224) gene of *E. coli* which can serve as an alternative to the *C. acetobutylicum* acetyl-coenzyme A [CoA]acetyl-transferase required for isopropanol production, RecET-based methods are applied to integrate a stronger upstream promoter. In the case of atoB, this gene is the last in an operon and the next gene downstream (yfaP) is both non-essential and in the opposite orientation. Therefore, polarity should not be an issue. A cassette containing a selectable marker such as spectinomycin resistance or chloramphenicol resistance flanked by FRT or loxP sites is used to select for introduction of a strong constitutive promoter (e.g., pL). Once the correct clone is obtained and validated, using qRT-PCR, FLP or Cre expression is used to select for removal of the FRT- or loxP-bounded marker.

The normative genes needed for 4-hydroxybutyrate synthesis are cloned on expression plasmids as described previously. The host strain also expresses methanol methyltransferase activity, CODH/ACS activity, and possibly PFOR and hydrogenase activities. At this point, these (CODH/ACS, etc.) genes are integrated into the genome and expressed from promoters that can be used constitutively or with inducers (i.e., PA1-lacO1 is inducible in cells containing lacI or is otherwise constitutive). Once expression and yields of 4-hydroxybutyrate are optimized, the base strain is further modified by integration of a single copy of these genes at a neutral locus. Given the relatively limited number of genes (at minimum, 5, and at most, 6), an artificial operon encoding the required genes can be constructed. This operon is introduced using integrative plasmids and is coupled to counter-selection methods such as that allowed by the *Bacillus* sacB gene (Link et al., *J. Bacteriol.* 179:6228-6237 (1997)). In this way, markerless and scar less insertions at any location in the *E. coli* chromosome can be generated. Optimization involves altering gene order as well as ribosomal binding sites and promoters.

The normative genes needed for 1,4-butanediol synthesis are cloned on expression plasmids as described previously. The host strain also expresses methanol methyltransferase activity, CODH/ACS activity, and possibly PFOR and hydrogenase activities. At this point, these (CODH/ACS, etc.) genes are integrated into the genome and expressed from promoters that can be used constitutively or with inducers (i.e., PA1-lacO1 is inducible in cells containing lacI or is otherwise constitutive). Once expression and yields of 1,4-butanediol are optimized, the base strain is further modified by integration of a single copy of these genes at a neutral locus. Given the relatively limited number of genes (at minimum, 5, and at most, 6), an artificial operon encoding the required genes can be constructed. This operon is introduced using integrative plasmids and is coupled to counter-selection methods such as that allowed by the *Bacillus* sacB gene (Link et al., *J. Bacteriol.* 179:6228-6237 (1997)). In this way, markerless and scar less insertions at any location in the *E. coli* chromosome can be generated. Optimization involves altering gene order as well as ribosomal binding sites and promoters.

Engineering the capability to convert synthesis gas into acetyl-CoA, the central metabolite from which all cell mass components and many valuable products can be derived, into a foreign host such as *E. coli* can be accomplished following the expression of exogenous genes that encode various proteins of the Wood-Ljungdahl pathway. This pathway is highly active in acetogenic organisms such as *Moorella thermoacetica* (formerly, *Clostridium thermoaceticum*), which has been the model organism for elucidating the Wood-Ljungdahl pathway since its isolation in 1942 (Fontaine et al., *J. Bacteriol.* 43:701-715 (1942)). The Wood-Ljungdahl pathway comprises of two branches: the Eastern (or methyl) branch that enables the conversion of $CO_2$ to methyltetrahydrofolate (Me-THF) and the Western (or carbonyl) branch that enables the conversion of methyl-THF, CO, and Coenzyme-A into acetyl-CoA (FIG. 3). In some embodiments, the present invention provides a non-naturally occurring microorganism expressing genes encoding enzymes that catalyze the methyl and carbonyl branches of the Wood-Ljungdahl pathway. Such an organism is capable of converting CO, $CO_2$, and/or $H_2$ into acetyl-CoA, cell mass, and products.

Figure 3A:
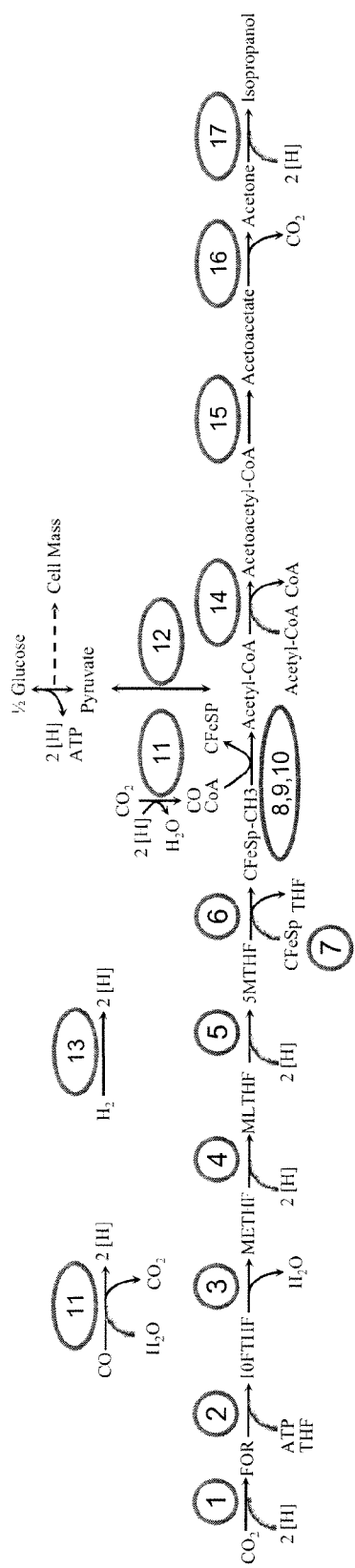
FIG. 3A shows a synthetic metabolic pathway for the conversion of carbohydrates and/or gases including CO, $CO_2$, and/or $H_2$ to acetyl-CoA, and further to isopropanol.
Figure 3B:
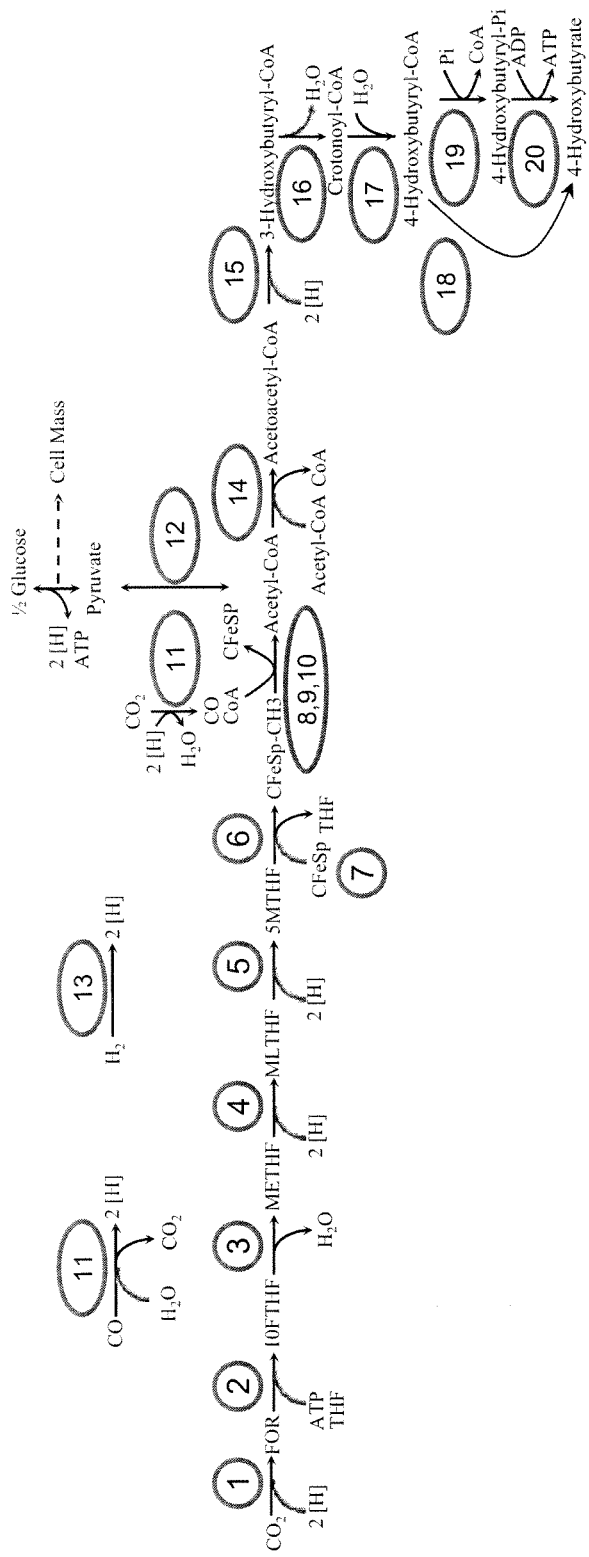
FIG. 3B shows a synthetic metabolic pathway for the conversion of carbohydrates and/or gases including CO, $CO_2$, and/or $H_2$ to acetyl-CoA, and further to 4-hydroxybutyrate.
Figure 3C:
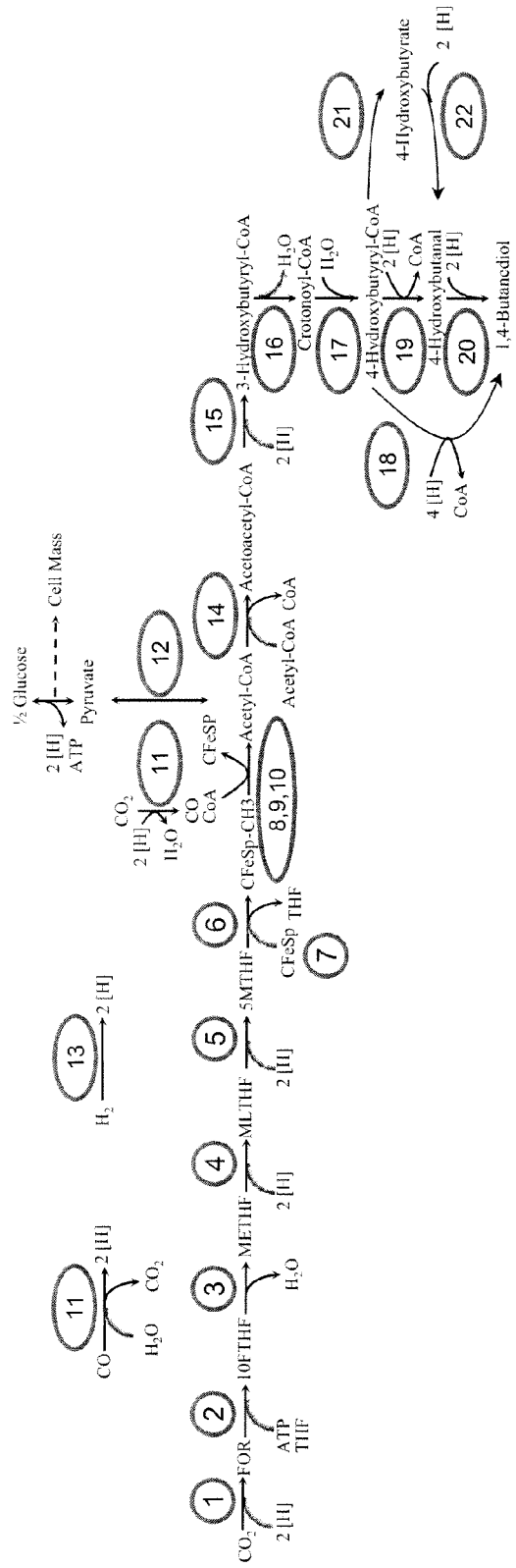
FIG. 3C shows a synthetic metabolic pathway for the conversion of carbohydrates and/or gases including CO, $CO_2$, and/or $H_2$ to acetyl-CoA, and further to 1,4-butanediol.

Another organism of the present invention contains three capabilities which are depicted in FIG. 3A: 1) a functional methyl branch of the Wood-Ljungdahl pathway which enables the conversion of THF and $CO_2$ to 5-methyl-tetrahydrofolate, 2) the ability to combine CO, Coenzyme A, and the methyl group of Me-THF to form acetyl-CoA, and 3) the ability to synthesize isopropanol from acetyl-CoA. The fifth organism described in this invention, depicted in FIG. 3B, contains a functional methyl branch of the Wood-Ljungdahl pathway, the ability to synthesize acetyl-CoA, and the ability to synthesize 4-hydroxybutyrate from acetyl-CoA. The sixth organism described in this invention, depicted in FIG. 3C, contains a functional methyl branch of the Wood-Ljungdahl pathway, the ability to synthesize acetyl-CoA, and the ability to synthesize 1,4-butanediol from acetyl-CoA.

These three organisms are able to 'fix' carbon from exogenous CO and/or $CO_2$ to synthesize acetyl-CoA, cell mass, and products. A host organism engineered with these capabilities that also naturally possesses the capability for anapleurosis (e.g., *E. coli*) can grow on the syngas-generated acetyl-CoA in the presence of a suitable external electron acceptor such as nitrate. This electron acceptor is required to accept electrons from the reduced quinone formed via succinate dehydrogenase. A further advantage of adding an external electron acceptor is that additional energy for cell growth, maintenance, and product formation can be generated from respiration of acetyl-CoA. An alternative strategy involves engineering a pyruvate ferredoxin oxidoreductase (PFOR) enzyme into the strain to enable synthesis of biomass precursors in the absence of an external electron acceptor. A further characteristic of the engineered organism is the capability for extracting reducing equivalents from molecular hydrogen. This enables a high yield of reduced products such as ethanol, butanol, isobutanol, isopropanol, 1,4-butanediol, succinic acid, fumaric acid, malic acid, 4-hydroxybutyric acid, 3-hydroxypropionic acid, lactic acid, adipic acid, 6-aminocaproic acid, hexamethylenediamine, 2-hydroxyisobutyric acid, 3-hydroxyisobutyric acid, methacrylic acid, and acrylic acid.

The organisms provided herein can produce acetyl-CoA, cell mass, and targeted chemicals, more specifically isopropanol, 4-hydroxybutyrate, and 1,4-butanediol, from: 1) CO, 2) $CO_2$ and $H_2$, 3) CO, $CO_2$, and $H_2$, 4) synthesis gas comprising CO and $H_2$, 5) synthesis gas comprising CO, $CO_2$, and $H_2$, 6) one or more carbohydrates, 7) methanol and one or more carbohyrates, and 8) methanol. Exemplary carbohydrates include but are not limited to glucose, sucrose, xylose, arabinose and glycerol.

Successfully engineering any of these pathways into an organism involves identifying an appropriate set of enzymes, cloning their corresponding genes into a production host, optimizing the stability and expression of these genes, optimizing fermentation conditions, and assaying for product formation following fermentation. Below are described enzymes that catalyze steps 1 through 5 of the pathways depicted in FIGS. 3A through 3C. These enzymes are required to enable the conversion of synthesis gas to acetyl-CoA. Enzymes for steps 6 through 17 in FIG. 3A and steps 6 through 20 in FIGS. 3B and 3C were described above. To engineer a production host for the utilization of syngas, one or more exogenous DNA sequence(s) encoding the requisite enzymes can be expressed in the microorganism.

Formate dehydrogenase is a two subunit selenocysteine-containing protein that catalyzes the incorporation of $CO_2$ into formate in *Moorella thermoacetica* (Andreesen and Ljungdahl, *J. Bacteriol.* 116:867-873 (1973); Li et al., *J. Bacteriol.* 92:405-412 (1966); Yamamoto et al., *J. Biol. Chem.* 258:1826-1832 (1983). The loci, Moth_2312 is responsible for encoding the alpha subunit of formate dehydrogenase while the beta subunit is encoded by Moth 2314 (Pierce et al., *Environ. Microbiol.* (2008)). Another set of genes encoding formate dehydrogenase activity with a propensity for $CO_2$ reduction is encoded by Sfum_2703 through Sfum_2706 in *Syntrophobacter fumaroxidans* (de Bok et al., *Eur. J. Biochem.* 270:2476-2485 (2003)); Reda et al., *Proc. Natl. Acad. Sci. U.S.A.* 105:10654-10658 (2008)). A similar set of genes presumed to carry out the same function are encoded by CHY_0731, CHY_0732, and CHY_0733 in *C. hydrogenoformans* (Wu et al., *PLoS Genet.* 1:e65 (2005)). Homologs are also found in *C. carboxidivorans* P7.

TABLE 38

| Protein | GenBank ID | GI Number | Organism |
|---|---|---|---|
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Srum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |

Formyltetrahydrofolate synthetase ligates formate to tetrahydrofolate at the expense of one ATP. This reaction is catalyzed by the gene product of Moth 0109 in *M. thermoacetica* (Lovell et al., *Arch. Microbiol.* 149:280-285 (1988); Lovell et al., *Biochemistry* 29:5687-5694 (1990); O'brien et al., *Experientia. Suppl.* 26:249-262 (1976), FHS in *Clostridium acidurici* (Whitehead and Rabinowitz, *J. Bacteriol.* 167:205-209 (1986); Whitehead and Rabinowitz, *J. Bacteriol.* 170: 3255-3261 (1988)), and CHY 2385 in *C. hydrogenoformans* (Wu et al., *PLoS Genet.* 1:e65 (2005)). Homologs exist in *C. carboxidivorans* P7.

TABLE 39

| Protein | GenBank ID | GI Number | Organism |
|---|---|---|---|
| Moth_0109 | YP_428991.1 | 83588982 | *Moorella thermoacetica* |
| CHY_2385 | YP_361182.1 | 78045024 | *Carboxydothermus hydrogenoformans* |
| FHS | P13419.1 | 120562 | *Clostridium acidurici* |
| CcarbDRAFT_1913 | ZP_05391913.1 | 255524966 | *Clostridium carboxidivorans* P7 |
| CcarbDRAFT_2946 | ZP_05392946.1 | 255526022 | *Clostridium carboxidivorans* P7 |

In *M. thermoacetica*, *E. coli*, and *C. hydrogenoformans*, methenyltetrahydrofolate cyclohydrolase and methylenetetrahydrofolate dehydrogenase are carried out by the bi-functional gene products of Moth_1516, folD and CHY_1878, respectively (D'Ari and Rabinowitz, *J. Biol. Chem.* 266: 23953-23958 (1991); Pierce et al., *Environ. Microbiol.* (2008); Wu et al., *PLoS Genet.* 1:e65 (2005)). A homolog exists in *C. carboxidivorans* P7.

TABLE 40

| Protein | GenBank ID | GI Number | Organism |
|---|---|---|---|
| Moth_1516 | YP_430368.1 | 83590359 | *Moorella thermoacetica* |
| folD | NP_415062.1 | 16128513 | *Escherichia coli* |
| CHY_1878 | YP_360698.1 | 78044829 | *Carboxydothermus hydrogenoformans* |
| CcarbDRAFT_2948 | ZP_05392948.1 | 255526024 | *Clostridium carboxidivorans* P7 |

The final step of the methyl branch of the Wood-Ljungdahl pathway is catalyzed by methylenetetrahydrofolate reductase. In *M. thermoacetica*, this enzyme is oxygen-sensitive and contains an iron-sulfur cluster (Clark and Ljungdahl, *J. Biol. Chem.* 259:10845-10849 (1984)). This enzyme is encoded by metF in *E. coli* (Sheppard et al., *J. Bacteriol.* 181:718-725 (1999)) and CHY_1233 in *C. hydrogenoformans* (Wu et al., *PLoS Genet.* 1:e65 (2005)). The *M. thermoacetica* genes, and its *C. hydrogenoformans* counterpart, are located near the CODH/ACS gene cluster, separated by putative hydrogenase and heterodisulfide reductase genes.

TABLE 41

| Protein | GenBank ID | GI Number | Organism |
|---|---|---|---|
| metF | NP_418376.1 | 16131779 | *Escherichia coli* |
| CHY_1233 | YP_360071.1 | 78044792 | *Carboxydothermus hydrogenoformans* |

While *E. coli* naturally possesses the capability for some of the required transformations (i.e., methenyltetrahydrofolate cyclohydrolase, methylenetetrahydrofolate dehydrogenase, methylenetetrahydrofolate reductase), it is thought that the methyl branch enzymes from acetogens may have significantly higher (50-100×) specific activities than those from non-acetogens (Morton et al., *Genetics and molecular biology of anaerobic bacteria*, p. 389-406, Springer Verlag, New York (1992.)). The formate dehydrogenase also appears to be specialized for anaerobic conditions (Ljungdahl and Andreesen, *FEBS Lett.* 54:279-282 (1975)). Therefore, various non-native versions of each of these are expressed in the strain of *E. coli* capable of methanol and syngas utilization. Specifically, these genes are cloned and combined into an expression vector designed to express them as a set. Initially, a high or medium copy number vector is chosen (using ColE1 or P15A replicons). One promoter that can be used is a strongly constitutive promoter such as lambda pL or an IPTG-inducible version of this, pL-lacO (Lutz and Bujard, *Nucleic Acids Res.* 25:1203-1210 (1997)). To make an artificial operon, one 5' terminal promoter is placed upstream of the set of genes and each gene receives a consensus rbs element. The order of genes is based on the natural order whenever possible. Ultimately, the genes are integrated into the *E. coli* chromosome. Enzyme assays are performed as described in (Clark and Ljungdahl, *J. Biol. Chem.* 259:10845-10849 (1984); Clark and Ljungdahl, *Meth. Enzymol.* 122:392-399 (1986); D'Ari and Rabinowitz, *J. Biol. Chem.* 266:23953-23958 (1991); de Mata and Rabinowitz, *J. Biol. Chem.* 255:2569-2577 (1980); Ljungdahl and Andreesen, *Meth. Enzymol.* 53:360-372 (1978); Lovell et al., 1988 *Arch. Microbiol* 149:280-285 (1988); Yamamoto et al., *J. Biol. Chem.* 258:1826-1832 (1983)).

After strains of *E. coli* expressing both the carbonyl and methyl branches of the Wood-Ljungdahl pathway are constructed, they are assayed for the ability to utilize syngas consisting of CO, $CO_2$, and/or $H_2$, for incorporation into acetyl-CoA, cell mass, and isopropanol or 1,4-butanediol.

Initial conditions employ strictly anaerobically grown cells provided with exogenous glucose as a carbon and energy source. Metabolizing glucose or other carbohydrates to acetyl-CoA provides one potential source of $CO_2$ that can be fixed via the Wood-Ljungdahl pathway. Alternatively, or in addition to glucose, nitrate will be added to the fermentation broth to serve as an electron acceptor and initiator of growth. Anaerobic growth of *E. coli* on fatty acids, which are ultimately metabolized to acetyl-CoA, has been demonstrated in the presence of nitrate (Campbell et al., *Mol. Microbiol.* 47:793-805 (2003)). Oxygen can also be provided as long as its intracellular levels are maintained below any inhibition threshold of the engineered enzymes. 'Synthetic syngas' of a composition suitable for these experiments can also be employed. $^{13}$C-labeled CO and/or $CO_2$ are provided to the cells and analytical mass spectrometry is employed to measure incorporation of the labeled carbon into acetate, isopropanol, 4-hydroxybutyrate, 1,4-butanediol, and cell mass (e.g., proteinogenic amino acids).

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more isopropanol, 4-hydroxybutyrate, or 1,4-butanediol biosynthetic pathways. Depending on the host microbial organism chosen for biosynthesis, nucleic acids for some or all of a particular isopropanol, 4-hydroxybutyrate, or 1,4-butanediol biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve isopropanol, 4-hydroxybutyrate, or 1,4-butanediol biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as isopropanol, 4-hydroxybutyrate, or 1,4-butanediol.

Depending on the isopropanol, 4-hydroxybutyrate, or 1,4-butanediol biosynthetic pathway constituents of a selected host microbial organism, the non-naturally occurring microbial organisms of the invention will include at least one exogenously expressed isopropanol, 4-hydroxybutyrate, or 1,4-butanediol pathway-encoding nucleic acid and up to all encoding nucleic acids for one or more isopropanol, 4-hydroxybutyrate, or 1,4-butanediol biosynthetic pathways. For example, isopropanol, 4-hydroxybutyrate, or 1,4-butanediol biosynthesis can be established in a host deficient in a pathway enzyme or protein through exogenous expression of the corresponding encoding nucleic acid. In a host deficient in all enzymes or proteins of an isopropanol, 4-hydroxybutyrate, or 1,4-butanediol pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of isopropanol, 4-hydroxybutyrate, or 1,4-butanediol can be included.

Given the teachings and guidance provided herein, those skilled in the art will understand that the number of encoding nucleic acids to introduce in an expressible form will, at least, parallel the isopropanol, 4-hydroxybutyrate, or 1,4-butanediol pathway deficiencies of the selected host microbial organism. Therefore, a non-naturally occurring microbial organism of the invention can have one, two, three, four, five, six, seven, eight, nine, ten, eleven, twelve, thirteen, fourteen, fifteen, sixteen, up to all nucleic acids encoding the enzymes or proteins constituting an isopropanol, 4-hydroxybutyrate, or 1,4-butanediol biosynthetic pathway disclosed herein. In some embodiments, the non-naturally occurring microbial organisms also can include other genetic modifications that facilitate or optimize isopropanol, 4-hydroxybutyrate, or 1,4-butanediol biosynthesis or that confer other useful functions onto the host microbial organism. One such other functionality can include, for example, augmentation of the synthesis of one or more of the isopropanol, 4-hydroxybutyrate, or 1,4-butanediol pathway precursors such as acetyl-CoA.

Generally, a host microbial organism is selected such that it produces the precursor of an isopropanol, 4-hydroxybutyrate, or 1,4-butanediol pathway, either as a naturally produced molecule or as an engineered product that either provides de novo production of a desired precursor or increased production of a precursor naturally produced by the host microbial organism. For example, acetyl-CoA is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of an isopropanol, 4-hydroxybutyrate, or 1,4-butanediol pathway.

In some embodiments, a non-naturally occurring microbial organism of the invention is generated from a host that contains the enzymatic capability to synthesize isopropanol, 4-hydroxybutyrate, or 1,4-butanediol. In this specific embodiment it can be useful to increase the synthesis or accumulation of an isopropanol, 4-hydroxybutyrate, or 1,4-butanediol pathway product to, for example, drive isopropanol, 4-hydroxybutyrate, or 1,4-butanediol pathway reactions toward isopropanol, 4-hydroxybutyrate, or 1,4-butanediol production. Increased synthesis or accumulation can be accomplished by, for example, overexpression of nucleic acids encoding one or more of the above-described isopropanol, 4-hydroxybutyrate, or 1,4-butanediol pathway enzymes or proteins. Over expression the enzyme or enzymes and/or protein or proteins of the isopropanol, 4-hydroxybutyrate, or 1,4-butanediol pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing isopropanol, 4-hydroxybutyrate, or 1,4-butanediol, through overexpression of one, two, three, four, five, six, seven, eight, nine, ten, eleven, twelve, thirteen, fourteen, fifteen, sixteen, that is, up to all nucleic acids encoding isopropanol, 4-hydroxybutyrate, or 1,4-butanediol biosynthetic pathway enzymes or proteins. In addition, a non-naturally occurring organism can be generated by mutagenesis of an endogenous gene that results in an increase in activity of an enzyme in the isopropanol, 4-hydroxybutyrate, or 1,4-butanediol biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, an isopropanol, 4-hydroxybutyrate, or 1,4-butanediol biosynthetic pathway onto the microbial organism. Alternatively, encoding nucleic acids can be introduced to produce an intermediate microbial organism having the biosynthetic capability to catalyze some of the required reactions to confer isopropanol, 4-hydroxybutyrate, or 1,4-butanediol biosynthetic capability. For example, a non-naturally occurring microbial organism having an isopropanol, 4-hydroxybutyrate, or 1,4-butanediol biosynthetic pathway can comprise at least two exogenous nucleic acids encoding desired enzymes or proteins. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention and so forth, as desired, so long as the combination of enzymes and/or proteins of the desired biosynthetic pathway results in production of the corresponding desired product. Similarly, any combination of four, or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of isopropanol, 4-hydroxybutyrate, or 1,4-butanediol as described herein, the non-naturally occurring microbial organisms and methods of the invention also can be utilized in various combinations with each other and with other microbial organisms and methods well known in the art to achieve product biosynthesis by other routes. For example, one alternative to produce isopropanol, 4-hydroxybutyrate, or 1,4-butanediol other than use of the isopropanol, 4-hydroxybutyrate, or 1,4-butanediol producers is through addition of another microbial organism capable of converting an isopropanol, 4-hydroxybutyrate, or 1,4-butanediol pathway intermediate to isopropanol, 4-hydroxybutyrate, or 1,4-butanediol. One such procedure includes, for example, the fermentation of a microbial organism that produces an isopropanol, 4-hydroxybutyrate, or 1,4-butanediol pathway intermediate. The isopropanol, 4-hydroxybutyrate, or 1,4-butanediol pathway intermediate can then be used as a substrate for a second microbial organism that converts the isopropanol, 4-hydroxybutyrate, or 1,4-butanediol pathway intermediate to isopropanol, 4-hydroxybutyrate, or 1,4-butanediol. The isopropanol, 4-hydroxybutyrate, or 1,4-butanediol pathway intermediate can be added directly to another culture of the second organism or the original culture of the isopropanol, 4-hydroxybutyrate, or 1,4-butanediol pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, isopropanol, 4-hydroxybutyrate, or 1,4-butanediol. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of isopropanol, 4-hydroxybutyrate, or 1,4-butanediol can be accomplished by constructing a microbial organism that contains biosynthetic pathways for conversion of one pathway intermediate to another pathway intermediate or the product. Alternatively, isopropanol, 4-hydroxybutyrate, or 1,4-butanediol also can be biosynthetically produced from microbial organisms through co-culture or co-fermentation using two organisms in the same vessel, where the first microbial organism produces an isopropanol, 4-hydroxybutyrate, or 1,4-butanediol intermediate and the second microbial organism converts the intermediate to isopropanol, 4-hydroxybutyrate, or 1,4-butanediol.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce isopropanol, 4-hydroxybutyrate, or 1,4-butanediol.

Sources of encoding nucleic acids for an isopropanol, 4-hydroxybutyrate, or 1,4-butanediol pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite isopropanol, 4-hydroxybutyrate, or 1,4-butanediol biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of isopropanol, 4-hydroxybutyrate, or 1,4-butanediol described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative isopropanol, 4-hydroxybutyrate, or 1,4-butanediol biosynthetic pathway exists in an unrelated species, isopropanol, 4-hydroxybutyrate, or 1,4-butanediol biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize isopropanol, 4-hydroxybutyrate, or 1,4-butanediol.

Host microbial organisms can be selected from, and the non-naturally occurring microbial organisms generated in, for example, bacteria, yeast, fungus, algae, cyanobacteria or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Glucono-* bacter oxydans, Zymomonas mobilis, Lactococcus lactis, Lactobacillus plantarum, Streptomyces coelicolor, Clostridium acetobutylicum, Pseudomonas fluorescens, and Pseudomonas putida. Exemplary yeasts or fungi include species selected from Saccharomyces cerevisiae, Schizosaccharomyces pombe, Kluyveromyces lactis, Kluyveromyces marxianus, Aspergillus terreus, Aspergillus niger and Pichia pastoris. Exemplary cyanobacteria include Acaryochloris marina MBIC11017, Anabaena sp. PCC 7120, Anabaena variabilis ATCC 29413, Agmenellum quadruplicatum, Chlorobium tepidum TLS, Cyanothece sp. ATCC 51142, Gloeobacter violaceus PCC 7421, Microcystis aeruginosa NIES-843, Nostoc punctiforme ATCC 29133, Prochlorococcus marinus MED4, Prochlorococcus marinus MIT9313, Prochlorococcus marinus SS120, Prochlorococcus marinus str. AS9601, Prochlorococcus marinus str. MIT 9211, Prochlorococcus marinus str. MIT 9215, Prochlorococcus marinus str. MIT 9301, Prochlorococcus marinus str. MIT 9303, Prochlorococcus marinus str. MIT 9312, Prochlorococcus marinus str. MIT 9515, Prochlorococcus marinus str. NATL1A, Prochlorococcus marinus str. NATL2A, Rhodopseudomonas palustris CGA009, Synechococcus elongatus PCC 6301, Synechococcus elongatus PCC 7942, Synechococcus sp. CC9311, Synechococcus sp. CC9605, Synechococcus sp. CC9902, Synechococcus sp. JA-2-3BVa (2-13), Synechococcus sp. JA-3-3Ab, Synechococcus sp. PCC 7002, Synechococcus sp. RCC307, Synechococcus sp. WH 7803, Synechococcus sp. WH8102, Synechocystis sp. PCC 6803, Thermosynechococcus elongatus BP-1, Trichodesmium erythraeum IMS101. Exemplary algae include Botryococcus braunii, Chlamydomonas reinhardii, Chlorella sp., Crypthecodinium cohnii, Cylindrotheca sp., Dunaliella primolecta, Isochrysis sp., Monallanthus salina, Nannochloris sp., Nannochloropsis sp., Neochloris oleoabundans, Nitzschia sp., Phaeodactylum tricornutum, Schizochytrium sp., and Tetraselmis sueica.

E. coli is a particularly useful host organism since it is a well characterized microbial organism suitable for genetic engineering. Other particularly useful host organisms include yeast such as Saccharomyces cerevisiae. It is understood that any suitable microbial host organism can be used to introduce metabolic and/or genetic modifications to produce a desired product.

Methods for constructing and testing the expression levels of a non-naturally occurring isopropanol, 4-hydroxybutyrate, or 1,4-butanediol-producing host can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of isopropanol, 4-hydroxybutyrate, or 1,4-butanediol can be introduced stably or transiently into a host cell using techniques well known in the art including, but not limited to, conjugation, electroporation, chemical transformation, transduction, transfection, and ultrasound transformation. For exogenous expression in E. coli or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in E. coli (Hoffmeister et al., J. Biol. Chem. 280:4329-4338 (2005)).

For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more isopropanol, 4-hydroxybutyrate, or 1,4-butanediol biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention provides a method for producing isopropanol that includes culturing a non-naturally occurring microbial organism having an isopropanol pathway. The pathway includes at least one exogenous nucleic acid encoding an isopropanol pathway enzyme expressed in a sufficient amount to produce isopropanol under conditions and for a sufficient period of time to produce isopropanol. The isopropanol pathway comprising an acetoacetyl-CoA thiolase, an acetoacetyl-CoA transferase, an acetoacetyl-CoA hydrolase, an acetoacetyl-CoA synthetase, a phosphotransacetoacetylase, an acetoacetate kinase, an acetoacetate decarboxylase, and an isopropanol dehydrogenase. An alternative isopropanol pathway comprises acetoacetyl-CoA thiolase, succinyl-CoA:3-ketoacid CoA transferase, acetoacetate decarboxylase, and an isopropanol dehydrogenase.

In embodiments where an organism has a methanol methyltransferase, culturing can be carried out utilizing a feedstock such as 1) methanol and CO, 2) methanol, $CO_2$, and $H_2$, 3) methanol, CO, $CO_2$, and $H_2$, 4) methanol and synthesis gas comprising CO and $H_2$, 5) methanol and synthesis gas comprising CO, $CO_2$, and $H_2$, 6) one or more carbohydrates, 7) methanol and one or more carbohydrates, and 8) methanol. Exemplary carbohydrates include but are not limited to glucose, sucrose, xylose, arabinose and glycerol.

In embodiments where an organism has a formate dehydrogenase, a formyltetrahydrofolate synthetase, a methenyltetrahydrofolate cyclohydrolase, a methylenetetrahydrofolate dehydrogenase, and a methylenetetrahydrofolate reductase, the organism can utilize a feedstock such as 1) CO, 2) $CO_2$ and $H_2$, 3) CO and $CO_2$, 4) synthesis gas comprising CO and $H_2$, 5) synthesis gas comprising CO, $CO_2$, and $H_2$, and 6) one or more carbohydrates.

Similarly, 4-hydroxybutyrate or 1,4-butanediol can also be produced by culturing the appropriate organisms as described herein above.

Suitable purification and/or assays to test for the production of isopropanol, 4-hydroxybutyrate, or 1,4-butanediol can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art (see, for example, WO/2008/115840 and Hanai et al., *Appl. Environ. Microbiol.* 73:7814-7818 (2007)).

The isopropanol, 4-hydroxybutyrate, or 1,4-butanediol can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the isopropanol, 4-hydroxybutyrate, or 1,4-butanediol producers can be cultured for the biosynthetic production of isopropanol, 4-hydroxybutyrate, or 1,4-butanediol.

For the production of isopropanol, 4-hydroxybutyrate, or 1,4-butanediol, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

In addition to renewable feedstocks such as those exemplified above, the isopropanol, 4-hydroxybutyrate, or 1,4-butanediol microbial organisms of the invention also can be modified for growth on syngas as its source of carbon. In this specific embodiment, one or more proteins or enzymes are expressed in the isopropanol, 4-hydroxybutyrate, or 1,4-butanediol producing organisms to provide a metabolic pathway for utilization of syngas or other gaseous carbon source.

Although organisms of the present invention are designed to utilize syngas and/or methanol as a growth source, they may also utilize, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of isopropanol, 4-hydroxybutyrate, or 1,4-butanediol.

Accordingly, given the teachings and guidance provided herein, those skilled in the art will understand that a non-naturally occurring microbial organism can be produced that secretes the biosynthesized compounds of the invention when grown on a carbon source such as syngas, methanol, or combinations of CO, $CO_2$, hydrogen, and the like. Such compounds include, for example, isopropanol, 4-hydroxybutyrate, or 1,4-butanediol and any of the intermediate metabolites in the isopropanol, 4-hydroxybutyrate, or 1,4-butanediol pathway. All that is required is to engineer in one or more of the required enzyme or protein activities to achieve biosynthesis of the desired compound or intermediate including, for example, inclusion of some or all of the isopropanol, 4-hydroxybutyrate, or 1,4-butanediol biosynthetic pathways. Accordingly, the invention provides a non-naturally occurring microbial organism that produces and/or secretes isopropanol, 4-hydroxybutyrate, or 1,4-butanediol when grown on a carbohydrate or other carbon source and produces and/or secretes any of the intermediate metabolites shown in the isopropanol, 4-hydroxybutyrate, or 1,4-butanediol pathway when grown on a carbohydrate or other carbon source. The isopropanol, 4-hydroxybutyrate, or 1,4-butanediol producing microbial organisms of the invention can initiate synthesis from an intermediate, for example, acetyl-CoA.

The non-naturally occurring microbial organisms of the invention are constructed using methods well known in the art as exemplified herein to exogenously express at least one nucleic acid encoding an isopropanol, 4-hydroxybutyrate, or 1,4-butanediol pathway enzyme or protein in sufficient amounts to produce isopropanol, 4-hydroxybutyrate, or 1,4-butanediol. It is understood that the microbial organisms of the invention are cultured under conditions sufficient to produce isopropanol, 4-hydroxybutyrate, or 1,4-butanediol. Following the teachings and guidance provided herein, the non-naturally occurring microbial organisms of the invention can achieve biosynthesis of isopropanol, 4-hydroxybutyrate, or 1,4-butanediol resulting in intracellular concentrations between about 0.1-2000 mM or more. Generally, the intracellular concentration of isopropanol, 4-hydroxybutyrate, or 1,4-butanediol is between about 3-1800 mM, particularly between about 5-1700 mM and more particularly between about 8-1600 mM, including about 100 mM, 200 mM, 500 mM, 800 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007. Any of these conditions can be employed with the non-naturally occurring microbial organisms as well as other anaerobic conditions well known in the art. Under such anaerobic conditions, the isopropanol, 4-hydroxybutyrate, or 1,4-butanediol producers can synthesize isopropanol, 4-hydroxybutyrate, or 1,4-butanediol at intracellular concentrations of 5-10 mM or more as well as all other concentrations exemplified herein. It is understood that, even though the above description refers to intracellular concentrations, isopropanol, 4-hydroxybutyrate, or 1,4-butanediol producing microbial organisms can produce isopropanol, 4-hydroxybutyrate, or 1,4-butanediol intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of isopropanol, 4-hydroxybutyrate, or 1,4-butanediol includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of isopropanol, 4-hydroxybutyrate, or 1,4-butanediol. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of isopropanol, 4-hydroxybutyrate, or 1,4-butanediol. Generally, and as with non-continuous culture procedures, the continuous and/or near-continuous production of isopropanol, 4-hydroxybutyrate, or 1,4-butanediol will include culturing a non-naturally occurring isopropanol, 4-hydroxybutyrate, or 1,4-butanediol producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of isopropanol, 4-hydroxybutyrate, or 1,4-butanediol can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the isopropanol, 4-hydroxybutyrate, or 1,4-butanediol producers of the invention for continuous production of substantial quantities of isopropanol, 4-hydroxybutyrate, or 1,4-butanediol, the isopropanol, 4-hydroxybutyrate, or 1,4-butanediol producers also can be, for example, simultaneously subjected to chemical synthesis procedures to convert the product to other compounds or the product can be separated from the fermentation culture and sequentially subjected to chemical conversion to convert the product to other compounds, if desired.

Important process considerations for a syngas fermentation are high biomass concentration and good gas-liquid mass transfer (Bredwell et al., *Biotechnol. Prog.* 15:834-844 (1999). The solubility of CO in water is somewhat less than that of oxygen. Continuously gas-sparged fermentations can be performed in controlled fermenters with constant off-gas analysis by mass spectrometry and periodic liquid sampling and analysis by GC and HPLC. The liquid phase can function in batch mode. Fermentation products such as alcohols, organic acids, and residual glucose along with residual methanol are quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids. The growth rate is determined by measuring optical density using a spectrophotometer (600 nm). All piping in these systems is glass or metal to maintain anaerobic conditions. The gas sparging is performed with glass fits to decrease bubble size and improve mass transfer. Various sparging rates are tested, ranging from about 0.1 to 1 vvm (vapor volumes per minute). To obtain accurate measurements of gas uptake rates, periodic challenges are performed in which the gas flow is temporarily stopped, and the gas phase composition is monitored as a function of time.

In order to achieve the overall target productivity, methods of cell retention or recycle are employed. One method to increase the microbial concentration is to recycle cells via a tangential flow membrane from a sidestream. Repeated batch culture can also be used, as previously described for production of acetate by *Moorella* (Sakai et al., *J. Biosci. Bioeng.* 99:252-258 (2005)). Various other methods can also be used (Bredwell et al., *Biotechnol. Prog.* 15:834-844 (1999); Datar et al., *Biotechnol. Bioeng.* 86:587-594 (2004)). Additional optimization can be tested such as overpressure at 1.5 atm to improve mass transfer (Najafpour and Younesi, *Enzyme Microb. Technol.* 38[1-2], 223-228 (2006)).

Once satisfactory performance is achieved using pure $H_2$/CO as the feed, synthetic gas mixtures are generated containing inhibitors likely to be present in commercial syngas. For example, a typical impurity profile is 4.5% $CH_4$, 0.1% $C_2H_2$, 0.35% $C_2H_6$, 1.4% $C_2H_4$, and 150 ppm nitric oxide (Datar et al., *Biotechnol. Bioeng.* 86:587-594 (2004)). Tars, represented by compounds such as benzene, toluene, ethylbenzene, p-xylene, o-xylene, and naphthalene, are added at ppm levels to test for any effect on production. For example, it has been shown that 40 ppm NO is inhibitory to *C. carboxidivorans* (Ahmed and Lewis, *Biotechnol. Bioeng.* 97:1080-1086 (2007)). Cultures are tested in shake-flask cultures before moving to a fermentor. Also, different levels of these potential inhibitory compounds are tested to quantify the effect they have on cell growth. This knowledge is used to develop specifications for syngas purity, which is utilized for scale up studies and production. If any particular component is found to be difficult to decrease or remove from syngas used for scale up, an adaptive evolution procedure is utilized to adapt cells to tolerate one or more impurities.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of isopropanol, 4-hydroxybutyrate, or 1,4-butanediol.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. patent application Ser. No. 11/891,602, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

It is understood that modifications which do not substantially affect the activity of the various embodiments of this invention are also included within the definition of the invention provided herein. Accordingly, the following examples are intended to illustrate but not limit the present invention.

Example I

ACS/CODH Gene Insertions in *E. coli*

This example describes the creation of *E. coli* plasmids that express the *M. thermoacetica* ACS/CODH operon genes including those required for CODH, ACS, methyltransferase, and the corrinoid iron-sulfur protein. This example further describes the expression these in *E. coli* resulting in observable CO oxidation activity, methyltransferase activity, and corrinoid iron-sulfur protein activity. Finally, this example demonstrates that *E. coli* tolerates high CO concentrations, and may even consume CO when the CO-utilizing gene products from *M. thermoacetica* are expressed.

Expression vectors were chosen from the set described by Lutz and Bujard (Lutz and Bujard, *Nucleic Acids Res.* 25:1203-1210 (1997)); these come with compatible replicons that cover a range of copy numbers. Additionally, each contains prA1-laco1; this T7 early gene promoter is inducible by IPTG and can lead to very high levels of transcription in the presence of IPTG and represses in other conditions. The ACS/CODH-encoding operon was cloned from Moth_1204 (cooC) to Moth_1197; a second version containing only Moth_1203 to Moth_1197 was also constructed. Both of these fragments (10-11 kbp) were confirmed by DNA sequence analysis. These were constructed in both p15A and ColE1-based vectors for medium to high copy numbers.

Figure 4:
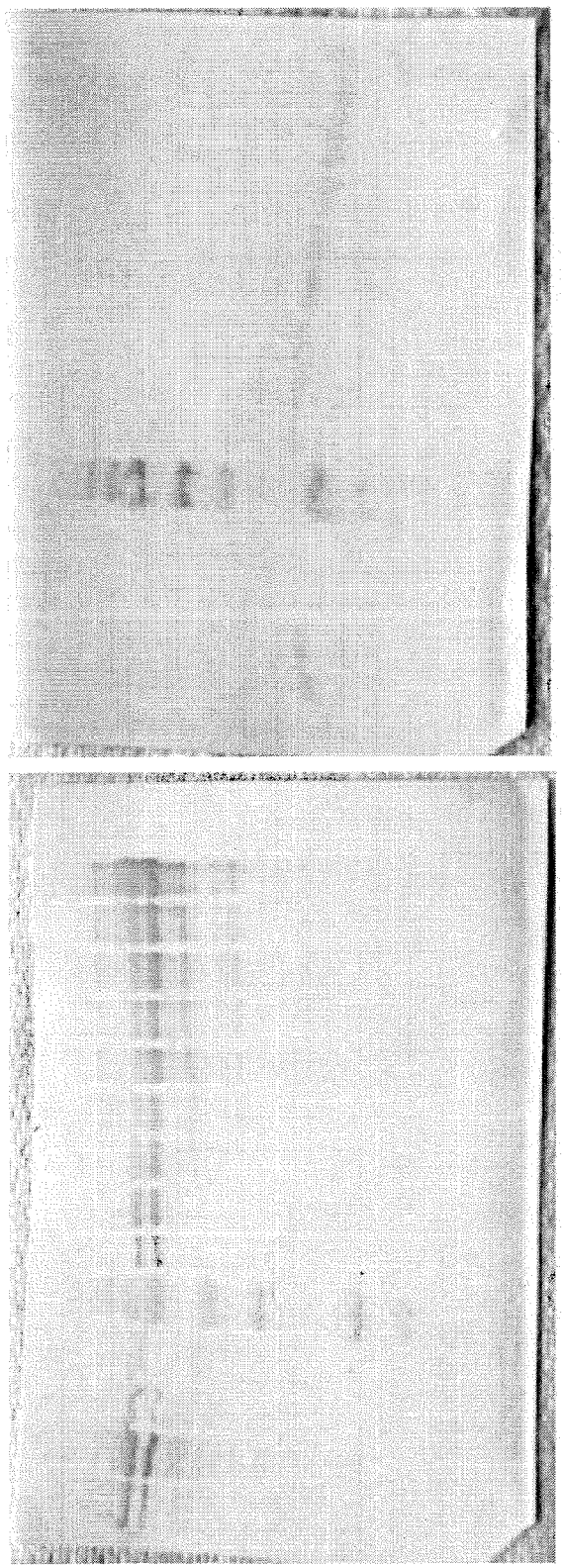
FIG. 4 shows Western blots of 10 micrograms ACS90 (lane 1), ACS91 (lane2), Mta98/99 (lanes 3 and 4) cell extracts with size standards (lane 5) and controls of M. thermoacetica CODH (Moth_1202/1203) or Mtr (Moth_1197) proteins (50, 150, 250, 350, 450, 500, 750, 900, and 1000 ng).

To estimate the final concentrations recombinant proteins, SDS-PAGE followed by Western blot analyses were performed on the same cell extracts used in the CO oxidation, ACS, methyltransferase, and corrinoid Fe—S assays. The antisera used were polyclonal to purified *M. thermoacetica* ACS/CODH and Mtr proteins and were visualized using an alkaline phosphatase-linked goat-anti-rabbit secondary antibody. The Westerns Blots are shown in FIGS. 4A and 4B. Amounts of CODH in ACS90 and ACS91 were estimated at 50 ng by comparison to the control lanes.

Figure 5:
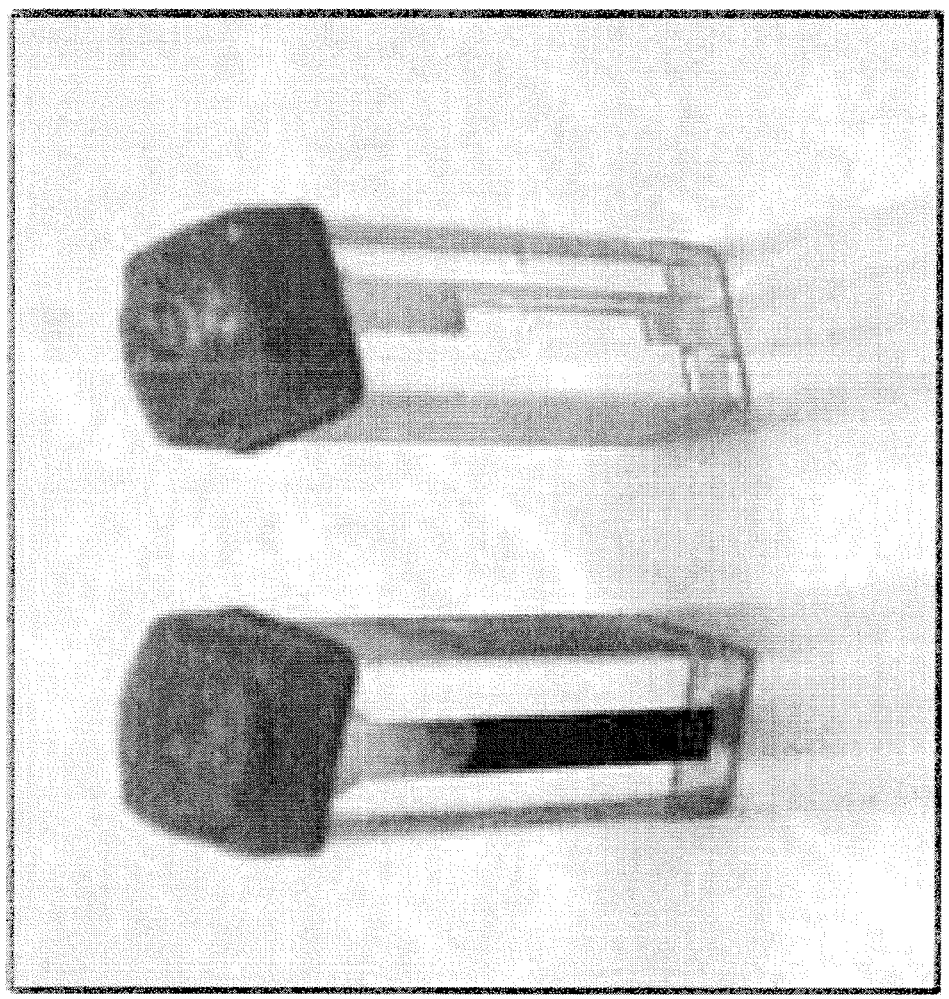
FIG. 5 shows cuvettes used in a methyl viologen assay. A blank is on the right and a cuvette with reduced methyl viologen is on the left. Stoppers and vacuum grease on top of each are used to keep the reactions anaerobic.

A carbon monoxide oxidation assay (Seravalli et al., *Biochemistry* 43:3944-3955 (2004)) was used to test whether or not functional expression of the CODH-encoding genes from *M. thermoacetica* was achieved. Cultures of *E. coli* MG1655 containing either an empty vector, or the vectors expressing "Acs90" or "Acs91" were grown in Terrific Broth under anaerobic conditions (with supplements of cyanocobalamin, ferrous iron, and reducing agents) until reaching medium to high density at which point, IPTG was added to a final concentration of 0.2 mM to induce the promoter. After 3.5 hrs of growth at 37 C, the cells were harvested and spun down prior to lysis with lysozyme and mild detergents. There is a benchmark figure of *M. thermoacetica* CODH specific activity, 500 U at 55 C or ~60 U at 25 C. This assay employed reduction of methyl viologen in the presence of CO. This is measured at 578 nm in stoppered, anaerobic, glass cuvettes. Reactions positive for CO oxidation by CODH turned a deep violet color (see FIG. 5). About 0.5% of the cellular protein was CODH as estimated by Western blotting; therefore, the data in Table 42 are approximately 50× less than the 500 U/mg activity of pure *M. thermoacetica* CODH. Nevertheless, this experiment did clearly demonstrate CO oxidation activity in recombinant *E. coli* with a much smaller amount in the negative controls. The small amount of CO oxidation ($CH_3$ viologen reduction) seen in the negative controls indicates that *E. coli* may have a limited ability to reduce $CH_3$ viologen.

TABLE 42

| ACS90 | 7.7 mg/ml | ACS91 | 11.8 mg/ml |
| Mta98 | 9.8 mg/ml | Mta99 | 11.2 mg/ml |

| Extract | Vol | OD/ | U/ml | U/mg |
|---|---|---|---|---|
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

Averages
ACS90 0.057 U/mg
ACS91 0.045 U/mg
Mta99 0.0018 U/mg

This assay is an in vitro reaction that synthesizes acetyl-CoA from methyl-tetrahydrofolate, CO, and CoA using ACS/CODH, methyltransferase, and CFeSP (Raybuck et al., *Biochemistry* 27:7698-7702 (1988)). By adding or leaving out each of the enzymes involved, this assay can be used for a wide range of experiments, from testing one or more purified enzymes or cell extracts for activity, to determining the kinetics of the reaction under various conditions or with limiting amounts of substrate or enzyme. Samples of the reaction taken at various time points are quenched with 1M HCl, which liberates acetate from the acetyl-CoA end product. After purification with Dowex columns, the acetate can be analyzed by chromatography, mass spectrometry, or by measuring radioactivity. The exact method will be determined by the specific substrates used in the reaction.

This assay was run in order to determine if the ACS/CODH operon expressed in *E. coli* expresses the Fe—S corrinoid protein activity. Therefore, 14C-labeled methyl-THF was used as a labeled substrate to measure acetate synthesis by radioactivity incorporation into isolated acetate samples. Six different conditions were tested:

1. Purified ACS/CODH, MeTr, and CFeSP as a positive control
2. Purified ACS/CODH with ACS90 cell extract
3. Purified ACS/CODH with ACS91 cell extract
4. Purified ACS/CODH, MeTr with ACS90 cell extract
5. Purified ACS/CODH, MeTr with ACS91 cell extract
6. Purified ACS/CODH, MeTr with as much ACS91 cell extract as possible (excluding the MES buffer)

The reaction was assembled in the anaerobic chamber in assay vials filled with CO. The total reaction volume was small compared to the vial volume, reagents were added prior to filling with CO, a gas-tight Hamilton syringe was used and the reagents were kept anaerobic. The reaction (~60 ul total) consisted of the cell extract (except #1), CoA, Ti(III)citrate, MES (except #6), purified ACS/CODH, 14C-methyl-tetrahydrofolate, methyl-viologen, and ferredoxin. Additionally, purified MeTr was added to #1, #4-6 and purified CFeSP was added to #1.

The reaction was carried out in the anaerobic chamber in a sand bath at 55°. The final reagent added was the 14C-methyl-tetrahydrofolate, which started the reaction (t=0s). An initial sample was taken immediately, followed by samples at 30 minutes, 1 hour, and 2 hours. These time points are not exact, as the 6 conditions were run concurrently (since this experiment was primarily a qualitative one). The 15 ul samples were added to 15 ul of 1M HCl in scintillation vials. After counting the reaction mixtures, it was determined that the corrinoid Fe—S protein in ACS90 extracts was active with total activity approaching approximately ⅓ of the positive control.

Within the ACS/CODH operon is encoded an essential methyltransferase activity that catalyzes the transfer of $CH_3$ from methyl-tetrahydrofolate to the ACS complex as part of the synthesis of acetyl-CoA (i.e. this is the step that the methyl and carbonyl paths join together). Within the operon in *M. thermoacetica*, the Mtr-encoding gene is Moth 1197 and comes after the main CODH and ACS subunits. Therefore, Mtr activity would constitute indirect evidence that the more proximal genes can be expressed.

Figure 6:
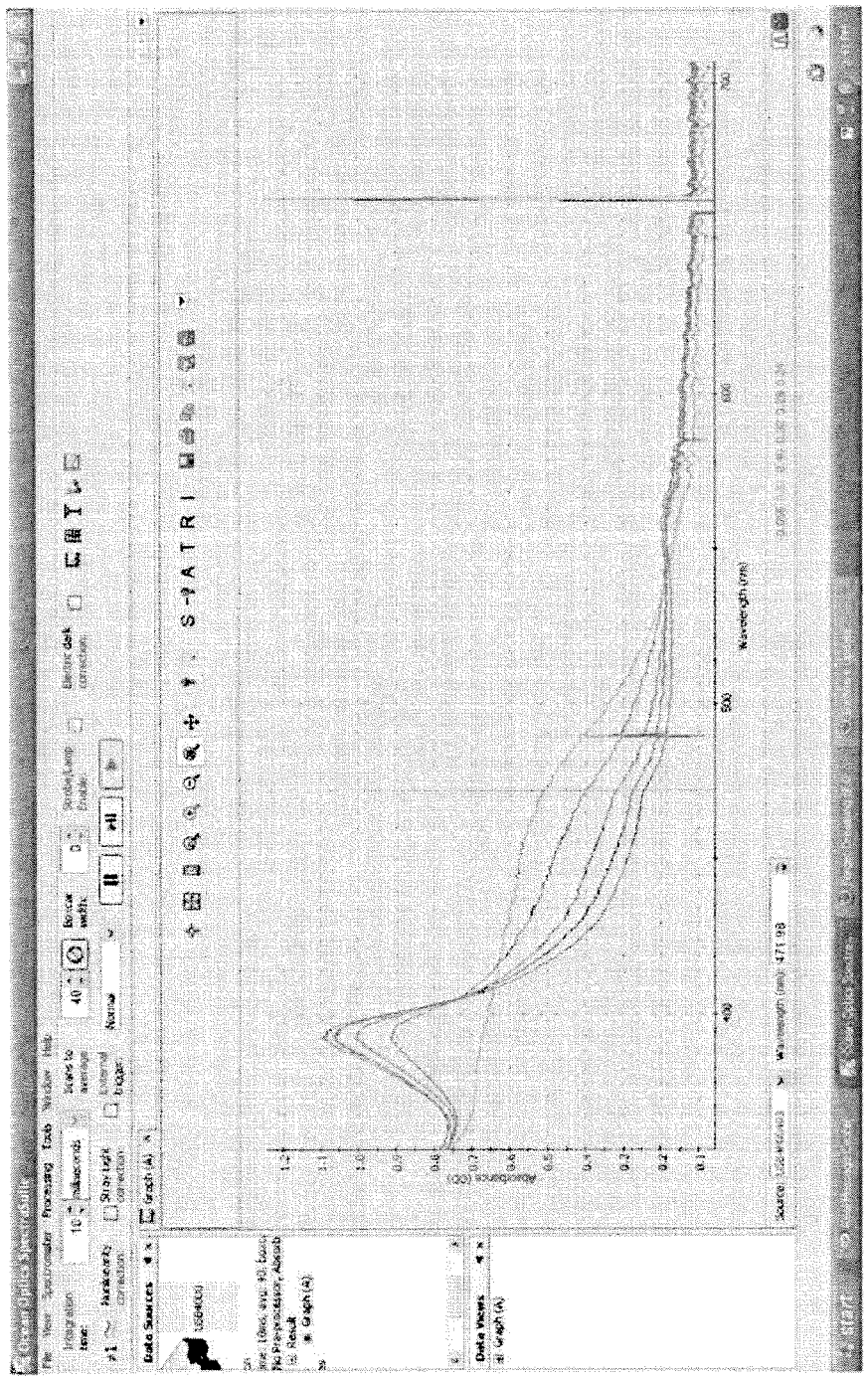
FIG. 6 shows a spectrogram of ACS90 cell extracts assayed for transfer of $CH_3$ from added $CH_3$-THF to purified M. thermoacetica corrinoid protein.

Mtr activity was assayed by spectroscopy. Specifically, methylated CFeSP, with Co(III), has a small absorption peak at ~450 nm, while non-methylated CFeSP, with Co(I), has a large peak at 390 nm. This spectrum is due to both the cobalt and iron-sulfur cluster chromophores. Additionally, it should be noted that the CFeSP can spontaneously oxidize to Co(II), which creates a broad absorption peak at ~470 nm (Seravalli et al., *Biochem.* 38:5728-5735 (1999)). See FIG. 6 for the results from *E. coli* cells containing ACS90.

Figure 7:
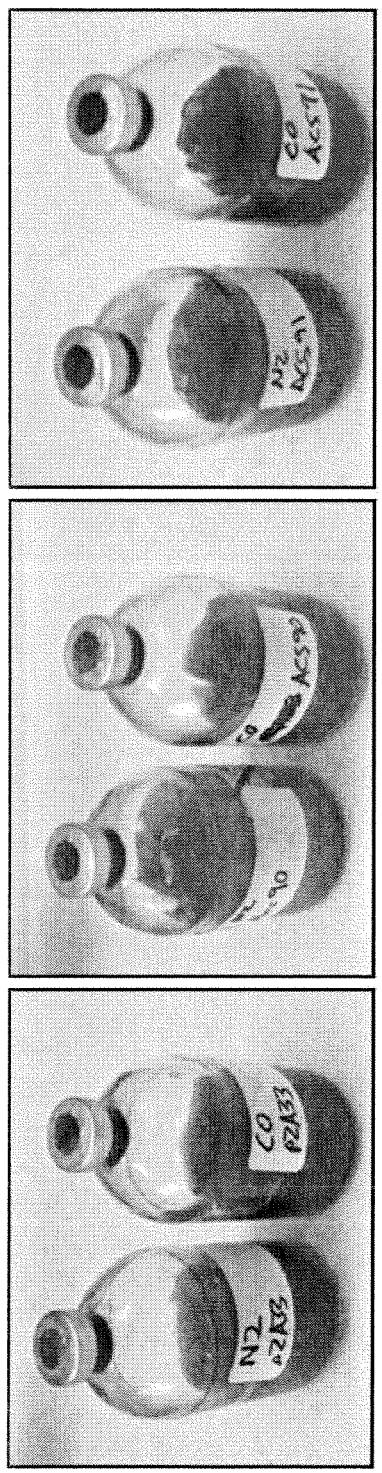
FIG. 7 shows anaerobic growth of recombinant E. coli MG1655 in $N_2$ and CO for 36 hr at 37° C. From left to right: Empty vector, ACS90, and ACS91 are shown.

To test whether or not *E. coli* can grow anaerobically in the presence of saturating amounts of CO, 120 ml serum bottles with 50 ml of Terrific Broth medium (plus $NiCl_2$, Fe(II) $NH_4SO_4$, and cyanocobalamin) were made in anaerobic conditions. One half of these bottles were equilibrated with nitrogen gas for 30 min. and one half was equilibrated with CO gas for 30 min. An empty vector (pZA33) was used as a control and that and both ACS90 and ACS91 were tested with both $N_2$ and CO. All were grown for 36 hrs with shaking (250 rpm) at 37 C. At the end of the 36 period, examination of the flasks showed high amounts of growth in all (FIG. 7). The bulk of the observed growth occurred overnight with a long lag of some (low but visible) density. Inocula sizes were ~0.5 ml from E. coli stocks.

The final CO concentrations are measured using an assay of the spectral shift of myoglobin upon exposure to CO. Myoglobin reduced with sodium dithionite has an absorbance peak at 435 nm; this peak is shifted to 423 nm with CO. Due to the low wavelength (and need to record a whole spectrum from 300 nm on upwards) quartz cuvettes must be used. CO concentration is measured against a standard curve and depends upon the Henry's Law constant for CO of maximum water solubility=970 micromolar at 20 C and 1 atm.

The results shown in Table 43 are very encouraging. Growth reached similar levels (by visual inspection) whether or not a strain was cultured in the presence of CO or not. Furthermore, the negative control had a final CO concentration of 930 micromolar vs. 688 and 728 micromolar for the ACS/CODH operon expressing strains. Clearly, the error in these measurements is high given the large standard deviations. Nevertheless, this test does allow two tentative conclusions: 1) E. coli can tolerate exposure to CO under anaerobic conditions, and 2) E. coli cells expressing the ACS/CODH operon might be metabolizing some of the CO. The second conclusion is significantly less certain than the first.

TABLE 43

| Stain and Growth Conditions pZA33-CO | Final CO concentration (micromolar) |
|---|---|
| ACS90-CO | 638 |
|  | 494 |
|  | 734 |
|  | 883 |
| ave | 687 |
| SD | 164 |
| ACS91-CO | 728 |
|  | 812 |
|  | 760 |
|  | 611 |
| ave. | 728 |
| SD | 85 |

Example II

Enhancing the Yield of Fermentation Products from Sugars with Wood-Ljungdahl Pathway Enzymes In this example, we describe a non-naturally occurring microorganism expressing genes encoding enzymes that catalyze the carbonyl-branch of the Wood-Ljungdahl pathway. Wood-Ljungdahl pathway enzymes assimilate carbon in the form of CO and/or CO2 into acetyl-CoA, which can subsequently be converted to useful chemical products such as isopropanol, 4-hydroxybutyrate (4-HB) and 1,4-butanediol (14-BDO). The Wood-Ljungdahl pathway can also serve as a secondary carbon assimilation pathway during growth on other substrates such as glucose. In this capacity, WL pathway enzymes harness reducing equivalents generated in glycolysis to convert $CO_2$ to acetyl-CoA, cell mass and downstream products at high yield.

Isopropanol: Engineering a Wood-Ljungdahl pathway into a glucose-utilizing and isopropanol-producing organism improves the maximum isopropanol yield up to 33%. The production of isopropanol has been demonstrated in E. coli (Nahvi et al., Chem. Biol. 9:1043 (2002)). Specifically, acetyl CoA can be converted into acetoacetyl CoA, transformed into acetoacetate, decarboxylated to form acetone and then reduced to form isopropanol (see FIG. 1). This pathway is redox-imbalanced and yields only 1 mol IPA/mol glc or 0.333 g/g. If the IPA pathway is supplemented with $CO_2$-fixation by the Wood-Ljungdahl pathway, the theoretical stoichiometric yield of IPA (1.33 mol/mol, 0.444 lb/lb) is achievable, the pathway is redox-balanced, and can generate energy.

Figure 8A:
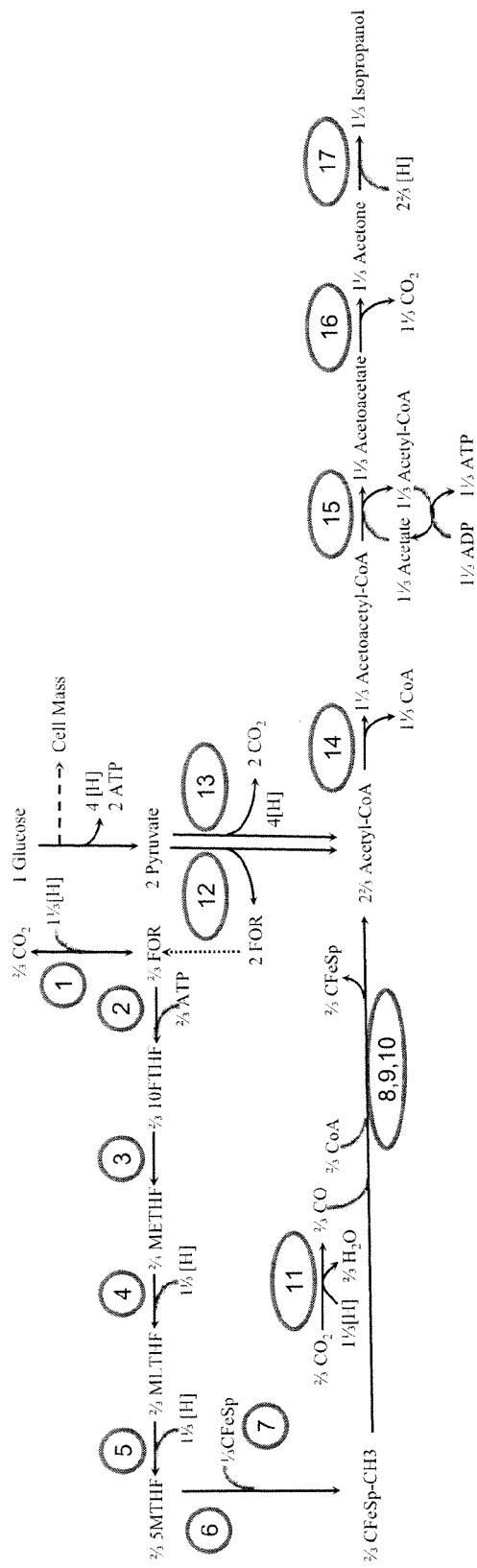
FIG. 8A shows a synthetic metabolic pathway and exemplary flux distribution for the conversion of carbohydrates and $CO_2$ to acetyl-CoA, and further to isopropanol.

FIG. 8A shows a flux distribution for the conversion of one mole of glucose into 1.33 moles of isopropanol. The conversion of one mole of glucose to two moles of pyruvate generates four reducing equivalents and two ATPs. Pyruvate is subsequently converted to molar quantities of acetyl-CoA by one or more enzymes including pyruvate formate lyase (PFL), pyruvate dehydrogenase (PDH) or pyruvate ferredoxin oxidoreductase (PFOR). PDH and PFOR generate molar quantities of $CO_2$ and two reducing equivalents per pyruvate consumed. Pyruvate formate lyase forms formate as a byproduct, which can be converted to CO, and two reducing equivalents by formate dehydrogenase. In the absence of WL pathway enzymes, the two moles of acetyl-CoA are converted to one mole of isopropanol. Assuming reducing equivalents are generated from the pyruvate to acetyl-CoA conversion, this pathway generates an excess of 3 reducing equivalents per glucose consumed. When an active WL pathway is present 0.66 moles of $CO_2$ or formate (per mole glucose consumed) are assimilated into acetyl-CoA, which is subsequently converted to 0.33 moles of isopropanol. This combined glycolysis/Wood Ljungdahl pathway is exactly balanced from a redox standpoint and is also capable of generating energy. Two ATPs are generated in the conversion of glucose to pyruvate. In this example, an additional 1.33 ATPs are recovered from conversion of acetyl-CoA to acetate, yielding a total supply of 3.33 ATPs per glucose consumed. The Wood-Ljungdahl pathway consumes 0.67 ATPs leaving 2.67 ATPs available for cell growth and metabolism.

Figure 8B:
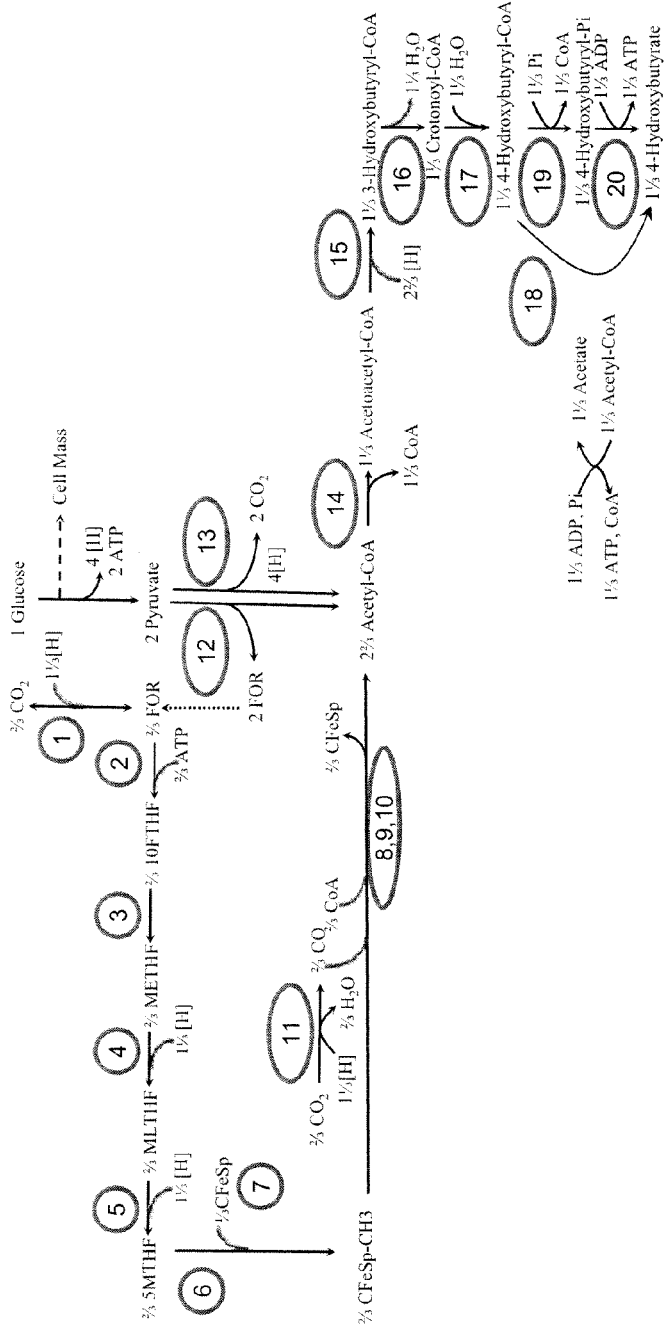
FIG. 8B shows a synthetic metabolic pathway and exemplary flux distribution for the conversion of carbohydrates and $CO_2$ to acetyl-CoA, and further to 4-hydroxybutyrate.

4-Hydroxybutyrate: A similar improvement in yield is achievable for the production of 4-hydroxybutyrate. The maximum 4-HB yield from glucose alone is 1 mole 4-HB per mole glucose consumed (0.578 g/g). The pathway, shown in FIG. 8B, is redox-imbalanced and requires aeration and/or the formation of fermentation byproducts. An organism with a WL pathway can achieve the maximum stoichiometric yield of 4-HB (1.33 mol/mol or 0.768 g/g). A flux distribution of the maximum theoretical yield is shown in FIG. 8B. Like the isopropanol pathway described previously, the pathway is redox-balanced and yields a maximum availability of 2.67 ATP for cell growth and maintenance.

Figure 8C:
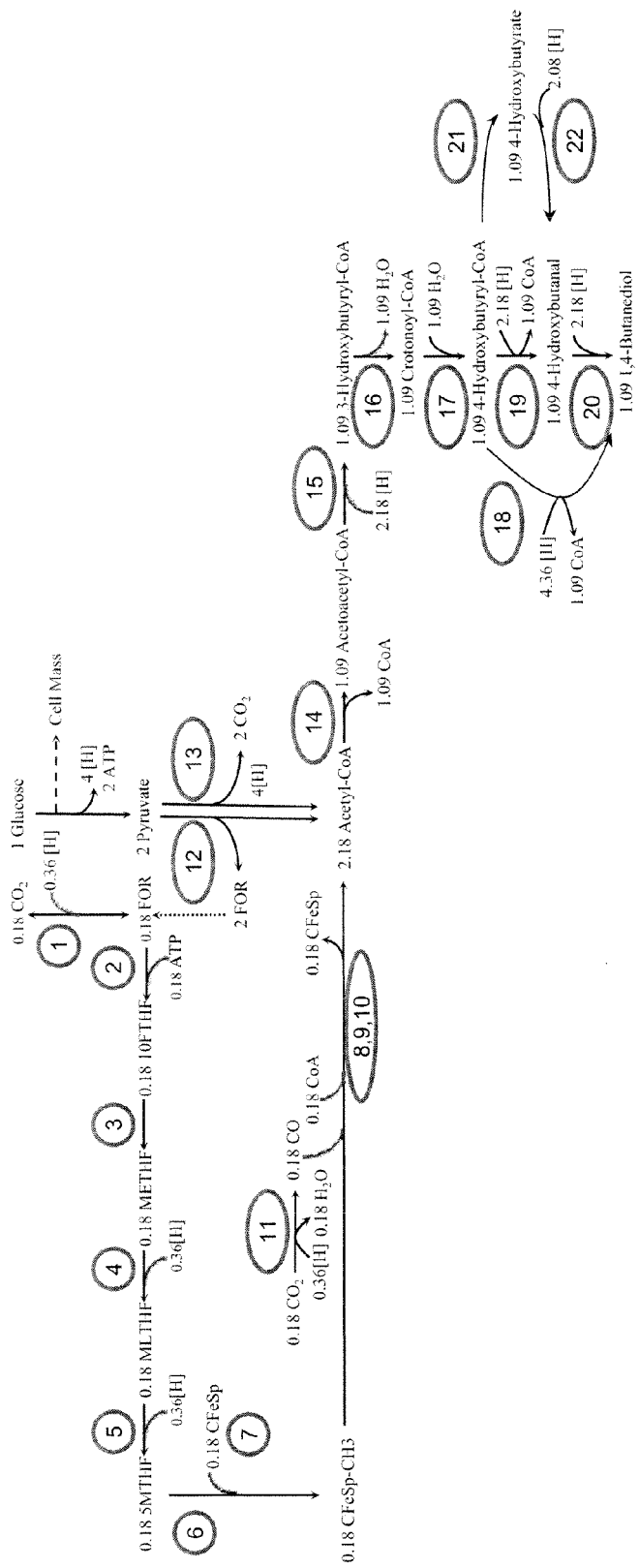
FIG. 8C shows a synthetic metabolic pathway and exemplary flux distribution for the conversion of carbohydrates and $CO_2$ to acetyl-CoA, and further to 1,4-butanediol.

1,4-Butanediol: 1,4-Butanediol can also be synthesized from acetyl-CoA via the intermediate 4-hydroxybutyryl-CoA. In this pathway, acetoacetyl-CoA is converted to 4-hydroxybutyryl-CoA as described previously in the 4-hydroxybutyrate pathway. 4-Hydroxybutyryl-CoA is subsequently converted to 14-BDO by a bifunctional aldehyde dehydrogenase or a CoA-dependent aldehyde dehydrogenase and alcohol dehydrogenase. Alternatively, it can be converted to 4-hydroxybutyrate which can be first reduced directly to 4-hydroxybutyraldehyde and subsequently reduced to 1,4-butanediol. As this pathway is not redox-balanced, the maximum 14-BDO yield of this pathway from sugars is 1 mol/mol (0.5 g/g). Additional assimilation of CO) via Wood-Ljungdahl pathway further improves the yield to the theoretical maximum of 1.09 mol/mol (0.545 g/g). A predicted flux distribution for achieving the maximum theoretical yield is shown in FIG. 8C. In this pathway, 2 ATPs are generated in glycolysis and 0.18 ATPs are consumed in the WL pathway, leaving a maximum of 1.82 ATPs available for cell growth and maintenance.

Example III

Enhancing the Yield of Fermentation Products from Sugars with Wood-Ljungdahl Pathway Enzymes and a MtaABC-Type Methyltransferase System An organism engineered to express genes encoding an ACS/CODH enzyme and a MtaABC-type methyltransferase system is capable of producing acetyl-CoA and downstream products at high yields from glucose and methanol. The methyltransferase system enables the assimilation of methanol into 5-methyl-tetrahydrofolate (Me-THF). The CODH/ACS enzyme confers the functionality to convert $CO_2$ to CO and CO, CoA and Me-THF to acetyl-CoA. The recombinant organism can be further engineered to transform acetyl-CoA to products of interest such as isopropanol, 4-hydroxybutyrate, or 1,4-butanediol. Microorganisms with these features are capable of metabolizing sugars in conjunction with methanol to achieve high yields of chemical products. The ratio of glucose to methanol consumed impacts the overall product yield.

Figure 9:
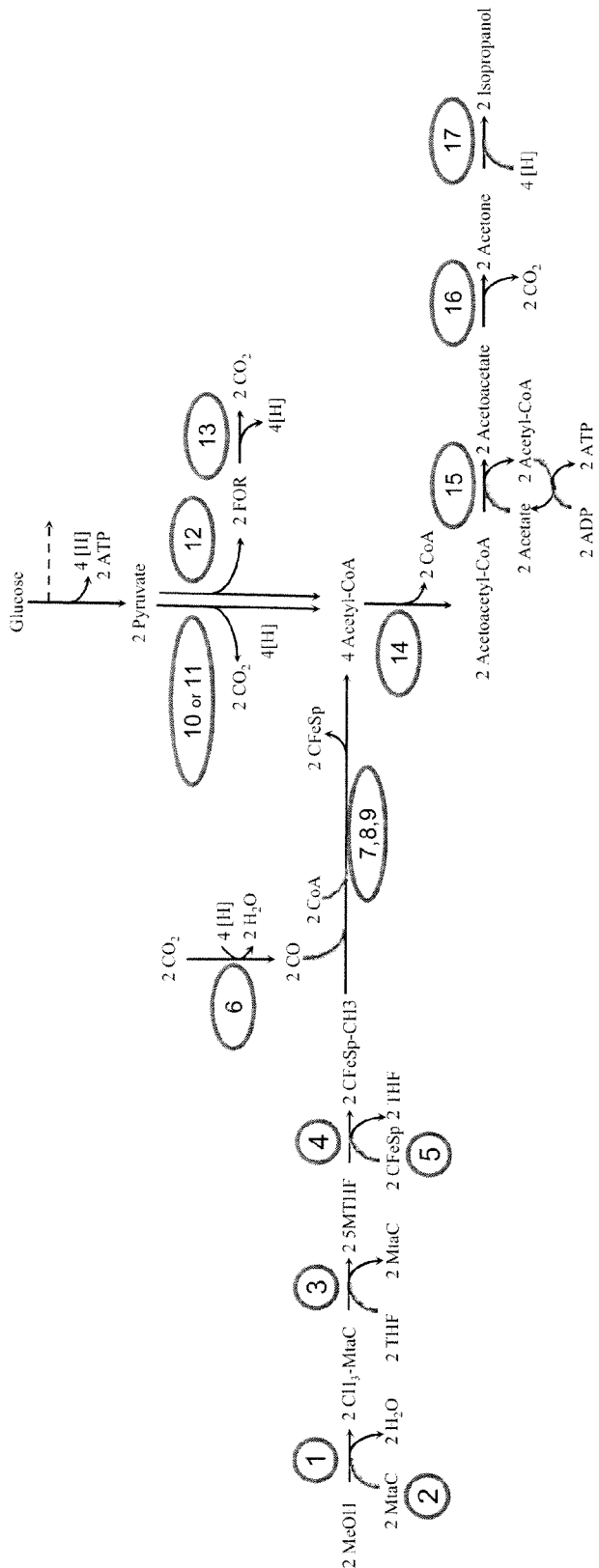
FIG. 9 shows a synthetic metabolic pathway and exemplary flux distribution for the conversion of carbohydrates, methanol and $CO_2$ to acetyl-CoA, and further to isopropanol. Several enzymatic transformations that can be engineered into a production host are numbered.
Figure 10:
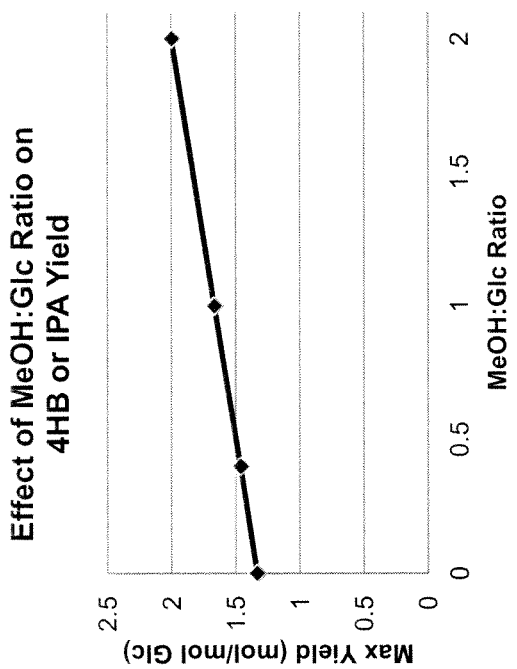
FIG. 10 plots the maximum yield of isopropanol or 4-hydroxybutyrate as a function of the glucose: methanol ratio.

An organism engineered to produce isopropanol from glucose via acetyl-CoA achieves a maximum isopropanol yield of 1 mole product per mole glucose utilized. Co-feeding methanol to this organism at a ratio of 2 methanol per one glucose further increases the yield to a maximum of 2 moles isopropanol per mole of glucose consumed. In the maximum yield scenario 2 moles of methanol are utilized per glucose consumed, producing 2 moles of IPA. In addition, 2 moles of $CO_2$ are assimilated into acetyl-CoA via ACS/CODH. The reduction of $CO_2$ to CO by ACS/CODH consumes reducing equivalents, enabling redox balance and improved product yield. The energetic yield of this pathway is also favorable, with 4 ATP equivalents generated per glucose consumed. An exemplary flux distribution of the conversion of methanol and glucose to isopropanol is shown in FIG. 9. The relationship between the glucose/methanol feed ratio and the maximum product yield in FIG. 10.

A similar improvement in yield is observed for a 4-HB-producing organism utilizing the 4-HB pathway from acetyl-CoA in FIG. 2. One mole of glucose and two moles each of methanol and $CO_2$ are assimilated in a redox-balanced pathway to form two moles of 4-hydroxybutyrate. Similarly, the yield of 1,4-BDO from carbohydrates can be improved by co-utilizing methanol.

Example IV

Engineering Cobalamin Synthesis into an Organism

The key enzyme of the Wood-Ljungdahl pathway, ACS/CODH, requires cobalamin (vitamin $B_{12}$) to function. $B_{12}$ is synthesized de novo in some organisms but must be supplied exogenously to others. Still other organisms such as *S. cerevisiae* lack the ability to efficiently uptake $B_{12}$. This example describes a strategy for engineering de novo $B_{12}$ synthetic capability into an organism.

$B_{12}$ biosynthetic pathways have been characterized in several organisms including *Salmonella typhimurium* LT2 (Roth et al., *J. Bacteriol.* 175:3303-3316 (1993)), *Lactobacillus reuteri* CRL1098 (Sennett et al., *Annu. Rev. Biochem.* 50:1053-1086 (1981)) and *Bacillus megaterium* (Brey et al., *J. Bacteriol.* 167:623-630 (1986)). Bacterial $B_{12}$ biosynthesis pathways involve 20-30 genes clustered together in one or more operons. Two cobalamin biosynthesis pathways: late-insertion (aerobic only) and early-insertion (anaerobic) have been described (Scott, A. I., *J. Org. Chem.* 68:2529-2539 (2003)). The final products of the biosynthesis of vitamin $B_{12}$ are 5'-deoxyadenosylcobalamin (coenzyme $B_{12}$) and methylcobalamin (MeCbl). Vitamin $B_{12}$ is defined as cyanocobalamin (CNCbl) which is the form commonly prepared in industry. In this example, $B_{12}$ refers to all three analogous molecules.

The anaerobic cobalamin biosynthesis pathway has been well-characterized in *Salmonella typhimurium* LT2 (Roth et al., *J. Bacteriol.* 175:3303-3316 (1993)). Pathway genes are clustered in a large operon termed the cob operon. A plasmid containing the following 20 genes from the cob operon (pAR8827) was transformed into *E. coli* and conferred the ability to synthesize cobalamin de novo (Raux et al., *J. Bacteriol.* 178:753-767 (1996)). To further improve yield of the cobyric acid precursor, the authors removed the known regulatory elements of cbiA and altered the RBS. The genes and corresponding GenBank identifiers and gi numbers are listed below.

TABLE 44

| Protein | GenBank ID | GI Number | Organism |
| --- | --- | --- | --- |
| cysG | NP_462380.1 | 16766765 | *Salmonella typhimurium* |
| cbiK | NP_460970.1 | 16765355 | *Salmonella typhimurium* |
| cbiL | NP_460969.1 | 16765354 | *Salmonella typhimurium* |
| cbiH | NP_460972.1 | 16765357 | *Salmonella typhimurium* |
| cbiF | NP_460974.1 | 16765359 | *Salmonella typhimurium* |
| cbiG | NP_460973.1 | 16765358 | *Salmonella typhimurium* |
| cbiD | NP_460977.1 | 16765362 | *Salmonella typhimurium* |
| cbiJ | NP_460971.1 | 16765356 | *Salmonella typhimurium* |
| cbiE | NP_460976.1 | 16765361 | *Salmonella typhimurium* |
| cbiT | NP_460975.1 | 16765360 | *Salmonella typhimurium* |
| cbiC | NP_460978.1 | 16765363 | *Salmonella typhimurium* |
| cbiA | NP_460980.1 | 16765365 | *Salmonella typhimurium* |
| fldA | NP_459679.1 | 16764064 | *Salmonella typhimurium* |
| cobA | P31570.1 | 399274 | *Salmonella typhimurium* |
| cbiP | AAA27268.1 | 154436 | *Salmonella typhimurium* |
| cbiB | Q05600.1 | 543942 | *Salmonella typhimurium* |
| cobU | NP_460963.1 | 16765348 | *Salmonella typhimurium* |
| cobT | NP_460961.1 | 16765346 | *Salmonella typhimurium* |
| cobs | AAA27270.1 | 154438 | *Salmonella typhimurium* |
| cobC | NP_459635.1 | 16764020 | *Salmonella typhimurium* |
| cysG | NP_462380.1 | 16766765 | *Salmonella typhimurium* |

Some organisms unable to synthesize $B_{12}$ de novo are able to catalyze some steps of the pathway. *E. coli*, for example, is unable to synthesize the corrin ring structure but encodes proteins that catalyze several reactions in the pathway (Raux et al., *J. Bacteriol.* 178:753-767 (1996)). The cysG gene encodes a functional CysG, a multifunctional enzyme that converts uroporphyrinogen III to precorrin-2 (Hugler et al., *J. Bacteriol.* 184:2404-2410 (2002); Ishige et al., *Appl. Environ. Microbiol.* 68:1192-1195 (2002)). The proteins encoded by cobTSU transform cobinamide to cobalamin and introduce the 5'-deoxyadenosyl group (Raux et al., *J. Bacteriol.* 178: 753-767 (1996)).

TABLE 45

| Protein | GenBank ID | GI Number | Organism |
| --- | --- | --- | --- |
| cobT | NP_416495.1 | 16129932 | *Escherichia coli* K12 sp. MG1655 |

TABLE 45-continued

| Protein | GenBank ID | GI Number | Organism |
|---------|------------|-----------|----------|
| cobS | NP_416496.1 | 16129933 | *Escherichia coli* K12 sp. MG1655 |
| cobU | NP_416497.1 | 16129934 | *Escherichia coli* K12 sp. MG1655 |
| cysG | NP_417827.1 | 16131246 | *Escherichia coli* K12 sp. MG1655 |

*S. cerevisiae* is not able to synthesize $B_{12}$ de novo, nor is it able to uptake the vitamin at detectable levels. However, the *S. cerevisiae* genome encodes two proteins, Met1p and Met8p, that catalyze several $B_{12}$ pathway reactions. Met1p is analogous to the uroporphyrinogen III transmethylase CysG of *S. typhimurium*, which catalyzes the first step of B12 biosynthesis from uroporphyrinogen III (Raux et al., *Biochem. J.* 338 (Pt 3):701-708 (1999)). The Met8p protein is a bifunctional protein with uroporphyrinogen III transmethylase activity and cobaltochelatase activity analogous to the CysG of *B. megaterium* (Raux et al., *Biochem. J.* 338 (Pt 3):701-708 (1999)).

TABLE 46

| Protein | GenBank ID | GI Number | Organism |
|---------|------------|-----------|----------|
| Met1p | NP_012995.1 | 6322922 | *Saccharomyces cerevisiae* |
| Met8p | NP_009772.1 | 6319690 | *Saccharomyces cerevisiae* |

Any or all of these genes can be introduced into an organism deficient or inefficient in one or more components of cobalamin synthesis to enable or increase the efficiency of cobalamin synthesis.

Example V

Engineering Enhanced Cobalamin Uptake Capability in an Organism

This example describes engineering $B_{12}$ uptake capability into a host organism. $B_{12}$ uptake requires a specific transport system (Sennett et al., *Annu. Rev. Biochem.* 50:1053-1086 (1981)). The $B_{12}$ transport system of *E. coli* has been extensively studied. High-affinity transport across the outer membrane is calcium-dependent and mediated by a 66 kDa outer membrane porin, BtuB (Heller et al., *J. Bacteriol.* 161:896-903 (1985)). BtuB interacts with the TonB energy transducing system (TonB-ExbB-ExbD), facilitating energy-dependent translocation and binding to periplasmic binding protein BtuF (Heller et al., *J. Bacteriol.* 161:896-903 (1985); Raux et al., *J. Bacteriol.* 178:753-767 (1996)). Transport across the inner membrane is facilitated by an ABC type uptake system composed of BtuF, BtuD (ATP binding component) and BtuC (permease) (Raux et al., *Biochem. J.* 338 (Pt 3):701-708 (1999)). Crystal structures of the BtuCDF complex are available (Raux et al., *J. Bacteriol.* 178:753-767 (1996); Raux et al., *Biochem. J.* 338 (Pt 3):701-708 (1999)). An additional protein, BtuE, is coexpressed in the btuCED operon, but this protein is not required for B12 transport and its function is unknown (Rioux and Kadner, *Mol. Gen. Genet.* 217:301-308. (1989)). The btuCED operon is constitutively expressed. The GenBank identifiers and GI numbers of the genes associated with $B_{12}$ transport are listed below.

TABLE 47

| Protein | GenBank ID | GI Number | Organism |
|---------|------------|-----------|----------|
| btuB | NP_418401.1 | 16131804 | *Escherichia coli* K12 sp. MG1655 |
| btuC | NP_416226.1 | 16129667 | *Escherichia coli* K12 sp. MG1655 |
| btuD | NP_416224.1 | 16129665 | *Escherichia coli* K12 sp. MG1655 |
| btuF | NP_414700.1 | 16128151 | *Escherichia coli* K12 sp. MG1655 |
| tonB | NP_415768.1 | 16129213 | *Escherichia coli* K12 sp. MG1655 |
| exbB | NP_417479.1 | 16130904 | *Escherichia coli* K12 sp. MG1655 |
| exbD | NP_417478.1 | 16130903 | *Escherichia coli* K12 sp. MG1655 |

The $B_{12}$ uptake capability of an organism can be further improved by overexpressing genes encoding the requisite transport proteins, and reducing or eliminating negative regulatory control. Overexpressing the btuBCDF genes leads to increased binding of B12 to membranes and increased rate of uptake into cells. Another strategy is to remove regulatory control. The btuB mRNA translation is directly repressed by B12 at the 5' UTR (Nahvi et al., *Chem. Biol.* 9:1043 (2002)). This interaction may induce mRNA folding to block ribosome access to the translational start. Mutation or elimination of the $B_{12}$ binding site removes inhibition and improves the efficiency of $B_{12}$ uptake (Bulthuis et al., U.S. Pat. No. 6,432, 686). These strategies were successfully employed to improve $B_{12}$ uptake capability in 1,3-PDO producing microorganisms (WO/1999/058686) and (Bulthuis et al., U.S. Pat. No. 6,432,686). A recent patent application describes improving the efficiency of $B_{12}$ uptake (WO/2008/152016) by deleting negative regulatory proteins such as *C. glutamicum* btuR2.

*S. typhimurium* possesses both high and low affinity transporters for $B_{12}$. The high affinity transporter is encoded by btuB (Rioux and Kadner, *J. Bacteriol.* 171:2986-2993 (1989)). Like *E. coli* transport across the periplasmic membrane is predicted to occur via an ABC transport system, although this has not been characterized to date. The $B_{12}$ binding protein is encoded by btuD and btuE, and btuC is predicted to encode the permease.

TABLE 48

| Protein | GenBank ID | GI Number | Organism |
|---------|------------|-----------|----------|
| btuB | AAA27031.1 | 153891 | *Salmonella typhimurium* LT2 |
| btuC | NP_460306.1 | 16764691 | *Salmonella typhimurium* LT2 |
| btuD | NP_460308.1 | 16764693 | *Salmonella typhimurium* LT2 |
| btuE | AAL20266.1 | 16419860 | *Salmonella typhimurium* LT2 |

Any or all of these genes can be introduced into an organism deficient in one or more components of cobalamin uptake to enable or increase the efficiency cobalamin uptake.

Method for Quantifying $B_{12}$ in the Culture Medium.

To quantify the amount of $B_{12}$ in the culture medium, cell free samples are run on HPLC. Cobalamin quantification is achieved by comparing peak area ratios at 278 nm and 361 nm with standards, then applying peak areas to standard curves of cobalamin.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should understood that various modifications can be made without departing from the spirit of the invention. Accordingly, the invention is limited only by the following claims.

What is claimed is:

1. A non-naturally occurring microbial organism comprising:
   (i) a 1,4-butanediol pathway, wherein said microbial organism comprises at least one exogenous nucleic acid encoding a 1,4-butanediol pathway enzyme expressed in a sufficient amount to produce 1,4-butanediol, wherein said 1,4-butanediol pathway enzyme is selected from the group consisting of an acetoacetyl-CoA thiolase, a 3-hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), and a 1,4-butanediol dehydrogenase; and
   (ii) an acetyl-CoA pathway, wherein said microbial organism comprises at least one exogenous nucleic acid encoding an acetyl-CoA pathway enzyme expressed in a sufficient amount to produce acetyl-CoA, wherein said acetyl-CoA pathway enzyme is selected from the group consisting of a corrinoid protein, a methyltetrahydrofolate:corrinoid protein methyltransferase, a corrinoid iron-sulfur protein, a nickel-protein assembly protein, a ferredoxin, a carbon monoxide dehydrogenase, a pyruvate ferredoxin oxidoreductase, and a hydrogenase.

2. The organism of claim 1, wherein said acetoacetyl-CoA thiolase is encoded by a gene selected from the group consisting of atoB, thlA, thlB, and erg10.

3. The organism of claim 1, wherein said 3-Hydroxybutyryl-CoA dehydrogenase is encoded by a gene selected from the group consisting of hbd, msed_1423, msed_0399, msed_0389, and msed_1933.

4. The organism of claim 1, wherein said crotonase is encoded by a gene selected from the group consisting of crt, paaA, paaB, phaA, phaB, maoC, paaF, and paaG.

5. The organism of claim 1, wherein said crotonyl-CoA hydratase is encoded by a gene selected from the group consisting of abfD, msed_1321, and msed_1220.

6. The organism of claim 1, wherein said 4-hydroxybutyryl-CoA reductase (alcohol forming) is encoded by a gene selected from the group consisting of adhE, adhE2, mcr, rcas_2929, nap1_02720, and mgp2080_00535.

7. The organism of claim 1, wherein said 4-hydroxybutyryl-CoA reductase (aldehyde forming) is encoded by a gene selected from the group consisting of acr1, sucD, bphG, msed_0709, mcr, asd-2, and saci_2370.

8. The organism of claim 1, wherein said 1,4-butanediol dehydrogenase is encoded by a gene selected from the group consisting of alrA, adh2, yqhD, bdh I, bdh II, and 4hbd.

9. The organism of claim 1, wherein said corrinoid protein is encoded by a gene selected from the group consisting of mtaC, mtaC1, mtaC2, and mtaC3.

10. The organism of claim 1, wherein said methyltetrahydrofolate:corrinoid protein methyltransferase is encoded by a gene selected from the group consisting of mtaA, and mtaA1, mtaA2.

11. The organism of claim 1, wherein said methyltetrahydrofolate:corrinoid protein methyltransferase is encoded by the gene acsE.

12. The organism of claim 1, wherein said corrinoid iron-sulfur protein is encoded by the gene acsD.

13. The organism of claim 1, wherein said nickel-protein assembly protein is encoded by at least one gene selected from the group consisting of acsF and cooC.

14. The organism of claim 1, wherein said ferredoxin is encoded by the gene orf7.

15. The organism of claim 1, wherein said carbon monoxide dehydrogenase is encoded by the gene acsA.

16. The organism of claim 1, wherein said pyruvate ferredoxin oxidoreductase is encoded by a gene selected from the group consisting of por and ydbK.

17. The organism of claim 1, wherein said hydrogenase is encoded by at least one gene selected from the group consisting of hypA, hypB, hypC, hypD, hypE, hypF, moth_2175, moth_2176, moth_2177, moth_2178, moth_2179, moth_2180, moth_2181, hycA, hycB, hycC, hycD, hycE, hycF, hycG, hycH, hycI, hyfA, hyfB, hyfC, hyfD, hyfE, hyfF, hyfG, hyfH, hyfI, hyfJ, hyfR, moth_2182, moth_2183, moth_2184, moth_2185, moth_2186, moth_2187, moth_2188, moth_2189, moth_2190, moth_2191, moth_2192, moth_0439, moth_0440, moth_0441, moth_0442, moth_0809, moth_0810, moth_0811, moth_0812, moth_0813, moth_0814, moth_0815, moth_0816, moth_1193, moth_1194, moth_1195, moth_1196, moth_1717, moth_1718, moth_1719, moth_1883, moth_1884, moth_1885, moth_1886, moth_1887, moth_1888, moth_1452, moth_1453, and moth_1454.

18. The organism of claim 1, further comprising the polypeptide_AcsEps encoded by the gene acsEps.

19. The organism of claim 1, further comprising at least one enzyme or polypeptide encoded by a gene selected from the group consisting of codh, codh-I, cooF, hypA, cooH, cooU, cooX, cooL, cooK, cooM, cooT, cooJ, and codh-II.

20. The organism of claim 1, further comprising a methanol methyltransferase.

21. The organism of claim 20, wherein said methanol methyltransferase is encoded by a gene selected from the group consisting of mtaB, mtaB1, mtaB2, and mtaB3.

22. The organism of claim 20, wherein said organism utilizes a feedstock selected from the group consisting of: 1) methanol and CO, 2) methanol, $CO_2$, and $H_2$, 3) methanol, CO, $CO_2$, and $H_2$, 4) methanol and synthesis gas comprising CO and $H_2$, 5) methanol and synthesis gas comprising CO, $CO_2$, and $H_2$, 6) one or more carbohydrates, 7) methanol and one or more carbohydrates, and 8) methanol.

23. A method for producing 1,4-butanediol, comprising culturing the non-naturally occurring microbial organism of claim 1.

* * * * *